United States Patent [19]

Davis et al.

[11] Patent Number: 5,736,381

[45] Date of Patent: Apr. 7, 1998

[54] CYTOKINE-, STRESS-, AND ONCOPROTEIN-ACTIVATED HUMAN PROTEIN KINASE KINASES

[76] Inventors: Roger J. Davis, 53 Hickory Dr., Princeton, Mass. 01541; Shashi Gupta, 807 Franklin St., Worcester, Mass. 01604; Joel Raingeaud, Sainte Marie, 85390 Bazoges en Pareds; Benoit Derijard, 36 Rue de l'aiguillette, Bat. C1, 13012 Marseille, both of France

[21] Appl. No.: 530,950

[22] Filed: Sep. 19, 1995

Related U.S. Application Data

[63] Continuation-in-part of Ser. No. 446,083, May 19, 1995.

[51] Int. Cl.$^6$ ............ C12N 1/20; C12N 15/00; C07H 21/04; C12P 21/06
[52] U.S. Cl. ............ 435/252.3; 435/6; 435/91.1; 435/69.1; 435/325; 435/320.1; 536/23.1; 536/23.5; 536/24.31; 536/24.33; 935/1; 935/8; 935/22; 935/66
[58] Field of Search ............ 435/6, 91.1, 69.1, 435/325, 252.3, 320.1, 183; 536/23.1, 23.5, 24.31, 24.33; 935/1, 8, 22, 66

[56] References Cited

FOREIGN PATENT DOCUMENTS

WO 94/24159 10/1994 WIPO.
WO 95/28421 10/1995 WIPO.
PCT/US96/01078 5/1996 WIPO.

OTHER PUBLICATIONS

Serger et al., "Human T–cell Mitogen–activated Protein Kinase Kinases Are Related to Yeast Signal Transduction Kinases," The Journal of Biological Chemistry, vol. 267, No. 36, pp. 25628–25631, Dec. 25, 1992.

Wu et al., "Identification and Characterization of a New Mammalian Mitogen–Activated Protein Kinase Kinase, MKK2," Molecular and Cellular Biology, vol. 13, No. 8, pp. 4539–4548, Aug. 1993.
Davis, *Elsevier Science Ltd.*, TIBS 19:470–473, (1994).
Dérijard et al., *Science*, 267:682–685, (1995).
Freshney et al., *Cell*, 78:1039–1049, (1994).
Galcheva–Gargova et al., *Science*, 265:806–808, (1994).
Gupta et al., *Science*, 267:389–393, (1995).
Lin et al., *Science*, 268:286–290, (1995).
Minden et al., *Science*, 266:1719–1723, (1994).
Raingeaud et al., *The Journal of Biological Chemistry*, 270:7420–7426, (1995).
Rouse et al., *Cell*, 78:1027–1037, (1994).
Sanchez et al., *Nature*, 372:794–798, (1994).
Whitmarsh, et al., *Science*, 269:403–407, (1995).
Xia et al., *Science*, 270:1326–1331, (1995).
Yan et al., *Nature*, 372:798–800, (1994).
Yashar et al., *Molecular and Cellular Biology*, 13:5738–5748, (1993).
Seger et al., "Human T–Cell Mitogen–Activated Protein Kinases Are Related to Yeast Signal Transduction Kinases," *J. Biological Chemistry*, 267:25628–25631 (1992).

*Primary Examiner*—Bradley L. Sisson
*Attorney, Agent, or Firm*—Fish & Richardson P.C.

[57] ABSTRACT

Disclosed are human mitogen-activated (MAP) kinase kinase isoforms (MKKs). MKKs mediate unique signal transduction pathways that activate human MAP kinases p38 and JNK, which result in activation of other factors, including activating transcription factor-2 (ATF2) and c-Jun. The pathways are activated by a number of factors, including cytokines and environmental stress. Methods are provided for identifying reagents that modulate MKK function or activity and for the use of such reagents in the treatment of MKK-mediated disorders.

20 Claims, 28 Drawing Sheets

```
                                                                                          71
MKK3                             MSKPP--------APNPTPPRN-----------LDSRTFITIG------DRNFEVEADD
MKK4       MQGKRKALKLNFAN..FKSTARFTLN...GVQ.PHIERLRTHSIE.SGKLK.SP------EQHWDFT.E.
MEK1              MPKKKP---TPIQLN.A-PDGSAVNGTSSAETNLEALQKLEEELE..EQORKRLEAFLTQKQKVG.LKD..
MEK2       MLARRKPVLPALTIN.TIAEGPSPTSEGASEANLVDLQKKLEELE..EQQKKRLEAFLTQKAKVG.LKD..
PBS2       <GTTPRTGNSNNS-NSGSSGGGLFANFSKYVDIKSGSLNPAGKLSL.SKG.DFSN-----GSSSRITL.E
Consensus I                II               III            IV                142
MKK3       LVTISELGRGAYGVVEKVRHAQSGTIMAVKRIRATVNSQEQKRLLMDLDINMRTVDCFYTVTFYGALFREG
MKK4       .KDLG.I.......S.N.MV.KP..Q.........S..DEK...Q......VV..SS..P.I.Q.......
MEK1       .FEK......A.NG....F.VS.KP..LV...R.L.HLEIKPAIRNQIRE..QV-LHECNSP.I.G.....FYSD.
MEK2       .FER......A.NG....T.VQ.RP..L...R.L.HLEIKPAIRNQIRE..QV-LHECNSP.I.G.....FYSD.
PBS2       .EFLD..H.N..N.S.VL.KPTNV..T.EV.LELDEAKFRQI..E.EV-LHKCNSP.I.D...F.I..
Consensus            EGG  GVK H    MA K                L                     Y V FYGA    G 143   V                                                VI                  213
MKK3       DVWICMELMD-TSLDKFYR---KVLDKNMTIPEDILGEIAVSIVRALEHLHSKLSVIHRDVKPSNVL-INK
MKK4       .C........S-..F....KYVYS...D-V....E....K.TLAT.K..N..KEN.KI.....I....I.-LDR
MEK1       EIS........H..GG....Q---------.K.AGR....Q...KVSIAVTKG.TY.RE.HKIM........I.-V.S
MEK2       EIS........H..GG....Q---------.KEAKR....E...KVSIAVL.G.AY.RE.HQIM........I.-V.S
PBS2       A.YM...Y..GG.....IYDESSEIGG-----.D.PQ.AF..NAVIHG.KE.KEQHNI......T.I.CSAN
Consensus            CME M   S  D                    I E   L   L         HRD KP N  L 214   VII                      VIII                  IX                  284
MKK3       EGHVKMCDFGISGYLVDSVAKTMDAGCKPYMAPERINP-ELNQKGYNVKSDVWSLGITMIEMAILRFPY--
MKK4       S.NI.L......Q....I...R...R.......D.-SASRQ..D.R.......LY.L.TG....
MEK1       R.EI.L......V..Q.I..M.NSF-V.TRS...S....LQGTH----.S.Q..I..M.LSLV...VG.Y.IPP
MEK2       R.EI.L......V..Q.I..M.NSF-V.TRS........LQGTH----.S.Q..I..M.LSLV.L.VG.Y.IPP
PBS2       Q.T..L......V..N..A.L....NI...QS.......KSLNPDRAT.T.Q..I......LSIL....LG.Y..PP
Consensus      G  K CDFG SG L S A       G   YM PER               Y V SD WS G    E A  R P 285                                                                        355
MKK3       ESWG-----------------------------------------------TPFQQLKQVVEEPSPQLPAD--R
MKK4       PK.N-----------------------------------------------SV.D..T....KGDP...SNSEERE
MEK1       PDAKELELMFGCQV-----EGDAAETPPRPRTPGRPLSSYGMDSRPPMAI.EL.DYI.N..P.K..SGV---
MEK2       PDAKELEAIFGRPVVDGEEGEPHSISPRPRPPGRPVSGHGMDSRPAMAI.EL.DYI.N..P.K..NGV---
PBS2       .TYD-----------------------------------------------NI.S..SAI.DG.P.R..S.---K
Consensus                                                                F  L  V   P  L 356                                                                       426
MKK3       FSPEFVDFTAQCLRKNPAERMSYLELMEHPFFTLHKTKKTDIAAFVK---------KILGEDS
MKK4       ...S.IN.VNL..T.DESK..PK.K..LK...ILMYEERAVEV.CY.C---------.DQMPATPSSPMYVD
MEK1       ...L..Q..VNK..I......ADLKQ..V.A.IKRSDAEEV..F.GWLCSTIGLNQPSTPTHAAGV
MEK2       .T.D.QE.VNK..I......ADLKM.TN.T..IKRSEVEEV.F.GWLCKTLRLNQPGTPTRTA
PBS2       .SDAQD.VSL...Q.I.ER.PT.AA.T..PWLVKYRNQDVHMSEYITERLERRN...R.RGENGLSKNVP>
Consensus   F   F   CL K    R          L H

FIG. 1
```

```
         5        10        15        20        25        30        35        40        45        50        55        60
         *         *         *         *         *         *         *         *         *         *         *         *
TGGCTGGCAA TGGCCTTGCT GACCTCGAGC CGGGCCCACG TGGGGACCTT TGGAGCACAG
ACCGACCGTT ACCGGAACGA CTGGAGCTCG GCCCGGGTGC ACCCCTGGAA ACCTCGTGTC 65        70        75        80        85        90        95       100       105       110       115       120
         *         *         *         *         *         *         *         *         *         *         *         *
CCTACGATCC TGGTGCAAGG CCGGTGGATG CAGAGGCCAG TCCATATACC ACCCAGGCCT
GGATGCTAGG ACCACGTTCC GGCCACCTAC GTCTCCGGTC AGGTATATGG TGGGTCCGGA 125       130       135       140       145       150       155       160       165       170       175       180
         *         *         *         *         *         *         *         *         *         *         *         *
GCGAGGAGCG TGGTCCCCAC CCATCCAGCC CATATGTGCA AGTGCCCTTG ACAGAGAGGC
CGCTCCTCGC ACCAGGGGTG GGTAGGTCGG GTATACACGT TCACGGGAAC TGTCTCTCCG 185       190       195       200       205       210       215       220       225       230       235       240
         *         *         *         *         *         *         *         *         *         *         *         *
TGGTCATATC CATGGTGACC ATTTATGGGC CACAACAGGT CCCCATCTGC GCAGTGAACC
ACCAGTATAG GTACCACTGG TAAATACCCG GTGTTGTCCA GGGGTAGACG CGTCACTTGG 245       250       255       260       265       270       275       280       285       290       295       300
         *         *         *         *         *         *         *         *         *         *         *         *
CTGTGCTGAG CACCTTGCAG ACGTGATCTT GCTTCGTCCT GCAGCACTGT GCGGGGCAGG
GACACGACTC GTGGAACGTC TGCACTAGAA CGAAGCAGGA CGTCGTGACA CGCCCCGTCC 305       310       315       320       325       330       335       340       345       350       355
         *         *         *         *         *         *         *         *         *         *         *
AAAATCCAAG AGGAAGAAGG ATCTACGGAT ATCCTGC ATG TCC AAG CCA CCC GCA
TTTTAGGTTC TCCTTCTTCC TAGATGCCTA TAGGACG TAC AGG TTC GGT GGG CGT
                                         Met Ser Lys Pro Pro Ala>

360       365       370       375       380       385       390       395       400
             *         *         *         *         *         *         *         *         *
CCC AAC CCC ACA CCC CCC CGG AAC CTG GAC TCC CGG ACC TTC ATC ACC
GGG TTG GGG TGT GGG GGG GCC TTG GAC CTG AGG GCC TGG AAG TAG TGG
Pro Asn Pro Thr Pro Pro Arg Asn Leu Asp Ser Arg Thr Phe Ile Thr>

405       410       415       420       425       430       435       440       445       450
  *         *         *         *         *         *         *         *         *         *
ATT GGA GAC AGA AAC TTT GAG GTG GAG GCT GAT GAC TTG GTG ACC ATC
TAA CCT CTG TCT TTG AAA CTC CAC CTC CGA CTA CTG AAC CAC TGG TAG
Ile Gly Asp Arg Asn Phe Glu Val Glu Ala Asp Asp Leu Val Thr Ile>

455       460       465       470       475       480       485       490       495
      *         *         *         *         *         *         *         *         *
TCA GAA CTG GGC CGT GGA GCC TAT GGG GTG GTA GAG AAG GTG CGG CAC
AGT CTT GAC CCG GCA CCT CGG ATA CCC CAC CAT CTC TTC CAC GCC GTG
Ser Glu Leu Gly Arg Gly Ala Tyr Gly Val Val Glu Lys Val Arg His>

500       505       510       515       520       525       530       535       540       545
  *         *         *         *         *         *         *         *         *         *
GCC CAG AGC GGC ACC ATC ATG GCC GTG AAG CGG ATC CGG GCC ACC GTG
CGG GTC TCG CCG TGG TAG TAC CGG CAC TTC GCC TAG GCC CGG TGG CAC
Ala Gln Ser Gly Thr Ile Met Ala Val Lys Arg Ile Arg Ala Thr Val>

550       555       560       565       570       575       580       585       590       595
        *         *         *         *         *         *         *         *         *         *
AAC TCA CAG GAG CAG AAG CGG CTG CTC ATG GAC CTG GAC ATC AAC ATG
TTG AGT GTC CTC GTC TTC GCC GAC GAG TAC CTG GAC CTG TAG TTG TAC
Asn Ser Gln Glu Gln Lys Arg Leu Leu Met Asp Leu Asp Ile Asn Met>
```

FIG. 4A

```
      600       605       610       615       620       625       630       635       640
       *                   *                   *                   *                   *
      CGC ACG GTC GAC TGT TTC TAC ACT GTC ACC TTC TAC GGG GCA CTA TTC
      GCG TGC CAG CTG ACA AAG ATG TGA CAG TGG AAG ATG CCC CGT GAT AAG
      Arg Thr Val Asp Cys Phe Tyr Thr Val Thr Phe Tyr Gly Ala Leu Phe>

645       650       655       660       665       670       675       680       685       690
   *                   *                   *                   *                   *
  AGA GAG GGA GAC GTG TGG ATC TGC ATG GAG CTC ATG GAC ACA TCC TTG
  TCT CTC CCT CTG CAC ACC TAG ACG TAC CTC GAG TAC CTG TGT AGG AAC
  Arg Glu Gly Asp Val Trp Ile Cys Met Glu Leu Met Asp Thr Ser Leu>

695       700       705       710       715       720       725       730       735
            *                   *                   *                   *
          GAC AAG TTC TAC CGG AAG GTG CTG GAT AAA AAC ATG ACA ATT CCA GAG
          CTG TTC AAG ATG GCC TTC CAC GAC CTA TTT TTG TAC TGT TAA GGT CTC
          Asp Lys Phe Tyr Arg Lys Val Leu Asp Lys Asn Met Thr Ile Pro Glu>

740       745       750       755       760       765       770       775       780       785
   *                   *                   *                   *                   *
  GAC ATC CTT GGG GAG ATT GCT GTG TCT ATC GTG CGG GCC CTG GAG CAT
  CTG TAG GAA CCC CTC TAA CGA CAC AGA TAG CAC GCC CGG GAC CTC GTA
  Asp Ile Leu Gly Glu Ile Ala Val Ser Ile Val Arg Ala Leu Glu His>

790       795       800       805       810       815       820       825       830       835
                   *                   *                   *                   *
      CTG CAC AGC AAG CTG TCG GTG ATC CAC AGA GAT GTG AAG CCC TCC AAT
      GAC GTG TCG TTC GAC AGC CAC TAG GTG TCT CTA CAC TTC GGG AGG TTA
      Leu His Ser Lys Leu Ser Val Ile His Arg Asp Val Lys Pro Ser Asn>

840       845       850       855       860       865       870       875       880
            *                   *                   *                   *
          GTC CTT ATC AAC AAG GAG GGC CAT GTG AAG ATG TGT GAC TTT GGC ATC
          CAG GAA TAG TTG TTC CTC CCG GTA CAC TTC TAC ACA CTG AAA CCG TAG
          Val Leu Ile Asn Lys Glu Gly His Val Lys Met Cys Asp Phe Gly Ile>

885       890       895       900       905       910       915       920       925       930
   *                   *                   *                   *                   *
  AGT GGC TAC TTG GTG GAC TCT GTG GCC AAG ACG ATG GAT GCC GGC TGC
  TCA CCG ATG AAC CAC CTG AGA CAC CGG TTC TGC TAC CTA CGG CCG ACG
  Ser Gly Tyr Leu Val Asp Ser Val Ala Lys Thr Met Asp Ala Gly Cys>

935       940       945       950       955       960       965       970       975
       *                   *                   *                   *
      AAG CCC TAC ATG GCC CCT GAG AGG ATC AAC CCA GAG CTG AAC CAG AAG
      TTC GGG ATG TAC CGG GGA CTC TCC TAG TTG GGT CTC GAC TTG GTC TTC
      Lys Pro Tyr Met Ala Pro Glu Arg Ile Asn Pro Glu Leu Asn Gln Lys>

980       985       990       995      1000      1005      1010      1015      1020      1025
   *                   *                   *                   *                   *
  GGC TAC AAT GTC AAG TCC GAC GTC TGG AGC CTG GGC ATC ACC ATG ATT
  CCG ATG TTA CAG TTC AGG CTG CAG ACC TCG GAC CCG TAG TGG TAC TAA
  Gly Tyr Asn Val Lys Ser Asp Val Trp Ser Leu Gly Ile Thr Met Ile>

1030      1035      1040      1045      1050      1055      1060      1065      1070      1075
       *                   *                   *                   *                   *
      GAG ATG GCC ATC CTG CGG TTC CCT TAC GAG TCC TGG GGG ACC CCG TTC
      CTC TAC CGG TAG GAC GCC AAG GGA ATG CTC AGG ACC CCC TGG GGC AAG
      Glu Met Ala Ile Leu Arg Phe Pro Tyr Glu Ser Trp Gly Thr Pro Phe>

```
       •           •           •           •           •
CAG CAG CTG AAG CAG GTG GTG GAG GAG CCG TCC CCC CAG CTC CCA GCC
GTC GTC GAC TTC GTC CAC CAC CTC CTC GGC AGG GGG GTC GAG GGT CGG
Gln Gln Leu Lys Gln Val Val Glu Glu Pro Ser Pro Gln Leu Pro Ala>

1125  1130  1135  1140  1145  1150  1155  1160  1165  1170
        •           •           •           •           •
GAC CGT TTC TCC CCC GAG TTT GTG GAC TTC ACT GCT CAG TGC CTG AGG
CTG GCA AAG AGG GGG CTC AAA CAC CTG AAG TGA CGA GTC ACG GAC TCC
Asp Arg Phe Ser Pro Glu Phe Val Asp Phe Thr Ala Gln Cys Leu Arg>

1175  1180  1185  1190  1195  1200  1205  1210  1215
  •           •           •           •
AAG AAC CCC GCA GAG CGT ATG AGC TAC CTG GAG CTG ATG GAG CAC CCC
TTC TTG GGG CGT CTC GCA TAC TCG ATG GAC CTC GAC TAC CTC GTG GGG
Lys Asn Pro Ala Glu Arg Met Ser Tyr Leu Glu Leu Met Glu His Pro>

1220  1225  1230  1235  1240  1245  1250  1255  1260  1265
  •           •           •           •           •
TTC TTC ACC TTG CAC AAA ACC AAG AAG ACG GAC ATT GCT GCC TTC GTG
AAG AAG TGG AAC GTG TTT TGG TTC TTC TGC CTG TAA CGA CGG AAG CAC
Phe Phe Thr Leu His Lys Thr Lys Lys Thr Asp Ile Ala Ala Phe Val>

1270  1275  1280  1285  1290  1295 1300  1305 1310  1315 1320
        •           •           •           •           •
AAG AAG ATC CTG GGA GAA GAC TCA TAGGGGCTG GGCCTCGGAC CCCACTCCGG
TTC TTC TAG GAC CCT CTT CTG AGT ATCCCCGAC CCGGAGCCTG GGGTGAGGCC
Lys Lys Ile Leu Gly Glu Asp Ser> (SEQ ID NO:2)

1325 1330  1335 1340  1345 1350  1355 1360  1365 1370  1375 1380
        •           •           •           •           •
CCCTCCAGAG CCCCACAGCC CCATCTGCGG GGGCAGTGCT CACCCACACC ATAAGCTACT
GGGAGGTCTC GGGGTGTCGG GGTAGACGCC CCCGTCACGA GTGGGTGTGG TATTCGATGA 1385 1390  1395 1400  1405 1410  1415 1420  1425 1430  1435 1440
        •           •           •           •           •
GCCATCCTGG CCCAGGGCAT CTGGGAGGAA CCGAGGGGGC TGCTCCCACC TGGCTCTGTG
CGGTAGGACC GGGTCCCGTA GACCCTCCTT GGCTCCCCCG ACGAGGGTGG ACCGAGACAC 1445 1450  1455 1460  1465 1470  1475 1480  1485 1490  1495 1500
        •           •           •           •           •
GCGAGCCATT TGTCCCAAGT GCCAAAGAAG CAGACCATTG GGGCTCCCAG CCAGGCCCTT
CGCTCGGTAA ACAGGGTTCA CGGTTTCTTC GTCTGGTAAC CCCGAGGGTC GGTCCGGGAA 1505 1510  1515 1520  1525 1530  1535 1540  1545 1550  1555 1560
        •           •           •           •           •
GTCGGCCCCA CCAGTGCCTC TCCCTGCTGC TCCTAGGACC CGTCTCCAGC TGCTGAGATC
CAGCCGGGGT GGTCACGGAG AGGGACGACG AGGATCCTGG GCAGAGGTCG ACGACTCTAG 1565 1570  1575 1580  1585 1590  1595 1600  1605 1610  1615 1620
        •           •           •           •           •
CTGGACTGAG GGGGCCTGGA TGCCCCCTGT GGATGCTGCT GCCCCTGCAC AGCAGGCTGC
GACCTGACTC CCCCGGACCT ACGGGGGACA CCTACGACGA CGGGGACGTG TCGTCCGACG 1625 1630  1635 1640  1645 1650  1655 1660  1665 1670  1675 1680
        •           •           •           •           •
CAGTGCCTGG GTGGATGGGC CACCGCCTTG CCCAGCCTGG ATGCCATCCA AGTTGTATAT
GTCACGGACC CACCTACCCG GTGGCGGAAC GGGTCGGACC TACGGTAGGT TCAACATATA 1685 1690  1695 1700  1705 1710  1715 1720  1725 1730  1735 1740
        •           •           •           •           •
TTTTTTAATC TCTCGACTGA ATGGACTTTG CACACTTTGG CCCAGGGTGG CCACACCTCT
```

FIG. 4C

```
AAAAAATTAG AGAGCTGACT TACCTGAAAC GTGTGAAACC GGGTCCCACC GGTGTGGAGA 1745 1750   1755 1760   1765 1770   1775 1780   1785 1790   1795 1800
            *           *           *           *           *           *
         ATCCCGGCTT TGGTGCGGGG TACACAAGAG GGGATGAGTT GTGTGAATAC CCCAAGACTC
         TAGGGCCGAA ACCACGCCCC ATGTGTTCTC CCCTACTCAA CACACTTATG GGGTTCTGAG 1805 1810   1815 1820   1825 1830   1835 1840   1845 1850   1855 1860
            *           *           *           *           *           *
         CCATGAGGGA GATGCCATGA GCCGCCCAAG GCCTTCCCCT GGCACTGGCA AACAGGGCCT
         GGTACTCCCT CTACGGTACT CGGCGGGTTC CGGAAGGGGA CCGTGACCGT TTGTCCCGGA 1865 1870   1875 1880   1885 1890   1895 1900   1905 1910   1915 1920
            *           *           *           *           *           *
         CTGCGGAGCA CACTGGCTCA CCCAGTCCTG CCCGCCACCG TTATCGGTGT CATTCACCTT
         GACGCCTCGT GTGACCGAGT GGGTCAGGAC GGGCGGTGGC AATAGCCACA GTAAGTGGAA 1925 1930   1935 1940   1945 1950   1955 1960   1965 1970   1975 1980
            *           *           *           *           *           *
         TCGTGTTTTT TTTAATTTAT CCTCTGTTGA TTTTTTCTTT TGCTTTATGG GTTTGGCTTG
         AGCACAAAAA AAATTAAATA GGAGACAACT AAAAAAGAAA ACGAAATACC CAAACCGAAC 1985 1990   1995 2000   2005 2010   2015 2020   2025 2030
            *           *           *           *           *
         TTTTTCTTGC ATGGTTTGGA GCTGATCGCT TCTCCCCCAC CCCCTAGGGG  (SEQ ID NO: 1)
         AAAAAGAACG TACCAAACCT CGACTAGCGA AGAGGGGGTG GGGGATCCCC
```

FIG. 4D

```
                  5        10        15        20        25        30        35        40        45        50        55        60
                  *                  *                   *                   *                   *                   *
           TAGCTGCAGC ACAGCCTTCC CTAACGTTGC AACTGGGGGA AAAATCACTT TCCAGTCTGT
           ATCGACGTCG TGTCGGAAGG GATTGCAACG TTGACCCCCT TTTTAGTGAA AGGTCAGACA 65        70        75        80        85        90        95       100       105       110       115       120
                  *                  *                   *                   *                   *                   *
           TTTGCAAGGT GTGCATTTCC ATCTTGATTC CCTGAAAGTC CATCTGCTGC ATCGGTCAAG
           AAACGTTCCA CACGTAAAGG TAGAACTAAG GGACTTTCAG GTAGACGACG TAGCCAGTTC 125       130       135       140       145       150       155       160       165       170       175       180
                  *                  *                   *                   *                   *                   *
           AGAAACTCCA CTTGCATGAA GATTGCACGC CTGCAGCTTG CATCTTTGTT GCAAAACTAG
           TCTTTGAGGT GAACGTACTT CTAACGTGCG GACGTCGAAC GTAGAAACAA CGTTTTGATC 185       190       195       200       205       210       215       220       225       230       235       240
                  *                  *                   *                   *                   *                   *
           CTACAGAAGA GAAGCAAGGC AAAGTCTTTT GTGCTCCCCT CCCCCATCAA AGGAAAGGGG
           GATGTCTTCT CTTCGTTCCG TTTCAGAAAA CACGAGGGGA GGGGGTAGTT TCCTTTCCCC 245       250       255       260       265       270       275       280       285
                 *                   *                   *                   *
           AAA ATG TCT CAG TCG AAA GGC AAG AAG CGA AAC CCT GGC CTT AAA ATT
           TTT TAC AGA GTC AGC TTT CCG TTC TTC GCT TTG GGA CCG GAA TTT TAA
               Met Ser Gln Ser Lys Gly Lys Lys Arg Asn Pro Gly Leu Lys Ile>

290       295       300       305       310       315       320       325       330       335
             *                   *                   *                   *                   *
           CCA AAA GAA GCA TTT GAA CAA CCT CAG ACC AGT TCC ACA CCA CCT AGA
           GGT TTT CTT CGT AAA CTT GTT GGA GTC TGG TCA AGG TGT GGT GGA TCT
           Pro Lys Glu Ala Phe Glu Gln Pro Gln Thr Ser Ser Thr Pro Pro Arg>

340       345       350       355       360       365       370       375       380
             *                   *                   *                   *                   *
           GAT TTA GAC TCC AAG GCT TGC ATT TCT ATT GGA AAT CAG AAC TTT GAG
           CTA AAT CTG AGG TTC CGA ACG TAA AGA TAA CCT TTA GTC TTG AAA CTC
           Asp Leu Asp Ser Lys Ala Cys Ile Ser Ile Gly Asn Gln Asn Phe Glu>

385       390       395       400       405       410       415       420       425       430
             *                   *                   *                   *                   *
           GTG AAG GCA GAT GAC CTG GAG CCT ATA ATG GAA CTG GGA CGA GGT GCG
           CAC TTC CGT CTA CTG GAC CTC GGA TAT TAC CTT GAC CCT GCT CCA CGC
           Val Lys Ala Asp Asp Leu Glu Pro Ile Met Glu Leu Gly Arg Gly Ala>

435       440       445       450       455       460       465       470       475       480
             *                   *                   *                   *                   *
           TAC GGG GTG GTG GAG AAG ATG CGG CAC GTG CCC AGC GGG CAG ATC ATG
           ATG CCC CAC CAC CTC TTC TAC GCC GTG CAC GGG TCG CCC GTC TAG TAC
           Tyr Gly Val Val Glu Lys Met Arg His Val Pro Ser Gly Gln Ile Met>

485       490       495       500       505       510       515       520       525
             *                   *                   *                   *
           GCA GTG AAG CGG ATC CGA GCC ACA GTA AAT AGC CAG GAA CAG AAA CGG
           CGT CAC TTC GCC TAG GCT CGG TGT CAT TTA TCG GTC CTT GTC TTT GCC
           Ala Val Lys Arg Ile Arg Ala Thr Val Asn Ser Gln Glu Gln Lys Arg>

530       535       540       545       550       555       560       565       570       575
             *                   *                   *                   *                   *
           CTA CTG ATG GAT TTG GAT ATT TCC ATG AGG ACG GTG GAC TGT CCA TTC
           GAT GAC TAC CTA AAC CTA TAA AGG TAC TCC TGC CAC CTG ACA GGT AAG
```

FIG. 5A

```
      Leu Leu Met Asp Leu Asp Ile Ser Met Arg Thr Val Asp Cys Pro Phe>
      580     585     590     595     600     605     610     615     620
       *               *               *               *               *
      ACT GTC ACC TTT TAT GGC GCA CTG TTT CGG GAG GGT GAT GTG TGG ATC
      TGA CAG TGG AAA ATA CCG CGT GAC AAA GCC CTC CCA CTA CAC ACC TAG
      Thr Val Thr Phe Tyr Gly Ala Leu Phe Arg Glu Gly Asp Val Trp Ile>
625     630     635     640     645     650     655     660     665     670
 *               *               *               *               *
TGC ATG GAG CTC ATG GAT ACA TCA CTA GAT AAA TTC TAC AAA CAA GTT
ACG TAC CTC GAG TAC CTA TGT AGT GAT CTA TTT AAG ATG TTT GTT CAA
Cys Met Glu Leu Met Asp Thr Ser Leu Asp Lys Phe Tyr Lys Gln Val>
       675     680     685     690     695     700     705     710     715     720
        *               *               *               *               *
       ATT GAT AAA GGC CAG ACA ATT CCA GAG GAC ATC TTA GGG AAA ATA GCA
       TAA CTA TTT CCG GTC TGT TAA GGT CTC CTG TAG AAT CCC TTT TAT CGT
       Ile Asp Lys Gly Gln Thr Ile Pro Glu Asp Ile Leu Gly Lys Ile Ala>
            725     730     735     740     745     750     755     760     765
             *               *               *               *
            GTT TCT ATT GTA AAA GCA TTA GAA CAT TTA CAT AGT AAG CTG TCT GTC
            CAA AGA TAA CAT TTT CGT AAT CTT GTA AAT GTA TCA TTC GAC AGA CAG
            Val Ser Ile Val Lys Ala Leu Glu His Leu His Ser Lys Leu Ser Val>
     770     775     780     785     790     795     800     805     810     815
      *               *               *               *               *
     ATT CAC AGA GAC GTC AAG CCT TCT AAT GTA CTC ATC AAT GCT CTC GGT
     TAA GTG TCT CTG CAG TTC GGA AGA TTA CAT GAG TAG TTA CGA GAG CCA
     Ile His Arg Asp Val Lys Pro Ser Asn Val Leu Ile Asn Ala Leu Gly>
           820     825     830     835     840     845     850     855     860
            *               *               *               *               *
           CAA GTG AAG ATG TGC GAT TTT GGA ATC AGT GGC TAC TTG GTG GAC TCT
           GTT CAC TTC TAC ACG CTA AAA CCT TAG TCA CCG ATG AAC CAC CTG AGA
           Gln Val Lys Met Cys Asp Phe Gly Ile Ser Gly Tyr Leu Val Asp Ser>
     865     870     875     880     885     890     895     900     905     910
      *               *               *               *               *
     GTT GCT AAA ACA ATT GAT GCA GGT TGC AAA CCA TAC ATG GCC CCT GAA
     CAA CGA TTT TGT TAA CTA CGT CCA ACG TTT GGT ATG TAC CGG GGA CTT
     Val Ala Lys Thr Ile Asp Ala Gly Cys Lys Pro Tyr Met Ala Pro Glu>
     915     920     925     930     935     940     945     950     955     960
      *               *               *               *               *
     AGA ATA AAC CCA GAG CTC AAC CAG AAG GGA TAC AGT GTG AAG TCT GAC
     TCT TAT TTG GGT CTC GAG TTG GTC TTC CCT ATG TCA CAC TTC AGA CTG
     Arg Ile Asn Pro Glu Leu Asn Gln Lys Gly Tyr Ser Val Lys Ser Asp>
           965     970     975     980     985     990     995     1000    1005
            *               *               *               *
           ATT TGG AGT CTG GGC ATC ACG ATG ATT GAG TTG GCC ATC CTT CGA TTT
           TAA ACC TCA GAC CCG TAG TGC TAC TAA CTC AAC CGG TAG GAA GCT AAA
           Ile Trp Ser Leu Gly Ile Thr Met Ile Glu Leu Ala Ile Leu Arg Phe>
     1010    1015    1020    1025    1030    1035    1040    1045    1050    1055
      *               *               *               *               *
     CCC TAT GAT TCA TGG GGA ACT CCA TTT CAG CAG CTC AAA CAG GTG GTA
     GGG ATA CTA AGT ACC CCT TGA GGT AAA GTC GTC GAG TTT GTC CAC CAT
     Pro Tyr Asp Ser Trp Gly Thr Pro Phe Gln Gln Leu Lys Gln Val Val>
```

FIG. 5B

```
     1060     1065     1070     1075     1080     1085     1090     1095     1100
      *                 *                 *                 *                 *
     GAG GAG CCA TCG CCA CAA CTC CCA GCA GAC AAG TTC TCT GCA GAG TTT
     CTC CTC GGT AGC GGT GTT GAG GGT CGT CTG TTC AAG AGA CGT CTC AAA
     Glu Glu Pro Ser Pro Gln Leu Pro Ala Asp Lys Phe Ser Ala Glu Phe>

1105     1110     1115     1120     1125     1130     1135     1140     1145     1150
  *                 *                 *                 *                 *
 GTT GAC TTT ACC TCA CAG TGC TTA AAG AAG AAT TCC AAA GAA CGG CCT
 CAA CTG AAA TGG AGT GTC ACG AAT TTC TTC TTA AGG TTT CTT GCC GGA
 Val Asp Phe Thr Ser Gln Cys Leu Lys Lys Asn Ser Lys Glu Arg Pro>

1155     1160     1165     1170     1175     1180     1185     1190     1195     1200
      *                 *                 *                 *                 *
  ACA TAC CCA GAG CTA ATG CAA CAT CCA TTT TTC ACC CTA CAT GAA TCC
  TGT ATG GGT CTC GAT TAC GTT GTA GGT AAA AAG TGG GAT GTA CTT AGG
  Thr Tyr Pro Glu Leu Met Gln His Pro Phe Phe Thr Leu His Glu Ser>

1205     1210     1215     1220     1225     1230     1235     1240     1245     1250
           *                 *                 *                 *                 *
      AAA GGA ACA GAT GTG GCA TCT TTT GTA AAA CTG ATT CTT GGA GAC TAAAA
      TTT CCT TGT CTA CAC CGT AGA AAA CAT TTT GAC TAA GAA CCT CTG ATTTT
      Lys Gly Thr Asp Val Ala Ser Phe Val Lys Leu Ile Leu Gly Asp> (SEQ ID NO:4)

1255 1260   1265 1270   1275 1280   1285 1290   1295 1300   1305 1310
            *            *            *            *            *
    AGCAGTGGAC TTAATCGGTT GACCCTACTG TGGATTGGTG GGTTTCGGGG TGAAGCAAGT
    TCGTCACCTG AATTAGCCAA CTGGGATGAC ACCTAACCAC CCAAAGCCCC ACTTCGTTCA 1315 1320   1325 1330   1335 1340   1345 1350   1355 1360   1365 1370
            *            *            *            *            *
    TCACTACAGC ATCAATAGAA AGTCATCTTT GAGATAATTT AACCCTGCCT CTCAGAGGGT
    AGTGATGTCG TAGTTATCTT TCAGTAGAAA CTCTATTAAA TTGGGACGGA GAGTCTCCCA 1375 1380   1385 1390   1395 1400   1405 1410   1415 1420   1425 1430
            *            *            *            *            *
    TTTCTCTCCC AATTTTCTTT TTACTCCCCC TCTTAAGGGG GCCTTGGAAT CTATAGTATA
    AAAGAGAGGG TTAAAAGAAA AATGAGGGGG AGAATTCCCC CGGAACCTTA GATATCATAT 1435 1440   1445 1450   1455 1460   1465 1470   1475 1480   1485 1490
            *            *            *            *            *
    GAATGAACTG TCTAGATGGA TGAATTATGA TAAAGGCTTA GGACTTCAAA AGGTGATTAA
    CTTACTTGAC AGATCTACCT ACTTAATACT ATTTCCGAAT CCTGAAGTTT TCCACTAATT 1495 1500   1505 1510   1515 1520   1525 1530   1535 1540   1545 1550
            *            *            *            *            *
    ATATTTAATG ATGTGTCATA TGAGTCCTCA AAAAAAAAAA AAAAAAAAAA AAAAAAAAAA
    TATAAATTAC TACACAGTAT ACTCAGGAGT TTTTTTTTTT TTTTTTTTTT TTTTTTTTTT 1555 1560   1565 1570   1575 1580   1585 1590   1595 1600
            *            *            *            *
    AAAAAAAAAA AAAAAAAAAA AAAAAAAAAA AAAAAAAAAA AAAAAAAA AA   (SEQ ID NO:3)
    TTTTTTTTTT TTTTTTTTTT TTTTTTTTTT TTTTTTTTTT TTTTTTTT TT
```

FIG. 5C

```
              5         10         15         20         25         30         35         40         45         50         55
              *                     *                     *                     *                     *
              CTAGGGTCCC CGGCGCCAGG CCACCCGGCC GTCAGCAGC ATG CAG GGT AAA CGC AAA
              GATCCCAGGG GCCGCGGTCC GGTGGGCCGG CAGTCGTCG TAC GTC CCA TTT GCG TTT
                                                         Met Gln Gly Lys Arg Lys>

60         65         70         75         80         85         90         95         100        105
         *                     *                     *                     *                     *
         GCA CTG AAG TTG AAT TTT GCA AAT CCA CCT TTC AAA TCT ACA GCA AGG
         CGT GAC TTC AAC TTA AAA CGT TTA GGT GGA AAG TTT AGA TGT CGT TCC
         Ala Leu Lys Leu Asn Phe Ala Asn Pro Pro Phe Lys Ser Thr Ala Arg>

110        115        120        125        130        135        140        145        150
              *                     *                     *                     *                     *
              TTT ACT CTG AAT CCC AAT CCT ACA GGA GTT CAA AAC CCA CAC ATA GAG
              AAA TGA GAC TTA GGG TTA GGA TGT CCT CAA GTT TTG GGT GTG TAT CTC
              Phe Thr Leu Asn Pro Asn Pro Thr Gly Val Gln Asn Pro His Ile Glu>

155        160        165        170        175        180        185        190        195        200
                          *                     *                     *                     *         *
    AGA CTG AGA ACA CAC AGC ATT GAG TCA TCA GGA AAA CTG AAG ATC TCC
    TCT GAC TCT TGT GTG TCG TAA CTC AGT AGT CCT TTT GAC TTC TAG AGG
    Arg Leu Arg Thr His Ser Ile Glu Ser Ser Gly Lys Leu Lys Ile Ser>

205        210        215        220        225        230        235        240        245
         *                     *                     *                     *         *
         CCT GAA CAA CAC TGG GAT TTC ACT GCA GAG GAC TTG AAA GAC CTT GGA
         GGA CTT GTT GTG ACC CTA AAG TGA CGT CTC CTG AAC TTT CTG GAA CCT
         Pro Glu Gln His Trp Asp Phe Thr Ala Glu Asp Leu Lys Asp Leu Gly>

250        255        260        265        270        275        280        285        290        295
*                     *                     *                     *                     *
GAA ATT GGA CGA GGA GCT TAT GGT TCT GTC AAC AAA ATG GTC CAC AAA
CTT TAA CCT GCT CCT CGA ATA CCA AGA CAG TTG TTT TAC CAG GTG TTT
Glu Ile Gly Arg Gly Ala Tyr Gly Ser Val Asn Lys Met Val His Lys>

300        305        310        315        320        325        330        335        340        345
     *                     *                     *                     *                     *
     CCA AGT GGG CAA ATA ATG GCA GTT AAA AGA ATT CGG TCA ACA GTG GAT
     GGT TCA CCC GTT TAT TAC CGT CAA TTT TCT TAA GCC AGT TGT CAC CTA
     Pro Ser Gly Gln Ile Met Ala Val Lys Arg Ile Arg Ser Thr Val Asp>

350        355        360        365        370        375        380        385        390
          *                     *                     *                     *         *
          GAA AAA GAA CAA AAA CAA CTT CTT ATG GAT TTG GAT GTA GTA ATG CGG
          CTT TTT CTT GTT TTT GTT GAA GAA TAC CTA AAC CTA CAT CAT TAC GCC
          Glu Lys Glu Gln Lys Gln Leu Leu Met Asp Leu Asp Val Val Met Arg>

395        400        405        410        415        420        425        430        435        440
*                     *                     *                     *                     *
AGT AGT GAT TGC CCA TAC ATT GTT CAG TTT TAT GGT GCA CTC TTC AGA
TCA TCA CTA ACG GGT ATG TAA CAA GTC AAA ATA CCA CGT GAG AAG TCT
Ser Ser Asp Cys Pro Tyr Ile Val Gln Phe Tyr Gly Ala Leu Phe Arg>

445        450        455        460        465        470        475        480        485
                *                     *                     *         *
     GAG GGT GAC TGT TGG ATC TGT ATG GAA CTC ATG TCT ACC TCG TTT GAT
     CTC CCA CTG ACA ACC TAG ACA TAC CTT GAG TAC AGA TGG AGC AAA CTA
     Glu Gly Asp Cys Trp Ile Cys Met Glu Leu Met Ser Thr Ser Phe Asp>
```

```
    490     495     500     505     510     515     520     525     530     535
     *               *               *               *               *
    AAG     TTT     TAC     AAA     TAT     GTA     TAT     AGT     GTA     TTA     GAT     GAT     GTT     ATT     CCA     GAA
    TTC     AAA     ATG     TTT     ATA     CAT     ATA     TCA     CAT     AAT     CTA     CTA     CAA     TAA     GGT     CTT
    Lys     Phe     Tyr     Lys     Tyr     Val     Tyr     Ser     Val     Leu     Asp     Asp     Val     Ile     Pro     Glu>

540     545     550     555     560     565     570     575     580     585
     *               *               *               *               *
    GAA     ATT     TTA     GGC     AAA     ATC     ACT     TTA     GCA     ACT     GTG     AAA     GCA     CTA     AAC     CAC
    CTT     TAA     AAT     CCG     TTT     TAG     TGA     AAT     CGT     TGA     CAC     TTT     CGT     GAT     TTG     GTG
    Glu     Ile     Leu     Gly     Lys     Ile     Thr     Leu     Ala     Thr     Val     Lys     Ala     Leu     Asn     His>

590     595     600     605     610     615     620     625     630
             *               *               *               *               *
    TTA     AAA     GAA     AAC     TTG     AAA     ATT     ATT     CAC     AGA     GAT     ATC     AAA     CCT     TCC     AAT
    AAT     TTT     CTT     TTG     AAC     TTT     TAA     TAA     GTG     TCT     CTA     TAG     TTT     GGA     AGG     TTA
    Leu     Lys     Glu     Asn     Leu     Lys     Ile     Ile     His     Arg     Asp     Ile     Lys     Pro     Ser     Asn>

635     640     645     650     655     660     665     670     675     680
     *               *               *               *               *
    ATT     CTT     CTG     GAC     AGA     AGT     GGA     AAT     ATT     AAG     CTC     TGT     GAC     TTC     GGC     ATC
    TAA     GAA     GAC     CTG     TCT     TCA     CCT     TTA     TAA     TTC     GAG     ACA     CTG     AAG     CCG     TAG
    Ile     Leu     Leu     Asp     Arg     Ser     Gly     Asn     Ile     Lys     Leu     Cys     Asp     Phe     Gly     Ile>

685     690     695     700     705     710     715     720     725
             *               *               *               *               *
    AGT     GGA     CAG     CTT     GTG     GAC     TCT     ATT     GCC     AAG     ACA     AGA     GAT     GCT     GGC     TGT
    TCA     CCT     GTC     GAA     CAC     CTG     AGA     TAA     CGG     TTC     TGT     TCT     CTA     CGA     CCG     ACA
    Ser     Gly     Gln     Leu     Val     Asp     Ser     Ile     Ala     Lys     Thr     Arg     Asp     Ala     Gly     Cys>

730     735     740     745     750     755     760     765     770     775
     *               *               *               *               *
    AGG     CCA     TAC     ATG     GCA     CCT     GAA     AGA     ATA     GAC     CCA     AGC     GCA     TCA     CGA     CAA
    TCC     GGT     ATG     TAC     CGT     GGA     CTT     TCT     TAT     CTG     GGT     TCG     CGT     AGT     GCT     GTT
    Arg     Pro     Tyr     Met     Ala     Pro     Glu     Arg     Ile     Asp     Pro     Ser     Ala     Ser     Arg     Gln>

780     785     790     795     800     805     810     815     820     825
             *               *               *               *               *
    GGA     TAT     GAT     GTC     CGC     TCT     GAT     GTC     TGG     AGT     TTG     GGG     ATC     ACA     TTG     TAT
    CCT     ATA     CTA     CAG     GCG     AGA     CTA     CAG     ACC     TCA     AAC     CCC     TAG     TGT     AAC     ATA
    Gly     Tyr     Asp     Val     Arg     Ser     Asp     Val     Trp     Ser     Leu     Gly     Ile     Thr     Leu     Tyr>

830     835     840     845     850     855     860     865     870
             *               *               *               *               *
    GAG     TTG     GCC     ACA     GGC     CGA     TTT     CCT     TAT     CCA     AAG     TGG     AAT     AGT     GTA     TTT
    CTC     AAC     CGG     TGT     CCG     GCT     AAA     GGA     ATA     GGT     TTC     ACC     TTA     TCA     CAT     AAA
    Glu     Leu     Ala     Thr     Gly     Arg     Phe     Pro     Tyr     Pro     Lys     Trp     Asn     Ser     Val     Phe>

875     880     885     890     895     900     905     910     915     920
     *               *               *               *               *
    GAT     CAA     CTA     ACA     CAA     GTC     GTG     AAA     GGA     GAT     CCT     CCG     CAG     CTG     AGT     AAT
    CTA     GTT     GAT     TGT     GTT     CAG     CAC     TTT     CCT     CTA     GGA     GGC     GTC     GAC     TCA     TTA
    Asp     Gln     Leu     Thr     Gln     Val     Val     Lys     Gly     Asp     Pro     Pro     Gln     Leu     Ser     Asn>

925     930     935     940     945     950     955     960     965
     *               *               *               *               *
    TCT     GAG     GAA     AGG     GAA     TTC     TCC     CCG     AGT     TTC     ATC     AAC     TTT     GTC     AAC     TTG
    AGA     CTC     CTT     TCC     CTT     AAG     AGG     GGC     TCA     AAG     TAG     TTG     AAA     CAG     TTG     AAC
    Ser     Glu     Glu     Arg     Glu     Phe     Ser     Pro     Ser     Phe     Ile     Asn     Phe     Val     Asn     Leu>

```
TGC CTT ACG AAG GAT GAA TCC AAA AGG CCA AAG TAT AAA GAG CTT CTG
ACG GAA TGC TTC CTA CTT AGG TTT TCC GGT TTC ATA TTT CTC GAA GAC
Cys Leu Thr Lys Asp Glu Ser Lys Arg Pro Lys Tyr Lys Glu Leu Leu>

1020    1025    1030 1035    1040    1045 1050    1055    1060 1065
      *       *       *           *       *            *       *
AAA CAT CCC TTT ATT TTG ATG TAT GAA GAA CGT GCC GTT GAG GTC GCA
TTT GTA GGG AAA TAA AAC TAC ATA CTT CTT GCA CGG CAA CTC CAG CGT
Lys His Pro Phe Ile Leu Met Tyr Glu Glu Arg Ala Val Glu Val Ala>

1070    1075 1080    1085    1090 1095    1100    1105  1110
       *           *        *            *       *             *
TGC TAT GTT TGT AAA ATC CTG GAT CAA ATG CCA GCT ACT CCC AGC TCT
ACG ATA CAA ACA TTT TAG GAC CTA GTT TAC GGT CGA TGA GGG TCG AGA
Cys Tyr Val Cys Lys Ile Leu Asp Gln Met Pro Ala Thr Pro Ser Ser>

1115    1120    1125    1130    1135 1140    1145 1150    1155 1160    1165 1170
  *       *       *       *             *            *             *           *
CCC ATG TAT GTC GAT TG ATATCGYTGC TACATCAGAC TCTAGAAAAA AGGGCTGAGA
GGG TAC ATA CAG CTA AC TATAGCRACG ATGTAGTCTG AGATCTTTTT TCCCGACTCT
Pro Met Tyr Val Asp>    (SEQ ID NO:6)

1175 1180    1185 1190    1195 1200    1205 1210    1215 1220    1225 1230
           *             *             *             *             *            *
GGAAGCAAGA CGTAAAGAAT TTTCATCCCG TATCACAGTG TTTTTATTGC TCGCCCAGAC
CCTTCGTTCT GCATTTCTTA AAAGTAGGGC ATAGTGTCAC AAAAATAACG AGCGGGTCTG 1235 1240    1245 1250    1255 1260    1265 1270    1275 1280    1285 1290
           *             *             *             *             *            *
ACCATGTGCA ATAAGATTGG TGTTCGTTTC CATCATGTCT GTATACTCCT GTCACCTAGA
TGGTACACGT TATTCTAACC ACAAGCAAAG GTAGTACAGA CATATGAGGA CAGTGGATCT 1295 1300    1305 1310    1315 1320    1325 1330    1335 1340    1345 1350
           *             *             *             *             *            *
ACGTGCATCC TTGTAATACC TGATTGATCA CACAGTGTTA GTGCTGGTCA GAGAGACCTC
TGCACGTAGG AACATTATGG ACTAACTAGT GTGTCACAAT CACGACCAGT CTCTCTGGAG 1355 1360    1365 1370    1375 1380    1385 1390    1395 1400    1405 1410
           *             *             *             *             *            *
ATCCTGCTCT TTTGTGATGA ACATATTCAT GAAATGTGGA AGTCAGTACG ATCAAGTTGT
TAGGACGAGA AAACACTACT TGTATAAGTA CTTTACACCT TCAGTCATGC TAGTTCAACA 1415 1420    1425 1430    1435 1440    1445 1450    1455 1460    1465 1470
           *             *             *             *             *            *
TGACTGTGAT TAGATCACAT CTTAAATTCA TTTCTAGACT CAAAACCTGG AGATGCAGCT
ACTGACACTA ATCTAGTGTA GAATTTAAGT AAAGATCTGA GTTTTGGACC TCTACGTCGA 1475 1480    1485 1490    1495 1500    1505 1510    1515 1520    1525 1530
           *             *             *             *             *            *
ACTGGAATGG TGTTTTGTCA GACTTCCAAA TCCTGGAAGG ACACAGTGAT GAATGTACTA
TGACCTTACC ACAAAACAGT CTGAAGGTTT AGGACCTTCC TGTGTCACTA CTTACATGAT 1535 1540    1545 1550    1555 1560    1565 1570    1575 1580    1585 1590
           *             *             *             *             *            *
TATCTGAACA TAGAAACTCG GGCTTGAGTG AGAAGAGCTT GCACAGCCAA CGAGACACAT
ATAGACTTGT ATCTTTGAGC CCGAACTCAC TCTTCTCGAA CGTGTCGGTT GCTCTGTGTA 1595 1600    1605 1610    1615 1620    1625 1630    1635 1640    1645 1650
           *             *             *             *             *            *
TGCCTTCTGG AGCTGGGAGA CAAAGGAGGA ATTTACTTTC TTCACCAAGT GCAATAGATT
ACGGAAGACC TCGACCCTCT GTTTCCTCCT TAAATGAAAG AAGTGGTTCA CGTTATCTAA
```

FIG. 6C

```
     1655 1660   1665 1670   1675 1680   1685 1690   1695 1700   1705 1710
        *           *           *           *           *           *
     ACTGATGTGA   TATTCTGTTG  CTTTACAGTT  ACAGTTGATG  TTTGGGGATC  GATGTGCTCA
     TGACTACACT   ATAAGACAAC  GAAATGTCAA  TGTCAACTAC  AAACCCCTAG  CTACACGAGT 1715 1720   1725 1730   1735 1740   1745 1750   1755 1760   1765 1770
        *           *           *           *           *           *
     GCCAAATTTC   CTGTTTGAAA  TATCATGTTA  AATTAGAATG  AATTTATCTT  TACCAAAAAC
     CGGTTTAAAG   GACAAACTTT  ATAGTACAAT  TTAATCTTAC  TTAAATAGAA  ATGGTTTTTG 1775 1780   1785 1790   1795 1800   1805 1810   1815 1820   1825 1830
        *           *           *           *           *           *
     CATGTTGCGT   TCAAAGAGGT  GAACATTAAA  ATATAGAGAC  AGGACAGAAT  GTGTTCTTTT
     GTACAACGCA   AGTTTCTCCA  CTTGTAATTT  TATATCTCTG  TCCTGTCTTA  CACAAGAAAA 1835 1840   1845 1850   1855 1860   1865 1870   1875 1880   1885 1890
        *           *           *           *           *           *
     CTCCTCTACC   AGTCCTATTT  TTCAATGGGA  AGACTCAGGA  GTCTGCCACT  TGTCAAAGAA
     GAGGAGATGG   TCAGGATAAA  AAGTTACCCT  TCTGAGTCCT  CAGACGGTGA  ACAGTTTCTT 1895 1900   1905 1910   1915 1920   1925 1930   1935 1940   1945 1950
        *           *           *           *           *           *
     GGTGCTGATC   CTAAGAATTT  TTCATTCTCA  GAATTCGGTG  TGCTGCCAAC  TTGATGTTCC
     CCACGACTAG   GATTCTTAAA  AAGTAAGAGT  CTTAAGCCAC  ACGACGGTTG  AACTACAAGG 1955 1960   1965 1970   1975 1980   1985 1990   1995 2000   2005 2010
        *           *           *           *           *           *
     ACCTGCCACA   AACCACCAGG  ACTGAAAGAA  GAAAACAGTA  CAGAAGGCAA  AGTTTACAGA
     TGGACGGTGT   TTGGTGGTCC  TGACTTTCTT  CTTTTGTCAT  GTCTTCCGTT  TCAAATGTCT 2015 2020   2025 2030   2035 2040   2045 2050   2055 2060   2065 2070
        *           *           *           *           *           *
     TGTTTTTAAT   TCTAGTATTT  TATCTGGAAC  AACTTGTAGC  AGCTATATAT  TTCCCCTTGG
     ACAAAAATTA   AGATCATAAA  ATAGACCTTG  TTGAACATCG  TCGATATATA  AAGGGGAACC 2075 2080   2085 2090   2095 2100   2105 2110   2115 2120   2125 2130
        *           *           *           *           *           *
     TCCCAAGCCT   GATACTTTAG  CCATCATAAC  TCACTAACAG  GGAGAAGTAG  CTAGTAGCAA
     AGGGTTCGGA   CTATGAAATC  GGTAGTATTG  AGTGATTGTC  CCTCTTCATC  GATCATCGTT 2135 2140   2145 2150   2155 2160   2165 2170   2175 2180   2185 2190
        *           *           *           *           *           *
     TGTGCCTTGA   TTGATTAGAT  AAAGATTTCT  AGTAGGCAGC  AAAAGACCAA  ATCTCAGTTG
     ACACGGAACT   AACTAATCTA  TTTCTAAAGA  TCATCCGTCG  TTTTCTGGTT  TAGAGTCAAC 2195 2200   2205 2210   2215 2220   2225 2230   2235 2240   2245 2250
        *           *           *           *           *           *
     TTTGCTTCTT   GCCATCACTG  GTCCAGGTCT  TCAGTTTCCG  AATCTCTTTC  CCTTCCCCTG
     AAACGAAGAA   CGGTAGTGAC  CAGGTCCAGA  AGTCAAAGGC  TTAGAGAAAG  GGAAGGGGAC 2255 2260   2265 2270   2275 2280   2285 2290   2295 2300   2305 2310
        *           *           *           *           *           *
     TGGTCTATTG   TCGCTATGTG  ACTTGCGCTT  AATCCAATAT  TTTGCCTTTT  TTCTATATCA
     ACCAGATAAC   AGCGATACAC  TGAACGCGAA  TTAGGTTATA  AAACGGAAAA  AAGATATAGT 2315 2320   2325 2330   2335 2340   2345 2350   2355 2360   2365 2370
        *           *           *           *           *           *
     AAAAACCTTT   ACAGTTAGCA  GGGATGTTCC  TTACCGAGGA  TTTTTAACCC  CCAATCTCTC
     TTTTTGGAAA   TGTCAATCGT  CCCTACAAGG  AATGGCTCCT  AAAAATTGGG  GGTTAGAGAG 2375 2380   2385 2390   2395 2400   2405 2410   2415 2420   2425 2430
        *           *           *           *           *           *
```

FIG. 6D

```
ATAATCGCTA GTGTTTAAAA GGCTAAGAAT AGTGGGGCCC AACCGATGTG GTAGGTGATA
TATTAGCGAT CACAAATTTT CCGATTCTTA TCACCCCGGG TTGGCTACAC CATCCACTAT 2435 2440  2445 2450  2455 2460  2465 2470  2475 2480  2485 2490
        *          *          *          *          *          *
AAGAGGCATC TTTTCTAGAG ACACATTGGA CCAGATGAGG ATCCGAAACG GCAGCCTTTA
TTCTCCGTAG AAAAGATCTC TGTGTAACCT GGTCTACTCC TAGGCTTTGC CGTCGGAAAT 2495 2500  2505 2510  2515 2520  2525 2530  2535 2540  2545 2550
        *          *          *          *          *          *
CGTTCATCAC CTGCTAGAAC CTCTCGTAGT CCATCACCAT TTCTTGGCAT TGGAATTCTA
GCAAGTAGTG GACGATCTTG GAGAGCATCA GGTAGTGGTA AAGAACCGTA ACCTTAAGAT 2555 2560  2565 2570  2575 2580  2585 2590  2595 2600  2605 2610
        *          *          *          *          *          *
CTGGAAAAAA ATACAAAAAG CAAAACAAAA CCCTCAGCAC TGTTACAAGA GGCCATTTAA
GACCTTTTTT TATGTTTTTC GTTTTGTTTT GGGAGTCGTG ACAATGTTCT CCGGTAAATT 2615 2620  2625 2630  2635 2640  2645 2650  2655 2660  2665 2670
        *          *          *          *          *          *
GTATCTTGTG CTTCTTCACT TACCCATTAG CCAGGTTCTC ATTAGGTTTT GCTTGGGCCT
CATAGAACAC GAAGAAGTGA ATGGGTAATC GGTCCAAGAG TAATCCAAAA CGAACCCGGA 2675 2680  2685 2690  2695 2700  2705 2710  2715 2720  2725 2730
        *          *          *          *          *          *
CCCTGGCACT GAACCTTAGG CTTTGTATGA CAGTGAAGCA GCACTGTGAG TGGTTCAAGC
GGGACCGTGA CTTGGAATCC GAAACATACT GTCACTTCGT CGTGACACTC ACCAAGTTCG 2735 2740  2745 2750  2755 2760  2765 2770  2775 2780  2785 2790
        *          *          *          *          *          *
ACACTGGAAT ATAAAACAGT CATGGCCTGA GATGCAGGTG ATGCCATTAC AGAACCAAAT
TGTGACCTTA TATTTTGTCA GTACCGGACT CTACGTCCAC TACGGTAATG TCTTGGTTTA 2795 2800  2805 2810  2815 2820  2825 2830  2835 2840  2845 2850
        *          *          *          *          *          *
CGTGGCACGT ATTGCTGTGT CTCCTCTCAG AGTGACAGTC ATAAATACTG TCAAACAATA
GCACCGTGCA TAACGACACA GAGGAGAGTC TCACTGTCAG TATTTATGAC AGTTTGTTAT 2855 2860  2865 2870  2875 2880  2885 2890  2895 2900  2905 2910
        *          *          *          *          *          *
AAGGGAGAAT GGTGCTGTTT AAAGTCACAT CCCTGTAAAT TGCAGAATTC AAAAGTGATT
TTCCCTCTTA CCACGACAAA TTTCAGTGTA GGGACATTTA ACGTCTTAAG TTTTCACTAA 2915 2920  2925 2930  2935 2940  2945 2950  2955 2960  2965 2970
        *          *          *          *          *          *
ATCTCTTTGA TCTACTTGCC TCATTTCCCT ATCTTCTCCC CCACGGTATC CTAAACTTTA
TAGAGAAACT AGATGAACGG AGTAAAGGGA TAGAAGAGGG GGTGCCATAG GATTTGAAAT 2975 2980  2985 2990  2995 3000  3005 3010  3015 3020  3025 3030
        *          *          *          *          *          *
GACTTCCCAC TGTTCTGAAA GGAGACATTG CTCTATGTCT GCCTTCGACC ACAGCAAGCC
CTGAAGGGTG ACAAGACTTT CCTCTGTAAC GAGATACAGA CGGAAGCTGG TGTCGTTCGG 3035 3040  3045 3050  3055 3060  3065 3070  3075 3080  3085 3090
        *          *          *          *          *          *
ATCATCCTCC ATTGCTCCCG GGGACTCAAG AGGAATCTGT TTCTCTGCTG TCAACTTCCC
TAGTAGGAGG TAACGAGGGC CCCTGAGTTC TCCTTAGACA AAGAGACGAC AGTTGAAGGG 3095 3100  3105 3110  3115 3120  3125 3130  3135 3140  3145 3150
        *          *          *          *          *          *
ATCTGGCTCA GCATAGGGTC ACTTTGCCAT TATGCAAATG GAGATAAAAG CAATTCTGGC
TAGACCGAGT CGTATCCCAG TGAAACGGTA ATACGTTTAC CTCTATTTTC GTTAAGACCG
```

FIG. 6E

```
    3155 3160   3165 3170   3175 3180   3185 3190   3195 3200   3205 3210
       *           *           *           *           *           *
    TGTCCAGGAG  CTAATCTGAC  CGTTCTATTG  TGTGGATGAC  CACATAAGAA  GGCAATTTTA
    ACAGGTCCTC  GATTAGACTG  GCAAGATAAC  ACACCTACTG  GTGTATTCTT  CCGTTAAAAT 3215 3220   3225 3230   3235 3240   3245 3250   3255 3260   3265 3270
       *           *           *           *           *           *
    GTGTATTAAT  CATAGATTAT  TATAAACTAT  AAACTTAAGG  GCAAGGAGTT  TATTACAATG
    CACATAATTA  GTATCTAATA  ATATTTGATA  TTTGAATTCC  CGTTCCTCAA  ATAATGTTAC 3275 3280   3285 3290   3295 3300   3305 3310   3315 3320   3325 3330
       *           *           *           *           *           *
    TATCTTTATT  AAAACAAAAG  GGTGTATAGT  GTTCACAAAC  TGTGAAAATA  GTGTAAGAAC
    ATAGAAATAA  TTTTGTTTTC  CCACATATCA  CAAGTGTTTG  ACACTTTTAT  CACATTCTTG 3335 3340   3345 3350   3355 3360   3365 3370   3375 3380   3385 3390
       *           *           *           *           *           *
    TGTACATTGT  GAGCTCTGGT  TATTTTTCTC  TTGTACCATA  GAAAAATGTA  TAAAAATTAT
    ACATGTAACA  CTCGAGACCA  ATAAAAGAG   AACATGGTAT  CTTTTTACAT  ATTTTTAATA 3395 3400   3405 3410   3415 3420   3425 3430   3435 3440   3445 3450
       *           *           *           *           *           *
    CAAAAAGCTA  ATGTGCAGGG  ATATTGCCTT  ATTTGTCTGT  AAAAAATGGA  GCTCAGTAAC
    GTTTTTCGAT  TACACGTCCC  TATAACGGAA  TAAACAGACA  TTTTTTACCT  CGAGTCATTG 3455 3460   3465 3470   3475 3480   3485 3490   3495
       *           *           *           *
    ATAACTGCTT  CTTGGAGCTT  TGGAATATTT  TATCCTGTAT  TCTTGTTT       (SEQ ID NO:5)
    TATTGACGAA  GAACCTCGAA  ACCTTATAAA  ATAGGACATA  AGAACAAA
```

FIG. 6F

```
              5         10        15        20        25        30        35        40        45       50
     CAACA ATG GCG GCT CCG AGC CCG AGC GGT GGC GGC GGC AGC GGC ACC CCC
     GTTGT TAC CGC CGA GGC TCG GGC TCG CCA CCG CCG CCG TCG CCG TGG GGG
           Met Ala Ala Pro Ser Pro Ser Gly Gly Gly Gly Ser Gly Thr Pro>

55        60        65        70        75        80        85        90        95
     GGC CCC GTA GGG TCC CCG GCG CCA GGC CAC CCG GCC GTC AGC AGC ATG
     CCG GGG CAT CCC AGG GGC CGC GGT CCG GTG GGC CGG CAG TCG TCG TAC
     Gly Pro Val Gly Ser Pro Ala Pro Gly His Pro Ala Val Ser Ser Met>

100       105       110       115       120       125       130       135       140       145
     CAG GGT AAA CGC AAA GCA CTG AAG TTG AAT TTT GCA AAT CCA CCT TTC
     GTC CCA TTT GCG TTT CGT GAC TTC AAC TTA AAA CGT TTA GGT GGA AAG
     Gln Gly Lys Arg Lys Ala Leu Lys Leu Asn Phe Ala Asn Pro Pro Phe>

150       155       160       165       170       175       180       185       190
     AAA TCT ACA GCA AGG TTT ACT CTG AAT CCC AAT CCT ACA GGA GTT CAA
     TTT AGA TGT CGT TCC AAA TGA GAC TTA GGG TTA GGA TGT CCT CAA GTT
     Lys Ser Thr Ala Arg Phe Thr Leu Asn Pro Asn Pro Thr Gly Val Gln>

195       200       205       210       215       220       225       230       235       240
     AAC CCA CAC ATA GAG AGA CTG AGA ACA CAC AGC ATT GAG TCA TCA GGA
     TTG GGT GTG TAT CTC TCT GAC TCT TGT GTG TCG TAA CTC AGT AGT CCT
     Asn Pro His Ile Glu Arg Leu Arg Thr His Ser Ile Glu Ser Ser Gly>

245       250       255       260       265       270       275       280       285       290
     AAA CTG AAG ATC TCC CCT GAA CAA CAC TGG GAT TTC ACT GCA GAG GAC
     TTT GAC TTC TAG AGG GGA CTT GTT GTG ACC CTA AAG TGA CGT CTC CTG
     Lys Leu Lys Ile Ser Pro Glu Gln His Trp Asp Phe Thr Ala Glu Asp>

295       300       305       310       315       320       325       330       335
     TTG AAA GAC CTT GGA GAA ATT GGA CGA GGA GCT TAT GGT TCT GTC AAC
     AAC TTT CTG GAA CCT CTT TAA CCT GCT CCT CGA ATA CCA AGA CAG TTG
     Leu Lys Asp Leu Gly Glu Ile Gly Arg Gly Ala Tyr Gly Ser Val Asn>

340       345       350       355       360       365       370       375       380       385
     AAA ATG GTC CAC AAA CCA AGT GGG CAA ATA ATG GCA GTT AAA AGA ATT
     TTT TAC CAG GTG TTT GGT TCA CCC GTT TAT TAC CGT CAA TTT TCT TAA
     Lys Met Val His Lys Pro Ser Gly Gln Ile Met Ala Val Lys Arg Ile>

390       395       400       405       410       415       420       425       430
     CGG TCA ACA GTG GAT GAA AAA GAA CAA AAA CAA CTT CTT ATG GAT TTG
     GCC AGT TGT CAC CTA CTT TTT CTT GTT TTT GTT GAA GAA TAC CTA AAC
     Arg Ser Thr Val Asp Glu Lys Glu Gln Lys Gln Leu Leu Met Asp Leu>

435       440       445       450       455       460       465       470       475       480
     GAT GTA GTA ATG CGG AGT AGT GAT TGC CCA TAC ATT GTT CAG TTT TAT
     CTA CAT CAT TAC GCC TCA TCA CTA ACG GGT ATG TAA CAA GTC AAA ATA
     Asp Val Val Met Arg Ser Ser Asp Cys Pro Tyr Ile Val Gln Phe Tyr>
```

FIG. 7A

```
      485       490       495       500       505       510       515       520       525       530
                 *                   *                   *                   *                   *
      GGT GCA CTC TTC AGA GAG GGT GAC TGT TGG ATC TGT ATG GAA CTC ATG
      CCA CGT GAG AAG TCT CTC CCA CTG ACA ACC TAG ACA TAC CTT GAG TAC
      Gly Ala Leu Phe Arg Glu Gly Asp Cys Trp Ile Cys Met Glu Leu Met>

535       540       545       550       555       560       565       570       575
                      *                   *                   *                   *
      TCT ACC TCG TTT GAT AAG TTT TAC AAA TAT GTA TAT AGT GTA TTA GAT
      AGA TGG AGC AAA CTA TTC AAA ATG TTT ATA CAT ATA TCA CAT AAT CTA
      Ser Thr Ser Phe Asp Lys Phe Tyr Lys Tyr Val Tyr Ser Val Leu Asp>

580       585       590       595       600       605       610       615       620       625
       *                   *                   *                   *                   *
      GAT GTT ATT CCA GAA GAA ATT TTA GGC AAA ATC ACT TTA GCA ACT GTG
      CTA CAA TAA GGT CTT CTT TAA AAT CCG TTT TAG TGA AAT CGT TGA CAC
      Asp Val Ile Pro Glu Glu Ile Leu Gly Lys Ile Thr Leu Ala Thr Val>

630       635       640       645       650       655       660       665       670
            *                   *                   *                   *                   *
      AAA GCA CTA AAC CAC TTA AAA GAA AAC TTG AAA ATT ATT CAC AGA GAT
      TTT CGT GAT TTG GTG AAT TTT CTT TTG AAC TTT TAA TAA GTG TCT CTA
      Lys Ala Leu Asn His Leu Lys Glu Asn Leu Lys Ile Ile His Arg Asp>

675       680       685       690       695       700       705       710       715       720
                 *                   *                   *                   *                   *
      ATC AAA CCT TCC AAT ATT CTT CTG GAC AGA AGT GGA AAT ATT AAG CTC
      TAG TTT GGA AGG TTA TAA GAA GAC CTG TCT TCA CCT TTA TAA TTC GAG
      Ile Lys Pro Ser Asn Ile Leu Leu Asp Arg Ser Gly Asn Ile Lys Leu>

725       730       735       740       745       750       755       760       765       770
                      *                   *                   *                   *                   *
      TGT GAC TTC GGC ATC AGT GGA CAG CTT GTG GAC TCT ATT GCC AAG ACA
      ACA CTG AAG CCG TAG TCA CCT GTC GAA CAC CTG AGA TAA CGG TTC TGT
      Cys Asp Phe Gly Ile Ser Gly Gln Leu Val Asp Ser Ile Ala Lys Thr>

775       780       785       790       795       800       805       810       815
                      *                   *                   *                   *
      AGA GAT GCT GGC TGT AGG CCA TAC ATG GCA CCT GAA AGA ATA GAC CCA
      TCT CTA CGA CCG ACA TCC GGT ATG TAC CGT GGA CTT TCT TAT CTG GGT
      Arg Asp Ala Gly Cys Arg Pro Tyr Met Ala Pro Glu Arg Ile Asp Pro>

820       825       830       835       840       845       850       855       860       865
       *                   *                   *                   *                   *
      AGC GCA TCA CGA CAA GGA TAT GAT GTC CGC TCT GAT GTC TGG AGT TTG
      TCG CGT AGT GCT GTT CCT ATA CTA CAG GCG AGA CTA CAG ACC TCA AAC
      Ser Ala Ser Arg Gln Gly Tyr Asp Val Arg Ser Asp Val Trp Ser Leu>

870       875       880       885       890       895       900       905       910
                      *                   *                   *                   *
      GGG ATC ACA TTG TAT GAG TTG GCC ACA GGC CGA TTT CCT TAT CCA AAG
      CCC TAG TGT AAC ATA CTC AAC CGG TGT CCG GCT AAA GGA ATA GGT TTC
      Gly Ile Thr Leu Tyr Glu Leu Ala Thr Gly Arg Phe Pro Tyr Pro Lys>

915       920       925       930       935       940       945       950       955       960
                 *                   *                   *                   *                   *
      TGG AAT AGT GTA TTT GAT CAA CTA ACA CAA GTC GTG AAA GGA GAT CCT
      ACC TTA TCA CAT AAA CTA GTT GAT TGT GTT CAG CAC TTT CCT CTA GGA
      Trp Asn Ser Val Phe Asp Gln Leu Thr Gln Val Val Lys Gly Asp Pro>

```
CCG CAG CTG AGT AAT TCT GAG GAA AGG GAA TTC TCC CCG AGT TTC ATC
GGC GTC GAC TCA TTA AGA CTC CTT TCC CTT AAG AGG GGC TCA AAG TAG
Pro Gln Leu Ser Asn Ser Glu Glu Arg Glu Phe Ser Pro Ser Phe Ile>

1015    1020   1025    1030    1035  1040    1045    1050  1055
                    *              *              *              *
AAC TTT GTC AAC TTG TGC CTT ACG AAG GAT GAA TCC AAA AGG CCA AAG
TTG AAA CAG TTG AAC ACG GAA TGC TTC CTA CTT AGG TTT TCC GGT TTC
Asn Phe Val Asn Leu Cys Leu Thr Lys Asp Glu Ser Lys Arg Pro Lys>

1060   1065   1070    1075    1080 1085    1090    1095 1100    1105
  *             *              *              *              *
TAT AAA GAG CTT CTG AAA CAT CCC TTT ATT TTG ATG TAT GAA GAA CGT
ATA TTT CTC GAA GAC TTT GTA GGG AAA TAA AAC TAC ATA CTT CTT GCA
Tyr Lys Glu Leu Leu Lys His Pro Phe Ile Leu Met Tyr Glu Glu Arg>

1110  1115    1120    1125 1130    1135    1140 1145    1150
            *              *              *              *
GCC GTT GAG GTC GCA TGC TAT GTT TGT AAA ATC CTG GAT CAA ATG CCA
CGG CAA CTC CAG CGT ACG ATA CAA ACA TTT TAG GAC CTA GTT TAC GGT
Ala Val Glu Val Ala Cys Tyr Val Cys Lys Ile Leu Asp Gln Met Pro>

1155 1160    1165    1170 1175    1180    1185 1190    1195 1200
       *              *              *              *
GCT ACT CCC AGC TCT CCC ATG TAT GTC GAT TGATAT CGYTGCTACA
CGA TGA GGG TCG AGA GGG TAC ATA CAG CTA ACTATA GCRACGATGT
Ala Thr Pro Ser Ser Pro Met Tyr Val Asp> (SEQ ID NO:8)

1205  1210   1215  1220   1225  1230   1235  1240   1245  1250   1255  1260
            *              *              *              *              *
       TCAGACTCTA GAAAAAAGGG CTGAGAGGAA GCAAGACGTA AAGAATTTTC ATCCCGTATC
       AGTCTGAGAT CTTTTTTCCC GACTCTCCTT CGTTCTGCAT TTCTTAAAAG TAGGGCATAG 1265  1270   1275  1280   1285  1290   1295  1300   1305  1310   1315  1320
            *              *              *              *              *
       ACAGTGTTTT TATTGCTCGC CCAGACACCA TGTGCAATAA GATTGGTGTT CGTTTCCATC
       TGTCACAAAA ATAACGAGCG GGTCTGTGGT ACACGTTATT CTAACCACAA GCAAAGGTAG 1325  1330   1335  1340   1345  1350   1355  1360   1365  1370   1375  1380
            *              *              *              *              *
       ATGTCTGTAT ACTCCTGTCA CCTAGAACGT GCATCCTTGT AATACCTGAT TGATCACACA
       TACAGACATA TGAGGACAGT GGATCTTGCA CGTAGGAACA TTATGGACTA ACTAGTGTGT 1385  1390   1395  1400   1405  1410   1415  1420   1425  1430   1435  1440
            *              *              *              *              *
       GTGTTAGTGC TGGTCAGAGA GACCTCATCC TGCTCTTTTG TGATGAACAT ATTCATGAAA
       CACAATCACG ACCAGTCTCT CTGGAGTAGG ACGAGAAAAC ACTACTTGTA TAAGTACTTT 1445  1450   1455  1460   1465  1470   1475  1480   1485  1490   1495  1500
            *              *              *              *              *
       TGTGGAAGTC AGTACGATCA AGTTGTTGAC TGTGATTAGA TCACATCTTA AATTCATTTC
       ACACCTTCAG TCATGCTAGT TCAACAACTG ACACTAATCT AGTGTAGAAT TTAAGTAAAG 1505  1510   1515  1520   1525  1530   1535  1540   1545  1550   1555  1560
            *              *              *              *              *
       TAGACTCAAA ACCTGGAGAT GCAGCTACTG GAATGGTGTT TTGTCAGACT TCCAAATCCT
       ATCTGAGTTT TGGACCTCTA CGTCGATGAC CTTACCACAA AACAGTCTGA AGGTTTAGGA 1565  1570   1575  1580   1585  1590   1595  1600   1605  1610   1615  1620
            *              *              *              *              *
       GGAAGGACAC AGTGATGAAT GTACTATATC TGAACATAGA AACTCGGGCT TGAGTGAGAA
       CCTTCCTGTG TCACTACTTA CATGATATAG ACTTGTATCT TTGAGCCCGA ACTCACTCTT
```

FIG. 7C

```
1625 1630   1635 1640   1645 1650   1655 1660   1665 1670   1675 1680
         *           *           *           *           *           *
GAGCTTGCAC  AGCCAACGAG  ACACATTGCC  TTCTGGAGCT  GGGAGACAAA  GGAGGAATTT
CTCGAACGTG  TCGGTTGCTC  TGTGTAACGG  AAGACCTCGA  CCCTCTGTTT  CCTCCTTAAA 1685 1690   1695 1700   1705 1710   1715 1720   1725 1730   1735 1740
         *           *           *           *           *           *
ACTTTCTTCA  CCAAGTGCAA  TAGATTACTG  ATGTGATATT  CTGTTGCTTT  ACAGTTACAG
TGAAAGAAGT  GGTTCACGTT  ATCTAATGAC  TACACTATAA  GACAACGAAA  TGTCAATGTC 1745 1750   1755 1760   1765 1770   1775 1780   1785 1790   1795 1800
         *           *           *           *           *           *
TTGATGTTTG  GGGATCGATG  TGCTCAGCCA  AATTTCCTGT  TTGAAATATC  ATGTTAAATT
AACTACAAAC  CCCTAGCTAC  ACGAGTCGGT  TTAAAGGACA  AACTTTATAG  TACAATTTAA 1805 1810   1815 1820   1825 1830   1835 1840   1845 1850   1855 1860
         *           *           *           *           *           *
AGAATGAATT  TATCTTTACC  AAAAACCATG  TTGCGTTCAA  AGAGGTGAAC  ATTAAAATAT
TCTTACTTAA  ATAGAAATGG  TTTTTGGTAC  AACGCAAGTT  TCTCCACTTG  TAATTTTATA 1865 1870   1875 1880   1885 1890   1895 1900   1905 1910   1915 1920
         *           *           *           *           *           *
AGAGACAGGA  CAGAATGTGT  TCTTTTCTCC  TCTACCAGTC  CTATTTTTCA  ATGGGAAGAC
TCTCTGTCCT  GTCTTACACA  AGAAAAGAGG  AGATGGTCAG  GATAAAAAGT  TACCCTTCTG 1925 1930   1935 1940   1945 1950   1955 1960   1965 1970   1975 1980
         *           *           *           *           *           *
TCAGGAGTCT  GCCACTTGTC  AAAGAAGGTG  CTGATCCTAA  GAATTTTTCA  TTCTCAGAAT
AGTCCTCAGA  CGGTGAACAG  TTTCTTCCAC  GACTAGGATT  CTTAAAAAGT  AAGAGTCTTA 1985 1990   1995 2000   2005 2010   2015 2020   2025 2030   2035 2040
         *           *           *           *           *           *
TCGGTGTGCT  GCCAACTTGA  TGTTCCACCT  GCCACAAACC  ACCAGGACTG  AAAGAAGAAA
AGCCACACGA  CGGTTGAACT  ACAAGGTGGA  CGGTGTTTGG  TGGTCCTGAC  TTTCTTCTTT 2045 2050   2055 2060   2065 2070   2075 2080   2085 2090   2095 2100
         *           *           *           *           *           *
ACAGTACAGA  AGGCAAAGTT  TACAGATGTT  TTTAATTCTA  GTATTTTATC  TGGAACAACT
TGTCATGTCT  TCCGTTTCAA  ATGTCTACAA  AAATTAAGAT  CATAAAATAG  ACCTTGTTGA 2105 2110   2115 2120   2125 2130   2135 2140   2145 2150   2155 2160
         *           *           *           *           *           *
TGTAGCAGCT  ATATATTTCC  CCTTGGTCCC  AAGCCTGATA  CTTTAGCCAT  CATAACTCAC
ACATCGTCGA  TATATAAAGG  GGAACCAGGG  TTCGGACTAT  GAAATCGGTA  GTATTGAGTG 2165 2170   2175 2180   2185 2190   2195 2200   2205 2210   2215 2220
         *           *           *           *           *           *
TAACAGGGAG  AAGTAGCTAG  TAGCAATGTG  CCTTGATTGA  TTAGATAAAG  ATTTCTAGTA
ATTGTCCCTC  TTCATCGATC  ATCGTTACAC  GGAACTAACT  AATCTATTTC  TAAAGATCAT 2225 2230   2235 2240   2245 2250   2255 2260   2265 2270   2275 2280
         *           *           *           *           *           *
GGCAGCAAAA  GACCAAATCT  CAGTTGTTTG  CTTCTTGCCA  TCACTGGTCC  AGGTCTTCAG
CCGTCGTTTT  CTGGTTTAGA  GTCAACAAAC  GAAGAACGGT  AGTGACCAGG  TCCAGAAGTC 2285 2290   2295 2300   2305 2310   2315 2320   2325 2330   2335 2340
         *           *           *           *           *           *
TTTCCGAATC  TCTTTCCCTT  CCCCTGTGGT  CTATTGTCGC  TATGTGACTT  GCGCTTAATC
AAAGGCTTAG  AGAAAGGGAA  GGGGACACCA  GATAACAGCG  ATACACTGAA  CGCGAATTAG 2345 2350   2355 2360   2365 2370   2375 2380   2385 2390   2395 2400
```

FIG. 7D

```
CAATATTTTG CCTTTTTTCT ATATCAAAAA ACCTTTACAG TTAGCAGGGA TGTTCCTTAC
GTTATAAAAC GGAAAAAAGA TATAGTTTTT TGGAAATGTC AATCGTCCCT ACAAGGAATG
    2405 2410  2415 2420  2425 2430  2435 2440  2445 2450  2455 2460

CGAGGATTTT TAACCCCCAA TCTCTCATAA TCGCTAGTGT TTAAAAGGCT AAGAATAGTG
GCTCCTAAAA ATTGGGGGTT AGAGAGTATT AGCGATCACA AATTTTCCGA TTCTTATCAC
    2465 2470  2475 2480  2485 2490  2495 2500  2505 2510  2515 2520

GGGCCCAACC GATGTGGTAG GTGATAAAGA GGCATCTTTT CTAGAGACAC ATTGGACCAG
CCCGGGTTGG CTACACCATC CACTATTTCT CCGTAGAAAA GATCTCTGTG TAACCTGGTC
    2525 2530  2535 2540  2545 2550  2555 2560  2565 2570  2575 2580

ATGAGGATCC GAAACGGCAG CCTTTACGTT CATCACCTGC TAGAACCTCT CGTAGTCCAT
TACTCCTAGG CTTTGCCGTC GGAAATGCAA GTAGTGGACG ATCTTGGAGA GCATCAGGTA
    2585 2590  2595 2600  2605 2610  2615 2620  2625 2630  2635 2640

CACCATTTCT TGGCATTGGA ATTCTACTGG AAAAAAATAC AAAAAGCAAA ACAAAACCCT
GTGGTAAAGA ACCGTAACCT TAAGATGACC TTTTTTTATG TTTTTCGTTT TGTTTTGGGA
    2645 2650  2655 2660  2665 2670  2675 2680  2685 2690  2695 2700

CAGCACTGTT ACAAGAGGCC ATTTAAGTAT CTTGTGCTTC TTCACTTACC CATTAGCCAG
GTCGTGACAA TGTTCTCCGG TAAATTCATA GAACACGAAG AAGTGAATGG GTAATCGGTC
    2705 2710  2715 2720  2725 2730  2735 2740  2745 2750  2755 2760

GTTCTCATTA GGTTTTGCTT GGGCCTCCCT GGCACTGAAC CTTAGGCTTT GTATGACAGT
CAAGAGTAAT CCAAAACGAA CCCGGAGGGA CCGTGACTTG GAATCCGAAA CATACTGTCA
    2765 2770  2775 2780  2785 2790  2795 2800  2805 2810  2815 2820

GAAGCAGCAC TGTGAGTGGT TCAAGCACAC TGGAATATAA AACAGTCATG GCCTGAGATG
CTTCGTCGTG ACACTCACCA AGTTCGTGTG ACCTTATATT TTGTCAGTAC CGGACTCTAC
    2825 2830  2835 2840  2845 2850  2855 2860  2865 2870  2875 2880

CAGGTGATGC CATTACAGAA CCAAATCGTG GCACGTATTG CTGTGTCTCC TCTCAGAGTG
GTCCACTACG GTAATGTCTT GGTTTAGCAC CGTGCATAAC GACACAGAGG AGAGTCTCAC
    2885 2890  2895 2900  2905 2910  2915 2920  2925 2930  2935 2940

ACAGTCATAA ATACTGTCAA ACAATAAAGG GAGAATGGTG CTGTTTAAAG TCACATCCCT
TGTCAGTATT TATGACAGTT TGTTATTTCC CTCTTACCAC GACAAATTTC AGTGTAGGGA
    2945 2950  2955 2960  2965 2970  2975 2980  2985 2990  2995 3000

GTAAATTGCA GAATTCAAAA GTGATTATCT CTTTGATCTA CTTGCCTCAT TTCCCTATCT
CATTTAACGT CTTAAGTTTT CACTAATAGA GAAACTAGAT GAACGGAGTA AAGGGATAGA
    3005 3010  3015 3020  3025 3030  3035 3040  3045 3050  3055 3060

TCTCCCCCAC GGTATCCTAA ACTTTAGACT TCCCACTGTT CTGAAAGGAG ACATTGCTCT
AGAGGGGGTG CCATAGGATT TGAAATCTGA AGGGTGACAA GACTTTCCTC TGTAACGAGA
    3065 3070  3075 3080  3085 3090  3095 3100  3105 3110  3115 3120

ATGTCTGCCT TCGACCACAG CAAGCCATCA TCCTCCATTG CTCCCGGGGA CTCAAGAGGA
```

FIG. 7E

```
          TACAGACGGA AGCTGGTGTC GTTCGGTAGT AGGAGGTAAC GAGGGCCCCT GAGTTCTCCT
          3125 3130  3135 3140  3145 3150  3155 3160  3165 3170  3175 3180
                  *          *          *          *          *          *
          ATCTGTTTCT CTGCTGTCAA CTTCCCATCT GGCTCAGCAT AGGGTCACTT TGCCATTATG
          TAGACAAAGA GACGACAGTT GAAGGGTAGA CCGAGTCGTA TCCCAGTGAA ACGGTAATAC
          3185 3190  3195 3200  3205 3210  3215 3220  3225 3230  3235 3240
                  *          *          *          *          *          *
          CAAATGGAGA TAAAAGCAAT TCTGGCTGTC CAGGAGCTAA TCTGACCGTT CTATTGTGTG
          GTTTACCTCT ATTTTCGTTA AGACCGACAG GTCCTCGATT AGACTGGCAA GATAACACAC
          3245 3250  3255 3260  3265 3270  3275 3280  3285 3290  3295 3300
                  *          *          *          *          *          *
          GATGACCACA TAAGAAGGCA ATTTTAGTGT ATTAATCATA GATTATTATA AACTATAAAC
          CTACTGGTGT ATTCTTCCGT TAAAATCACA TAATTAGTAT CTAATAATAT TTGATATTTG
          3305 3310  3315 3320  3325 3330  3335 3340  3345 3350  3355 3360
                  *          *          *          *          *          *
          TTAAGGGCAA GGAGTTTATT ACAATGTATC TTTATTAAAA CAAAAGGGTG TATAGTGTTC
          AATTCCCGTT CCTCAAATAA TGTTACATAG AAATAATTTT GTTTTCCCAC ATATCACAAG
          3365 3370  3375 3380  3385 3390  3395 3400  3405 3410  3415 3420
                  *          *          *          *          *          *
          ACAAACTGTG AAAATAGTGT AAGAACTGTA CATTGTGAGC TCTGGTTATT TTTCTCTTGT
          TGTTTGACAC TTTTATCACA TTCTTGACAT GTAACACTCG AGACCAATAA AAAGAGAACA
          3425 3430  3435 3440  3445 3450  3455 3460  3465 3470  3475 3480
                  *          *          *          *          *          *
          ACCATAGAAA AATGTATAAA AATTATCAAA AAGCTAATGT GCAGGGATAT TGCCTTATTT
          TGGTATCTTT TTACATATTT TTAATAGTTT TTCGATTACA CGTCCCTATA ACGGAATAAA
          3485 3490  3495 3500  3505 3510  3515 3520  3525 3530  3535 3540
                  *          *          *          *          *          *
          GTCTGTAAAA AATGGAGCTC AGTAACATAA CTGCTTCTTG GAGCTTTGGA ATATTTTATC
          CAGACATTTT TTACCTCGAG TCATTGTATT GACGAAGAAC CTCGAAACCT TATAAAATAG
          3545 3550
                  *
          CTGTATTCTT GTTT     (SEQ ID NO:7)
          GACATAAGAA CAAA
```

FIG. 7F

```
           5        10        15        20        25        30        35        40        45        50
           *                            *                             *                              *
       CTCCCAACA ATG GCG GCT CCG AGC CCG AGC GGC GGC GGC GGC TCC GGG GGC
       GAGGGTTGT TAC CGC CGA GGC TCG GGC TCG CCG CCG CCG CCG AGG CCC CCG
                 Met Ala Ala Pro Ser Pro Ser Gly Gly Gly Gly Ser Gly Gly>

55        60        65        70        75        80        85        90        95
                 *                            *                             *                    *
            GGC AGC GGC AGC GGC ACC CCC GGC CCC GTA GGG TCC CCG GCG CCA GGC
            CCG TCG CCG TCG CCG TGG GGG CCG GGG CAT CCC AGG GGC CGC GGT CCG
            Gly Ser Gly Ser Gly Thr Pro Gly Pro Val Gly Ser Pro Ala Pro Gly>

100      105      110      115      120      125      130      135      140      145
          *                  *                  *                 *                    *
       CAC CCG GCC GTC AGC AGC ATG CAG GGT AAA CGC AAA GCA CTG AAG TTG
       GTG GGC CGG CAG TCG TCG TAC GTC CCA TTT GCG TTT CGT GAC TTC AAC
       His Pro Ala Val Ser Ser Met Gln Gly Lys Arg Lys Ala Leu Lys Leu>

150      155      160      165      170      175      180      185      190      195
          *                  *                  *                 *                    *
       AAT TTT GCA AAT CCA CCT TTC AAA TCT ACA GCA AGG TTT ACT CTG AAT
       TTA AAA CGT TTA GGT GGA AAG TTT AGA TGT CGT TCC AAA TGA GAC TTA
       Asn Phe Ala Asn Pro Pro Phe Lys Ser Thr Ala Arg Phe Thr Leu Asn>

200      205      210      215      220      225      230      235      240
          *                  *                  *                 *                 *
       CCC AAT CCT ACA GGA GTT CAA AAC CCA CAC ATA GAG AGA CTG AGA ACA
       GGG TTA GGA TGT CCT CAA GTT TTG GGT GTG TAT CTC TCT GAC TCT TGT
       Pro Asn Pro Thr Gly Val Gln Asn Pro His Ile Glu Arg Leu Arg Thr>

245      250      255      260      265      270      275      280      285      290
          *                  *                  *                 *                    *
       CAC AGC ATT GAG TCA TCA GGA AAA CTG AAG ATC TCC CCT GAA CAA CAC
       GTG TCG TAA CTC AGT AGT CCT TTT GAC TTC TAG AGG GGA CTT GTT GTG
       His Ser Ile Glu Ser Ser Gly Lys Leu Lys Ile Ser Pro Glu Gln His>

295      300      305      310      315      320      325      330      335
          *                  *                  *                 *              *
       TGG GAT TTC ACT GCA GAG GAC TTG AAA GAC CTT GGA GAA ATT GGA CGA
       ACC CTA AAG TGA CGT CTC CTG AAC TTT CTG GAA CCT CTT TAA CCT GCT
       Trp Asp Phe Thr Ala Glu Asp Leu Lys Asp Leu Gly Glu Ile Gly Arg>

340      345      350      355      360      365      370      375      380      385
          *                  *                  *                 *                    *
       GGA GCT TAT GGT TCT GTC AAC AAA ATG GTC CAC AAA CCA AGT GGG CAA
       CCT CGA ATA CCA AGA CAG TTG TTT TAC CAG GTG TTT GGT TCA CCC GTT
       Gly Ala Tyr Gly Ser Val Asn Lys Met Val His Lys Pro Ser Gly Gln>

390      395      400      405      410      415      420      425      430      435
          *                  *                  *                 *                    *
       ATA ATG GCA GTT AAA AGA ATT CGG TCA ACA GTG GAT GAA AAA GAA CAA
       TAT TAC CGT CAA TTT TCT TAA GCC AGT TGT CAC CTA CTT TTT CTT GTT
       Ile Met Ala Val Lys Arg Ile Arg Ser Thr Val Asp Glu Lys Glu Gln>

440      445      450      455      460      465      470      475      480
          *                  *                  *                 *                 *
       AAA CAA CTT CTT ATG GAT TTG GAT GTA GTA ATG CGG AGT AGT GAT TGC
       TTT GTT GAA GAA TAC CTA AAC CTA CAT CAT TAC GCC TCA TCA CTA ACG
       Lys Gln Leu Leu Met Asp Leu Asp Val Val Met Arg Ser Ser Asp Cys>
```

FIG. 8A

```
      485       490       495       500       505       510       515       520       525       530
       *                   *                   *                   *                   *
      CCA TAC ATT GTT CAG TTT TAT GGT GCA CTC TTC AGA GAG GGT GAC TGT
      GGT ATG TAA CAA GTC AAA ATA CCA CGT GAG AAG TCT CTC CCA CTG ACA
      Pro Tyr Ile Val Gln Phe Tyr Gly Ala Leu Phe Arg Glu Gly Asp Cys>

535       540       545       550       555       560       565       570       575
                     *                   *                   *                   *
          TGG ATC TGT ATG GAA CTC ATG TCT ACC TCG TTT GAT AAG TTT TAC AAA
          ACC TAG ACA TAC CTT GAG TAC AGA TGG AGC AAA CTA TTC AAA ATG TTT
          Trp Ile Cys Met Glu Leu Met Ser Thr Ser Phe Asp Lys Phe Tyr Lys>

580       585       590       595       600       605       610       615       620       625
  *                   *                   *                   *                   *
 TAT GTA TAT AGT GTA TTA GAT GAT GTT ATT CCA GAA GAA ATT TTA GGC
 ATA CAT ATA TCA CAT AAT CTA CTA CAA TAA GGT CTT CTT TAA AAT CCG
 Tyr Val Tyr Ser Val Leu Asp Asp Val Ile Pro Glu Glu Ile Leu Gly>

630       635       640       645       650       655       660       665       670       675
       *                   *                   *                   *                   *
      AAA ATC ACT TTA GCA ACT GTG AAA GCA CTA AAC CAC TTA AAA GAA AAC
      TTT TAG TGA AAT CGT TGA CAC TTT CGT GAT TTG GTG AAT TTT CTT TTG
      Lys Ile Thr Leu Ala Thr Val Lys Ala Leu Asn His Leu Lys Glu Asn>

680       685       690       695       700       705       710       715       720
                     *                   *                   *                   *
          TTG AAA ATT ATT CAC AGA GAT ATC AAA CCT TCC AAT ATT CTT CTG GAC
          AAC TTT TAA TAA GTG TCT CTA TAG TTT GGA AGG TTA TAA GAA GAC CTG
          Leu Lys Ile Ile His Arg Asp Ile Lys Pro Ser Asn Ile Leu Leu Asp>

725       730       735       740       745       750       755       760       765       770
  *                   *                   *                   *                   *
 AGA AGT GGA AAT ATT AAG CTC TGT GAC TTC GGC ATC AGT GGA CAG CTT
 TCT TCA CCT TTA TAA TTC GAG ACA CTG AAG CCG TAG TCA CCT GTC GAA
 Arg Ser Gly Asn Ile Lys Leu Cys Asp Phe Gly Ile Ser Gly Gln Leu>

775       780       785       790       795       800       805       810       815
       *                   *                   *                   *                   *
      GTG GAC TCT ATT GCC AAG ACA AGA GAT GCT GGC TGT AGG CCA TAC ATG
      CAC CTG AGA TAA CGG TTC TGT TCT CTA CGA CCG ACA TCC GGT ATG TAC
      Val Asp Ser Ile Ala Lys Thr Arg Asp Ala Gly Cys Arg Pro Tyr Met>

820       825       830       835       840       845       850       855       860       865
  *                   *                   *                   *                   *
 GCA CCT GAA AGA ATA GAC CCA AGC GCA TCA CGA CAA GGA TAT GAT GTC
 CGT GGA CTT TCT TAT CTG GGT TCG CGT AGT GCT GTT CCT ATA CTA CAG
 Ala Pro Glu Arg Ile Asp Pro Ser Ala Ser Arg Gln Gly Tyr Asp Val>

870       875       880       885       890       895       900       905       910       915
       *                   *                   *                   *                   *
      CGC TCT GAT GTC TGG AGT TTG GGG ATC ACA TTG TAT GAG TTG GCC ACA
      GCG AGA CTA CAG ACC TCA AAC CCC TAG TGT AAC ATA CTC AAC CGG TGT
      Arg Ser Asp Val Trp Ser Leu Gly Ile Thr Leu Tyr Glu Leu Ala Thr>

920       925       930       935       940       945       950       955       960
                     *                   *                   *                   *
          GGC CGA TTT CCT TAT CCA AAG TGG AAT AGT GTA TTT GAT CAA CTA ACA
          CCG GCT AAA GGA ATA GGT TTC ACC TTA TCA CAT AAA CTA GTT GAT TGT
          Gly Arg Phe Pro Tyr Pro Lys Trp Asn Ser Val Phe Asp Gln Leu Thr>

```
CAA GTC GTG AAA GGA GAT CCT CCG CAG CTG AGT AAT TCT GAG GAA AGG
GTT CAG CAC TTT CCT CTA GGA GGC GTC GAC TCA TTA AGA CTC CTT TCC
Gln Val Val Lys Gly Asp Pro Pro Gln Leu Ser Asn Ser Glu Glu Arg>

1015 1020  1025  1030  1035  1040  1045 1050  1055
                  *           *           *           *
GAA TTC TCC CCG AGT TTC ATC AAC TTT GTC AAC TTG TGC CTT ACG AAG
CTT AAG AGG GGC TCA AAG TAG TTG AAA CAG TTG AAC ACG GAA TGC TTC
Glu Phe Ser Pro Ser Phe Ile Asn Phe Val Asn Leu Cys Leu Thr Lys>

1060 1065  1070  1075 1080  1085  1090  1095  1100   1105
   *           *          *           *          *
GAT GAA TCC AAA AGG CCA AAG TAT AAA GAG CTT CTG AAA CAT CCC TTT
CTA CTT AGG TTT TCC GGT TTC ATA TTT CTC GAA GAC TTT GTA GGG AAA
Asp Glu Ser Lys Arg Pro Lys Tyr Lys Glu Leu Leu Lys His Pro Phe>

1110    1115   1120  1125  1130   1135  1140   1145  1150  1155
    *           *          *           *           *
ATT TTG ATG TAT GAA GAA CGT GCC GTT GAG GTC GCA TGC TAT GTT TGT
TAA AAC TAC ATA CTT CTT GCA CGG CAA CTC CAG CGT ACG ATA CAA ACA
Ile Leu Met Tyr Glu Glu Arg Ala Val Glu Val Ala Cys Tyr Val Cys>

1160    1165   1170   1175   1180   1185   1190   1195  1200
         *           *           *          *           *           *
AAA ATC CTG GAT CAA ATG CCA GCT ACT CCC AGC TCT CCC ATG TAT GTC
TTT TAG GAC CTA GTT TAC GGT CGA TGA GGG TCG AGA GGG TAC ATA CAG
Lys Ile Leu Asp Gln Met Pro Ala Thr Pro Ser Ser Pro Met Tyr Val>

1205  1210   1215 1220   1225 1230   1235 1240   1245 1250   1255 1260
    *            *            *            *            *            *
GAT TGAT ATCGCTGCTA CATCAGACTC TAGAAAAAAG GGCTGAGAGG AAGCAAGACG
CTA ACTA TAGCGACGAT GTAGTCTGAG ATCTTTTTTC CCGACTCTCC TTCGTTCTGC
Asp>  (SEQ ID NO:10)

1265 1270  1275 1280  1285 1290  1295 1300  1305 1310  1315 1320
     *           *           *            *           *           *
TAAAGAATTT TCATCCCGTA TCACAGTGTT TTTATTGCTC GCCCAGACAC CATGTGCAAT
ATTTCTTAAA AGTAGGGCAT AGTGTCACAA AAATAACGAG CGGGTCTGTG GTACACGTTA 1325 1330  1335 1340  1345 1350  1355 1360  1365 1370  1375 1380
      *            *           *           *           *           *
AAGATTGGTG TTCGTTTCCA TCATGTCTGT ATACTCCTGT CACCTAGAAC GTGCATCCTT
TTCTAACCAC AAGCAAAGGT AGTACAGACA TATGAGGACA GTGGATCTTG CACGTAGGAA 1385 1390  1395 1400  1405 1410  1415 1420  1425 1430  1435 1440
      *           *           *           *           *           *
GTAATACCTG ATTGATCACA CAGTGTTAGT GCTGGTCAGA GAGACCTCAT CCTGCTCTTT
CATTATGGAC TAACTAGTGT GTCACAATCA CGACCAGTCT CTCTGGAGTA GGACGAGAAA 1445 1450  1455 1460  1465 1470  1475 1480  1485 1490  1495 1500
      *           *           *           *           *           *
TGTGATGAAC ATATTCATGA AATGTGGAAG TCAGTACGAT CAAGTTGTTG ACTGTGATTA
ACACTACTTG TATAAGTACT TTACACCTTC AGTCATGCTA GTTCAACAAC TGACACTAAT 1505 1510  1515 1520  1525 1530  1535 1540  1545 1550  1555 1560
      *           *           *           *           *           *
GATCACATCT TAAATTCATT TCTAGACTCA AAACCTGGAG ATGCAGCTAC TGGAATGGTG
CTAGTGTAGA ATTTAAGTAA AGATCTGAGT TTTGGACCTC TACGTCGATG ACCTTACCAC 1565 1570  1575 1580  1585 1590  1595 1600  1605 1610  1615 1620
      *           *           *           *           *           *
TTTTGTCAGA CTTCCAAATC CTGGAAGGAC ACAGTGATGA ATGTACTATA TCTGAACATA
```

FIG. 8C

```
AAAACAGTCT GAAGGTTTAG GACCTTCCTG TGTCACTACT TACATGATAT AGACTTGTAT
1625 1630  1635 1640  1645 1650  1655 1660  1665 1670  1675 1680
     *          *          *          *          *          *
GAAACTCGGG CTTGAGTGAG AAGAGCTTGC ACAGCCAACG AGACACATTG CCTTCTGGAG
CTTTGAGCCC GAACTCACTC TTCTCGAACG TGTCGGTTGC TCTGTGTAAC GGAAGACCTC 1685 1690  1695 1700  1705 1710  1715 1720  1725 1730  1735 1740
     *          *          *          *          *          *
CTGGGAGACA AAGGAGGAAT TTACTTTCTT CACCAAGTGC AATAGATTAC TGATGTGATA
GACCCTCTGT TTCCTCCTTA AATGAAAGAA GTGGTTCACG TTATCTAATG ACTACACTAT 1745 1750  1755 1760  1765 1770  1775 1780  1785 1790  1795 1800
     *          *          *          *          *          *
TTCTGTTGCT TTACAGTTAC AGTTGATGTT TGGGGATCGA TGTGCTCAGC CAAATTTCCT
AAGACAACGA AATGTCAATG TCAACTACAA ACCCCTAGCT ACACGAGTCG GTTTAAAGGA 1805 1810  1815 1820  1825 1830  1835 1840  1845 1850  1855 1860
     *          *          *          *          *          *
GTTTGAAATA TCATGTTAAA TTAGAATGAA TTTATCTTTA CCAAAAACCA TGTTGCGTTC
CAAACTTTAT AGTACAATTT AATCTTACTT AAATAGAAAT GGTTTTTGGT ACAACGCAAG 1865 1870  1875 1880  1885 1890  1895 1900  1905 1910  1915 1920
     *          *          *          *          *          *
AAAGAGGTGA ACATTAAAAT ATAGAGACAG GACAGAATGT GTTCTTTTCT CCTCTACCAG
TTTCTCCACT TGTAATTTTA TATCTCTGTC CTGTCTTACA CAAGAAAAGA GGAGATGGTC 1925 1930  1935 1940  1945 1950  1955 1960  1965 1970  1975 1980
     *          *          *          *          *          *
TCCTATTTTT CAATGGAAG ACTCAGGAGT CTGCCACTTG TCAAAGAAGG TGCTGATCCT
AGGATAAAAA GTTACCCTTC TGAGTCCTCA GACGGTGAAC AGTTTCTTCC ACGACTAGGA 1985 1990  1995 2000  2005 2010  2015 2020  2025 2030  2035 2040
     *          *          *          *          *          *
AAGAATTTTT CATTCTCAGA ATTCGGTGTG CTGCCAACTT GATGTTCCAC CTGCCACAAA
TTCTTAAAAA GTAAGAGTCT TAAGCCACAC GACGGTTGAA CTACAAGGTG GACGGTGTTT 2045 2050  2055 2060  2065 2070  2075 2080  2085 2090  2095 2100
     *          *          *          *          *          *
CCACCAGGAC TGAAAGAAGA AAACAGTACA GAAGGCAAAG TTTACAGATG TTTTTAATTC
GGTGGTCCTG ACTTTCTTCT TTTGTCATGT CTTCCGTTTC AAATGTCTAC AAAAATTAAG 2105 2110  2115 2120  2125 2130  2135 2140  2145 2150  2155 2160
     *          *          *          *          *          *
TAGTATTTTA TCTGGAACAA CTTGTAGCAG CTATATATTT CCCCTTGGTC CCAAGCCTGA
ATCATAAAAT AGACCTTGTT GAACATCGTC GATATATAAA GGGGAACCAG GGTTCGGACT 2165 2170  2175 2180  2185 2190  2195 2200  2205 2210  2215 2220
     *          *          *          *          *          *
TACTTTAGCC ATCATAACTC ACTAACAGGG AGAAGTAGCT AGTAGCAATG TGCCTTGATT
ATGAAATCGG TAGTATTGAG TGATTGTCCC TCTTCATCGA TCATCGTTAC ACGGAACTAA 2225 2230  2235 2240  2245 2250  2255 2260  2265 2270  2275 2280
     *          *          *          *          *          *
GATTAGATAA AGATTTCTAG TAGGCAGCAA AAGACCAAAT CTCAGTTGTT TGCTTCTTGC
CTAATCTATT TCTAAAGATC ATCCGTCGTT TTCTGGTTTA GAGTCAACAA ACGAAGAACG 2285 2290  2295 2300  2305 2310  2315 2320  2325 2330  2335 2340
     *          *          *          *          *          *
CATCACTGGT CCAGGTCTTC AGTTTCCGAA TCTCTTTCCC TTCCCTGTG GTCTATTGTC
GTAGTGACCA GGTCCAGAAG TCAAAGGCTT AGAGAAAGGG AAGGGACAC CAGATAACAG
```

FIG. 8D

```
       2345 2350   2355 2360   2365 2370   2375 2380   2385 2390   2395 2400
            *           *           *           *           *           *
       GCTATGTGAC  TTGCGCTTAA  TCCAATATTT  TGCCTTTTTT  CTATATCAAA  AAACCTTTAC
       CGATACACTG  AACGCGAATT  AGGTTATAAA  ACGGAAAAAA  GATATAGTTT  TTTGGAAATG 2405 2410   2415 2420   2425 2430   2435 2440   2445 2450   2455 2460
            *           *           *           *           *           *
       AGTTAGCAGG  GATGTTCCTT  ACCGAGGATT  TTTAACCCCC  AATCTCTCAT  AATCGCTAGT
       TCAATCGTCC  CTACAAGGAA  TGGCTCCTAA  AAATTGGGGG  TTAGAGAGTA  TTAGCGATCA 2465 2470   2475 2480   2485 2490   2495 2500   2505 2510   2515 2520
            *           *           *           *           *           *
       GTTTAAAAGG  CTAAGAATAG  TGGGGCCCAA  CCGATGTGGT  AGGTGATAAA  GAGGCATCTT
       CAAATTTTCC  GATTCTTATC  ACCCCGGGTT  GGCTACACCA  TCCACTATTT  CTCCGTAGAA 2525 2530   2535 2540   2545 2550   2555 2560   2565 2570   2575 2580
            *           *           *           *           *           *
       TTCTAGAGAC  ACATTGGACC  AGATGAGGAT  CCGAAACGGC  AGCCTTTACG  TTCATCACCT
       AAGATCTCTG  TGTAACCTGG  TCTACTCCTA  GGCTTTGCCG  TCGGAAATGC  AAGTAGTGGA 2585 2590   2595 2600   2605 2610   2615 2620   2625 2630   2635 2640
            *           *           *           *           *           *
       GCTAGAACCT  CTCGTAGTCC  ATCACCATTT  CTTGGCATTG  GAATTCTACT  GGAAAAAAAT
       CGATCTTGGA  GAGCATCAGG  TAGTGGTAAA  GAACCGTAAC  CTTAAGATGA  CCTTTTTTTA 2645 2650   2655 2660   2665 2670   2675 2680   2685 2690   2695 2700
            *           *           *           *           *           *
       ACAAAAAGCA  AAACAAAACC  CTCAGCACTG  TTACAAGAGG  CCATTTAAGT  ATCTTGTGCT
       TGTTTTTCGT  TTTGTTTTGG  GAGTCGTGAC  AATGTTCTCC  GGTAAATTCA  TAGAACACGA 2705 2710   2715 2720   2725 2730   2735 2740   2745 2750   2755 2760
            *           *           *           *           *           *
       TCTTCACTTA  CCCATTAGCC  AGGTTCTCAT  TAGGTTTTGC  TTGGGCCTCC  CTGGCACTGA
       AGAAGTGAAT  GGGTAATCGG  TCCAAGAGTA  ATCCAAAACG  AACCCGGAGG  GACCGTGACT 2765 2770   2775 2780   2785 2790   2795 2800   2805 2810   2815 2820
            *           *           *           *           *           *
       ACCTTAGGCT  TTGTATGACA  GTGAAGCAGC  ACTGTGAGTG  GTTCAAGCAC  ACTGGAATAT
       TGGAATCCGA  AACATACTGT  CACTTCGTCG  TGACACTCAC  CAAGTTCGTG  TGACCTTATA 2825 2830   2835 2840   2845 2850   2855 2860   2865 2870   2875 2880
            *           *           *           *           *           *
       AAAACAGTCA  TGGCCTGAGA  TGCAGGTGAT  GCCATTACAG  AACCAAATCG  TGGCACGTAT
       TTTTGTCAGT  ACCGGACTCT  ACGTCCACTA  CGGTAATGTC  TTGGTTTAGC  ACCGTGCATA 2885 2890   2895 2900   2905 2910   2915 2920   2925 2930   2935 2940
            *           *           *           *           *           *
       TGCTGTGTCT  CCTCTCAGAG  TGACAGTCAT  AAATACTGTC  AAACAATAAA  GGGAGAATGG
       ACGACACAGA  GGAGAGTCTC  ACTGTCAGTA  TTTATGACAG  TTTGTTATTT  CCCTCTTACC 2945 2950   2955 2960   2965 2970   2975 2980   2985 2990   2995 3000
            *           *           *           *           *           *
       TGCTGTTTAA  AGTCACATCC  CTGTAAATTG  CAGAATTCAA  AAGTGATTAT  CTCTTTGATC
       ACGACAAATT  TCAGTGTAGG  GACATTTAAC  GTCTTAAGTT  TTCACTAATA  GAGAAACTAG 3005 3010   3015 3020   3025 3030   3035 3040   3045 3050   3055 3060
            *           *           *           *           *           *
       TACTTGCCTC  ATTTCCCTAT  CTTCTCCCCC  ACGGTATCCT  AAACTTTAGA  CTTCCCACTG
       ATGAACGGAG  TAAAGGGATA  GAAGAGGGGG  TGCCATAGGA  TTTGAAATCT  GAAGGGTGAC 3065 3070   3075 3080   3085 3090   3095 3100   3105 3110   3115 3120
            *           *           *           *           *           *
```

FIG. 8E

```
TTCTGAAAGG AGACATTGCT CTATGTCTGC CTTCGACCAC AGCAAGCCAT CATCCTCCAT
AAGACTTTCC TCTGTAACGA GATACAGACG GAAGCTGGTG TCGTTCGGTA GTAGGAGGTA 3125 3130  3135 3140  3145 3150  3155 3160  3165 3170  3175 3180
              *         *         *         *         *         *
TGCTCCCGGG GACTCAAGAG GAATCTGTTT CTCTGCTGTC AACTTCCCAT CTGGCTCAGC
ACGAGGGCCC CTGAGTTCTC CTTAGACAAA GAGACGACAG TTGAAGGGTA GACCGAGTCG 3185 3190  3195 3200  3205 3210  3215 3220  3225 3230  3235 3240
              *         *         *         *         *         *
ATAGGGTCAC TTTGCCATTA TGCAAATGGA GATAAAAGCA ATTCTGGCTG TCCAGGAGCT
TATCCCAGTG AAACGGTAAT ACGTTTACCT CTATTTTCGT TAAGACCGAC AGGTCCTCGA 3245 3250  3255 3260  3265 3270  3275 3280  3285 3290  3295 3300
              *         *         *         *         *         *
AATCTGACCG TTCTATTGTG TGGATGACCA CATAAGAAGG CAATTTTAGT GTATTAATCA
TTAGACTGGC AAGATAACAC ACCTACTGGT GTATTCTTCC GTTAAAATCA CATAATTAGT 3305 3310  3315 3320  3325 3330  3335 3340  3345 3350  3355 3360
              *         *         *         *         *         *
TAGATTATTA TAAACTATAA ACTTAAGGGC AAGGAGTTTA TTACAATGTA TCTTTATTAA
ATCTAATAAT ATTTGATATT TGAATTCCCG TTCCTCAAAT AATGTTACAT AGAAATAATT 3365 3370  3375 3380  3385 3390  3395 3400  3405 3410  3415 3420
              *         *         *         *         *         *
AACAAAAGGG TGTATAGTGT TCACAAACTG TGAAAATAGT GTAAGAACTG TACATTGTGA
TTGTTTTCCC ACATATCACA AGTGTTTGAC ACTTTTATCA CATTCTTGAC ATGTAACACT 3425 3430  3435 3440  3445 3450  3455 3460  3465 3470  3475 3480
              *         *         *         *         *         *
GCTCTGGTTA TTTTTCTCTT GTACCATAGA AAAATGTATA AAAATTATCA AAAAGCTAAT
CGAGACCAAT AAAAAGAGAA CATGGTATCT TTTTACATAT TTTTAATAGT TTTTCGATTA 3485 3490  3495 3500  3505 3510  3515 3520  3525 3530  3535 3540
              *         *         *         *         *         *
GTGCAGGGAT ATTGCCTTAT TTGTCTGTAA AAAATGGAGC TCAGTAACAT AACTGCTTCT
CACGTCCCTA TAACGGAATA AACAGACATT TTTTACCTCG AGTCATTGTA TTGACGAAGA 3545 3550  3555 3560  3565 3570  3575
              *         *         *
TGGAGCTTTG GAATATTTTA TCCTGTATTC TTGTTT      (SEQ ID NO:9)
ACCTCGAAAC CTTATAAAAT AGGACATAAG AACAAA
```

FIG. 8F

CYTOKINE-, STRESS-, AND ONCOPROTEIN-ACTIVATED HUMAN PROTEIN KINASE KINASES

CROSS-REFERENCE TO RELATED APPLICATION

This application is a continuation-in-part of pending application Ser. No. 08/446,083, filed May 19, 1995; which application is incorporated herein by reference and to which application we claim priority under 35 USC §120.

STATEMENT AS TO FEDERALLY SPONSORED RESEARCH

This invention was made in part with National Cancer Institute research grant CA 58396. The Federal government has certain rights in the invention.

BACKGROUND OF THE INVENTION

This invention relates to protein kinases.

Mitogen-activated protein (MAP) kinases are important mediators of signal transduction from the cell surface to the nucleus. Multiple MAP kinases have been described in yeast including SMK1, HOG1, NPK1, FUS3, and KSS1. In mammals, the MAP kinases identified are extracellular signal-regulated MAP kinase (ERK), c-Jun amino-terminal kinase (JNK), and p38 kinase (Davis (1994) Trends Biochem. Sci. 19:470). These MAP kinase isoforms are activated by dual phosphorylation on threonine and tyrosine.

Activating Transcription Factor-2 (ATF2), ATFa, and cAMP Response Element Binding Protein (CRE-BPa) are related transcription factors that bind to similar sequences located in the promoters of many genes (Ziff (1990) Trends in Genet. 6:69). The binding of these transcription factors leads to increased transcriptional activity. ATF2 binds to several viral proteins, including the oncoprotein E1a (Liu and Green (1994) Nature 368:520), the hepatitis B virus X protein (Maguire et al. (1991) Science 252:842), and the human T cell leukemia virus 1 tax protein (Wagner and Green (1993) Science 262:395). ATF2 also interacts with the tumor suppressor gene product Rb (Kim et al. (1992) Nature 358:331), the high mobility group protein HMG(I)Y (Du et al. (1993) Cell 74:887), and the transcription factors nuclear NF-κB (Du et al. (1993) Cell 74:887) and c-Jun (Benbrook and Jones (1990) Oncogene 5:295).

SUMMARY OF THE INVENTION

We have identified and isolated a new group of human mitogen-activated protein kinase kinases (MKKs). The MKK isoforms described herein, MKK3 (including MKK6) and MKK4 (including MKK4-α, -β, and -γ) have serine, threonine, and tyrosine kinase activity, and specifically phosphorylate the human MAP kinase p38 at $Thr^{180}$ and $Tyr^{182}$. The MKK4 isoforms also phosphorylate the human MAP kinases JNK (including JNK1 and JNK2) at $Thr^{183}$ and $Tyr^{185}$.

Accordingly, the invention features a substantially pure human MKK polypeptide having serine, threonine, and tyrosine kinase activity that specifically phosphorylates human p38 MAP kinase. MKK3 has the amino acid sequence of SEQ ID NO:2. The invention further includes MKK6 having the amino acid sequence of SEQ ID NO:4 and having serine, threonine, and tyrosine kinase activity that specifically phosphorylates human p38 MAP kinase.

The invention further features a substantially pure human MKK polypeptide having serine, threonine, and tyrosine kinase activity that specifically phosphorylates human p38 MAP kinase and JNK. MKK4 isoform MKK4-α has the amino acid sequence of SEQ ID NO:6. MKK4 isoform MKK4-β has the amino acid sequence of SEQ ID NO:8. MKK4 isoform MKK4-γ has the amino acid sequence of SEQ ID NO:10.

As used herein, the term "mitogen-activating protein kinase kinase" or "MKK" means a protein kinase which possesses the characteristic activity of phosphorylating and activating a human mitogen-activating protein kinase. Examples of MKKs include MKK3 and MKK6, which specifically phosphorylate and activate p38 MAP kinase at $Thr^{180}$ and $Tyr^{182}$, and MKK4 isoforms which specifically phosphorylate and activate p38 MAP kinase at $Thr^{180}$ and $Tyr^{182}$, and JNK at $Thr^{183}$ and $Tyr^{185}$.

The invention includes the specific p38 MKKs disclosed, as well as closely related MKKs which are identified and isolated by the use of probes or antibodies prepared from the polynucleotide and amino acid sequences disclosed for the MKKs of the invention. This can be done using standard techniques, e.g., by screening a genomic, cDNA, or combinatorial chemical library with a probe having all or a part of the nucleic acid sequences of the disclosed MKKs. The invention further includes synthetic polynucleotides having all or part of the amino acid sequence of the MKKs herein described.

The term "polypeptide" means any chain of amino acids, regardless of length or post-translational modification (e.g., glycosylation or phosphorylation), and includes natural proteins as well as synthetic or recombinant polypeptides and peptides.

The term "substantially pure," when referring to a polypeptide, means a polypeptide that is at least 60%, by weight, free from the proteins and naturally-occurring organic molecules with which it is naturally associated. A substantially pure human MKK polypeptide is at least 75%, more preferably at least 90%, and most preferably at least 99%, by weight, human MKK polypeptide. A substantially pure human MKK can be obtained, for example, by extraction from a natural source; by expression of a recombinant nucleic acid encoding a human MKK polypeptide, or by chemically synthesizing the protein. Purity can be measured by any appropriate method, e.g., column chromatography, polyacrylamide gel electrophoresis, or HPLC analysis.

In one aspect, the invention features isolated and purified polynucleotides which encode the MKKs of the invention. In one embodiment, the polynucleotide is the nucleotide sequence of SEQ ID NO:1. In other embodiments, the polynucleotide is the nucleotide sequence of SEQ ID NO:3, SEQ ID NO:5, SEQ ID NO:7, or SEQ ID NO:9, respectively.

As used herein, "polynucleotide" refers to a nucleic acid sequence of deoxyribonucleotides or ribonucleotides in the form of a separate fragment or a component of a larger construct. DNA encoding portions or all of the polypeptides of the invention can be assembled from cDNA fragments or from oligonucleotides that provide a synthetic gene which can be expressed in a recombinant transcriptional unit. Polynucleotide sequences of the invention include DNA, RNA, and cDNA sequences, and can be derived from natural sources or synthetic sequences synthesized by methods known to the art.

As used herein, an "isolated" polynucleotide is a polynucleotide that is not immediately contiguous (i.e., covalently linked) with either of the coding sequences with which it is immediately contiguous (i.e., one at the 5' end and one at the 3' end) in the naturally-occurring genome of the organism from which the polynucleotide is derived. The term therefore includes, for example, a recombinant polynucleotide which is incorporated into a vector, into an autonomously replicating plasmid or virus, or into the genomic DNA of a prokaryote or eukaryote, or which exists as a separate molecule independent of other sequences. It also includes a recombinant DNA which is part of a hybrid gene encoding additional polypeptide sequences.

The isolated and purified polynucleotide sequences of the invention also include polynucleotide sequences that hybridize under stringent conditions to the polynucleotide sequences specified herein. The term "stringent conditions" means hybridization conditions that guarantee specificity between hybridizing polynucleotide sequences, such as those described herein, or more stringent conditions. One skilled in the art can select posthybridization washing conditions, including temperature and salt concentrations, which reduce the number of nonspecific hybridizations such that only highly complementary sequences are identified (Sambrook et al. (1989) in *Molecular Cloning*, 2d ed.; Cold Spring Harbor Laboratory Press, Cold Spring Harbor, N.Y., hereby specifically incorporated by reference).

The isolated and purified polynucleotide sequences of the invention also include sequences complementary to the polynucleotide encoding MKK (antisense sequences). Antisense nucleic acids are DNA or RNA molecules that are complementary to at least a portion of a specific mRNA molecule (Weintraub (1990) Scientific American 262:40). The invention includes all antisense polynucleotides capable of inhibiting production of MKK polypeptides. In the cell, the antisense nucleic acids hybridize to the corresponding mRNA, forming a double-stranded molecule. Antisense oligomers of about 15 nucleotides are preferred, since they are easily synthesized and introduced into a target MKK-producing cell. The use of antisense methods to inhibit the translation of genes is known in the art, and is described, e.g., in Marcus-Sakura Anal. Biochem., 172:289 (1988).

In addition, ribozyme nucleotide sequences for MKK are included in the invention. Ribozymes are RNA molecules possessing the ability to specifically cleave other single-stranded RNA in a manner analogous to DNA restriction endonucleases. Through the modification of nucleotide sequences encoding these RNAs, molecules can be engineered to recognize specific nucleotide sequences in an RNA molecule and cleave it (Cech (1988) J. Amer. Med. Assn. 260:3030). A major advantage of this approach is that, because they are sequence-specific, only mRNAs with particular sequences are inactivated.

There are two basic types of ribozymes namely, tetrahymena-type (Hasselhoff (1988) Nature 334:585) and "hammerhead"-type. Tetrahymena-type ribozymes recognize sequences which are four bases in length, while "hammerhead"-type ribozymes recognize base sequences 11–18 bases in length. The longer the sequence, the greater the likelihood that the sequence will occur exclusively in the target mRNA species. Consequently, hammerhead-type ribozymes are preferable to tetrahymena-type ribozymes for inactivating a specific mRNA species, and 18-base recognition sequences are preferable to shorter recognition sequences.

The MKK polypeptides can also be used to produce antibodies that are immunoreactive or bind epitopes of the MKK polypeptides. Accordingly, one aspect of the invention features antibodies to the MKK polypeptides of the invention. The antibodies of the invention include polyclonal antibodies which consist of pooled monoclonal antibodies with different epitopic specificities, as well as distinct monoclonal antibody preparations. Monoclonal antibodies are made from antigen-containing fragments of the MKK polypeptide by methods known in the art (See, for example, Kohler et al. (1975) Nature 256:495).

The term "antibody" as used herein includes intact molecules as well as fragments thereof, such as Fa, F(ab')$_2$, and Fv, which are capable of binding the epitopic determinant. Antibodies that bind MKK polypeptides can be prepared using intact polypeptides or fragments containing small peptides of interest as the immunizing antigen. The polypeptide or peptide used to immunize an animal can be derived from translated cDNA or chemically synthesized, and can be conjugated to a carrier protein, if desired. Commonly used carriers that are chemically coupled to peptides include bovine serum albumin and thyroglobulin. The coupled peptide is then used to immunize the animal (e.g., a mouse, a rat, or a rabbit).

The invention also features methods of identifying subjects at risk for MKK-mediated disorders by measuring activation of the MKK signal transduction pathway. Activation of the MKK signal transduction pathway can be determined by measuring MKK synthesis; activation of MKK isoforms; activation of MKK substrates p38 or JNK isoforms; or activation of p38 and JNK substrates such as ATF2, ATFa, CRE-BPa, and c-Jun. The term "JNK" or "JNK isoforms" includes both JNK1 and JNK2. The term "MKK substrate" as used herein include MKK substrates, as well as MKK substrate substrates, e.g., p38, JNK, ATF2, and c-Jun.

In one embodiment, activation of the MKK signal transduction pathway is determined by measuring activation of the MKK signal transduction pathway substrates p38, JNK isoforms, ATF2, or c-Jun. MKK activity is measured by the rate of substrate phosphorylation as determined by quantitation of the rate of [$^{32}$P]P incorporation. The specificity of MKK substrate phosphorylation can be tested by measuring p38 and JNK activation, or by employing mutated p38 and JNK molecules that lack the sites of MKK phosphorylations. Altered phosphorylation of the substrate relative to control values indicates alteration of the MKK signal transduction pathway, and increased risk in a subject of an MKK-mediated disorder. MKK activation of p38 and JNK can be detected in a coupled assay with the MKK signal transduction substrate ATF2, or related compounds such as ATFa and CRE-BPa. Activation can also be detected with the substrate c-Jun. When ATF2 is included in the assay, it is present as an intact protein or as a fragment of the intact protein, e.g., the activation domain (residues 1–109, or a portion thereof). ATF2 is incubated with a test sample in which MKK activity is to be measured and [γ-$^{32}$P]ATP, under conditions sufficient to allow the phosphorylation of ATF2. ATF2 is then isolated and the amount of phosphorylation quantitated. In a specific embodiment, ATF2 is isolated by immunoprecipitation, resolved by SDS-PAGE, and detected by autoradiography.

In another embodiment, activation of the MKK signal transduction pathway is determined by measuring the level of MKK expression in a test sample. In a specific embodiment, the level of MKK expression is measured by Western blot analysis. The proteins present in a sample are fractionated by gel electrophoresis, transferred to a membrane, and probed with labeled antibodies to MKK. In another specific embodiment, the level of MKK expression is measured by Northern blot analysis. Polyadenylated [poly (A)$^+$] mRNA is isolated from a test sample. The mRNA is fractionated by electrophoresis and transferred to a membrane. The membrane is probed with labeled MKK cDNA. In another embodiment, MKK expression is measured by quantitative PCR applied to expressed mRNA.

The MKKs of the invention are useful to screen reagents that modulate MKK activity. MKKs are activated by phosphorylation. Accordingly, in one aspect, the invention features methods for identifying a reagent which modulates MKK activity, by incubating MKK with the test reagent and measuring the effect of the test reagent on MKK synthesis, phosphorylation, function, or activity. In one embodiment, the test reagent is incubated with MKK and [$^{32}$P]-ATP, and the rate of MKK phosphorylation determined, as described above. In another embodiment, the test reagent is incubated with a cell transfected with an MKK polynucleotide expression vector, and the effect of the test reagent on MKK transcription is measured by Northern blot analysis, as described above. In a further embodiment, the effect of the test reagent on MKK synthesis is measured by Western blot analysis using an antibody to MKK. In still another embodiment, the effect of a reagent on MKK activity is measured by incubating MKK with the test reagent, [$^{32}$P]-ATP, and a substrate in the MKK signal transduction pathway, including one or more of p38, JNK, and ATF2. The rate of substrate phosphorylation is determined as described above.

The term "modulation of MKK activity" includes inhibitory or stimulatory effects. The invention is particularly useful for screening reagents that inhibit MKK activity. Such reagents are useful for the treatment or prevention of MKK-mediated disorders, for example, inflammation and oxidative damage.

The invention further features a method of treating a MKK-mediated disorder by administering to a subject in need thereof an effective dose of a therapeutic reagent that inhibits the activity of MKK.

By the term "MKK-mediated disorder" is meant a pathological condition resulting, at least in part, from excessive activation of an MKK signal transduction pathway. The MKK signal transduction pathways are activated by several factors, including inflammation and stress. MKK-mediated disorders include, for example, ischemic heart disease, burns due to heat or radiation (UV, X-ray, γ, β, etc.), kidney failure, liver damage due to oxidative stress or alcohol, respiratory distress syndrome, septic shock, rheumatoid arthritis, autoimmune disorders, and other types of inflammatory diseases.

As used herein, the term "therapeutic reagent" means any compound or molecule that achieves the desired effect on an MKK-mediated disorder when administered to a subject in need thereof.

MKK-mediated disorders further include proliferative disorders, particularly disorders that are stress-related. Examples of stress-related MKK-mediated proliferative disorders are psoriasis, acquired immune deficiency syndrome, malignancies of various tissues of the body, including malignancies of the skin, bone marrow, lung, liver, breast, gastrointestinal system, and genito-urinary tract. Preferably, therapeutic reagents inhibit the activity or expression of MKK inhibit cell growth or cause apoptosis.

A therapeutic reagent that "inhibits MKK activity" interferes with a MKK-mediated signal transduction pathway. For example, a therapeutic reagent can alter the protein kinase activity of MKK, decrease the level of MKK transcription or translation, e.g., an antisense polynucleotide able to bind MKK mRNA, or suppress MKK phosphorylation of p38, JNK, or ATF2, thus disrupting the MKK-mediated signal transduction pathway. Examples of such reagents include antibodies that bind specifically to MKK polypeptides, and fragments of MKK polypeptides that competitively inhibit MKK polypeptide activity.

A therapeutic reagent that "enhances MKK activity" supplements a MKK-mediated signal transduction pathway. Examples of such reagents include the MKK polypeptides themselves, which can be administered in instances where the MKK-mediated disorder is caused by underexpression of the MKK polypeptide. In addition, portions of DNA encoding an MKK polypeptide can be introduced into cells that underexpress an MKK polypeptide.

A "therapeutically effective amount" is an amount of a reagent sufficient to decrease or prevent the symptoms associated with the MKK-mediated disorder.

Therapeutic reagents for treatment of MKK-mediated disorders identified by the method of the invention are administered to a subject in a number of ways known to the art, including parenterally by injection, infusion, sustained-release injection or implant, intravenously, intraperitoneally, intramuscularly, subcutaneously, or transdermally. Epidermal disorders and disorders of the epithelial tissues are treated by topical application of the reagent. The reagent is mixed with other compounds to improve stability and efficiency of delivery (e.g., liposomes, preservatives, or dimethyl sulfoxide (DMSO)). Polynucleotide sequences, including antisense sequences, can be therapeutically administered by techniques known to the art resulting in introduction into the cells of a subject suffering from the MKK-mediated disorder. These methods include the use of vital vectors (e.g., retrovirus, adenovirus, vaccinia virus, or herpes virus), colloid dispersions, and liposomes.

The materials of the invention are ideally suited for the preparation of a kit for the detection of the level or activity of MKK. Accordingly, the invention features a kit comprising an antibody that binds MKK, or a nucleic acid probe that hybridizes to a MKK polynucleotide, and suitable buffers. The probe or monoclonal antibody can be labeled to detect binding to a MKK polynucleotide or protein. In a preferred embodiment, the kit features a labeled antibody to MKK.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, the preferred methods and materials are described below. All publications, patent applications, patents, and other references mentioned herein are incorporated by reference. In addition, the materials, methods, and examples are illustrative only and not intended to be limiting.

Other features and advantages of the invention will be apparent from the detailed description, and from the claims.

DETAILED DESCRIPTION

The drawings will first be described.

Drawings FIG. 1 is a comparison of the amino acid sequences of MKK3 (SEQ ID NO:2), MKK4-α (SEQ ID NO:6), the human MAP kinase kinases MEK1 (SEQ ID NO:11) and MEK2 (SEQ ID NO:12), and the yeast HOG1 MAP kinase kinase PBS2 (SEQ ID NO:13). MKK3 and MKK4 sequences were compared with the PILE-UP program (version 7.2; Wisconsin Genetics Computer Group). The protein sequences are presented in single letter code [A, Ala; C, Cys; D, Asp; E, Glu; F, Phe; G, Gly; H, His; I, Ile; K, Lys; L, Leu; M, Met; N, Asn; P, Pro; Q, Gln; R, Arg; S, Ser; T, Thr; V, Val; W, Trp, and Y, Tyr]. The PBS2 sequence is truncated at both the NH$_2$— (<) and COOH— (>) termini. Gaps introduced into the sequences to optimize the alignment are illustrated by a dash. Identical residues are indicated by a period. The sites of activating phosphorylation in MEK are indicated by asterisks.

FIG. 2 is a dendrogram showing the relation between members of the human and yeast MAP kinase kinases. The dendrogram was created by the unweighted pair-group method with the use of arithmetic averages (PILE-UP program). The human (hu) MAP kinase kinases MEK1, MEK2, MKK3, and MKK4; the Saccharomyces cerevisiae (sc) MAP kinase kinases PBS2, MKK1, and STE7; and the Saccharomyces pombe (sp) MAP kinase kinases WIS1 and BYR1 are presented.

FIG. 3 is a schematic representation of the ERK, p38, and JNK signal transduction pathways. MEK1 and MEK2 are activators of the ERK subgroup of MAP kinase. MKK3 and MKK4 are activators of the p38 MAP kinase. MKK4 is identified as an activator of both the p38 and JNK subgroups of MAP kinase.

FIG. 4 is a representation of the nucleic acid (SEQ ID NO:1) and amino acid sequences (SEQ ID NO:2) for MKK3.

FIG. 5 is a representation of the nucleic acid (SEQ ID NO:3) and amino acid sequences (SEQ ID NO:4) for MKK6.

FIG. 6 is a representation of the nucleic acid (SEQ ID NO:5) and amino acid sequences (SEQ ID NO:6) for MKK4α.

FIG. 7 is a representation of the nucleic acid (SEQ ID NO:7) and amino acid sequences (SEQ ID NO:8) for MKK4β.

FIG. 8 is a representation of the nucleic acid (SEQ ID NO:9) and amino acid sequences (SEQ ID NO:10) for MKK4γ.

HUMAN MITOGEN-ACTIVATED PROTEIN KINASE KINASES

Figure 2:
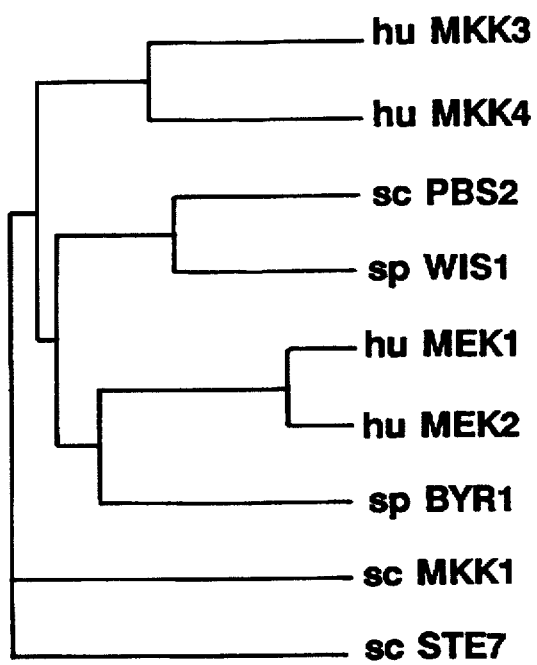

The human MAP kinase kinases MKK3 and MKK4 (MKK3/4) described herein mediate the transduction of specific signals from the cell surface to the nucleus along specific pathways. These signal transduction pathways are initiated by factors such as cytokines, UV radiation, osmotic shock, and oxidative stress. Activation of MKK3/4 results in activation of the MAP kinases p38 (MKK3/4) and JNK (MKK4). p38 and JNK in turn activate a group of related transcription factors such as ATF2, ATFa, and CRE-BPa. These transcription factors in turn activate expression of specific genes. For example, ATF2 in known to activate expression of human T cell leukemia virus 1 (Wagner and Green (1993) Science 262:395), transforming growth factor-b2 (Kim et al. (1992) supra), interferon-β (Du et al. (1993) Cell 74:887), and E-selectin (DeLuca et al. (1994) J. Biol. Chem. 269:19193). In addition, ATF2 is implicated in the function of a T cell-specific enhancer (Georgopoulos et al. (1992) Mol. Cell. Biol. 12:747).

The isolation of human MKKs is described in Example 1 and in Dérijard et al. (1995) Science 267:682–685, hereby specifically incorporated by reference. Distinctive regions of the yeast PBS2 sequence were used to design polymerase chain reaction (PCR) primers. Amplification of human brain mRNA with these primers resulted in the formation of specific products which were cloned into a plasmid vector and sequenced. Two different complementary DNAs (cDNAs) that encoded human protein kinases were identified: one encoding a 36 kD protein (MKK3), and one encoding a 44 kD protein (MKK4). MKK4 includes 3 isoforms that vary slightly at the NH$_2$-terminal, identified as α, β, and γ. The amino acid sequences of MKK3 (SEQ ID NO:2), MKK4-α (SEQ ID NO:6), MKK4-β (SEQ ID NO:8), and MKK4-γ (SEQ ID NO:10) are shown in FIG. 1. The nucleic acid and amino acid sequences of MKK3 (FIG. 5), MKK6 (FIG. 6), MKK4α (FIG. 7), MKK4β (FIG. 8), and MKK4γ (FIG. 9) are also provided. MKK6 was isolated from a human skeletal muscle library by cross-hybridization with MKK3. Except for differences at the N-terminus, MKK6 is highly homologous to MKK3. Other human MKK3 and MKK4 isoforms that exist can be identified by the method described in Example 1.

The expression of these human MKK isoforms was examined by Northern (RNA) blot analysis of mRNA isolated from eight adult human tissues (Example 2). Both protein kinases were found to be widely expressed in human tissues, with the highest expression seen in skeletal muscle tissue.

The substrate specificity of MKK3 was investigated in an in vitro phosphorylation assay with recombinant epitope-tagged MAP kinases (JNK1, p38, and ERK2) as substrates (Example 3). MKK3 phosphorylated p38, but did not phosphorylate JNK1 or ERK2. Phosphoaminoacid analysis of p38 demonstrated the presence of a phosphothreonine and phosphotyrosine. Mutational analysis of p38 demonstrated that replacement of phosphorylation sites Thr$^{180}$ and Tyr$^{182}$ with Ala and Phe, respectively, blocked p38 phosphorylation. These results establish that MKK3 functions in vitro as a p38 MAP kinase kinase.

Studies of the in vitro substrate specificity of MKK4 are described in Example 4. MKK4 incubated with [γ-$^{32}$P]AFP, and JNK1, p38, or ERK2 was found to phosphorylate both p38 and JNK1. MKK4 activation of JNK and p38 was also studied by incubating MKK4 with wild-type or mutated JNK1 or p38. The p38 substrate ATF2 was included in each assay. MKK4 was found to exhibit less autophosphorylation than MKK3. MKK4 was also found to be a substrate for activated MAP kinase. Unlike MKK3, MKK4 was also found to activate JNK1. MKK4 incubated with wild-type JNK1, but not mutated JNK1, resulted in increased phosphorylation of ATF2. These results establish that MKK4 is a p38 MAP kinase kinase that also phosphorylates the JNK subgroup of MAP kinases.

In vivo activation of p38 by UV-stimulated MKK3 is described in Example 5. Cells expressing MKK3 were exposed in the presence or absence of UV radiation. MKK3 was isolated by immunoprecipitation and used for protein kinase assays with the substrates p38 or JNK. ATF2 was included in some assays as a substrate for p38 and JNK. MKK3 from non-activated cultured COS cells caused a small amount of phosphorylation of p38 MAP kinase, resulting from basal activity of MKK3. MKK3 from UV-irradiated cells caused increased phosphorylation of p38 MAP kinase, but not of JNK1. An increase in p38 activity was also detected in assays in which ATF2 was included as a substrate. These results establish that MKK3 is activated by UV radiation.

The effect of expression of MKK3 and MKK4 on p38 activity was examined in COS-1 cells (Example 6). Cells were transfected with a vector encoding p38 and a MEK1, MKK3, or MKK4. Some of the cells were also exposed to EGF or UV radiation. p38 was isolated by immunoprecipitation and assayed for activity with [γ-$^{32}$P]ATP and ATF2. The expression of the ERK activator MEK1 did not alter p38 phosphorylation of ATF2. In contrast, expression of MKK3 or MKK4 caused increased activity of p38 MAP kinase. The activation of p38 caused by MKK3 and MKK4 was similar to that observed in UV-irradiated cells, and was much greater than that detected in EGF-treated cells. These in vitro results provide evidence that MKK3 and MKK4 activate p38 in vivo.

A series of experiments was conducted to examine the potential regulation of ATF2 by JNK1. These experiments are described in Gupta et al. (1995) Science 267:389–393, hereby specifically incorporated by reference. The effect of UV radiation on ATF2 phosphorylation was investigated in COS-1 cells transfected with and without epitope-tagged JNK1 (Example 7). Cells were exposed to UV radiation, and JNK1 and JNK2 visualized by in-gel protein kinase assay with the substrate ATF2. JNK1 and JNK2 were detected in transfected and non-transfected cells exposed to UV radiation; however, JNK1 levels were higher in the transfected cells. These results demonstrate that ATF2 is a substrate for the JNK1 and JNK2 protein kinases, and that these protein kinases are activated in cells exposed to UV light.

The site of JNK1 phosphorylation of ATF2 was examined by deletion analysis (Example 8). Progressive $NH_2$-terminal domain deletion GST-ATF2 fusion proteins were generated, and phosphorylation by JNK1 isolated from UV-irradiated cells was examined. The results showed that JNK1 requires the presence of ATF2 residues 1–60 for phosphorylation of the $NH_2$-terminal domain of ATF2.

The ATF2 residues required for binding of JNK1 were similarly examined. JNK1 was incubated with immobilized ATF2, unbound JNK1 was removed by extensive washing, and bound JNK1 was detected by incubation with [$\gamma$-$^{32}$P] ATP. Results indicate that residues 20 to 60 of ATF2 are required for binding and phosphorylation by JNK1. A similar binding interaction between ATF2 and the 55 kD JNK2 protein kinase has also been observed.

Phosphorylation by JNK1 was shown to reduce the electrophoretic mobility of ATF2 (Example 9). Phosphoamino acid analysis of the full-length ATF2 molecule (residues 1–505) demonstrated that JNK phosphorylated both Thr and Ser residues. The major sites of Thr and Ser phosphorylation were located in the $NH_2$ and COOH terminal domains, respectively. The $NH_2$-terminal sites of phosphorylation were identified as $Thr^{69}$ and $Thr^{71}$ by phosphopeptide mapping and mutational analysis. These sites of Thr phosphorylation are located in a region of ATF2 that is distinct from the sub-domain required for JNK binding (residues 20 to 60).

The reduced electrophoretic mobility seen with phosphorylation of ATF2 was investigated further (Example 10). JNK1 was activated in CHO cells expressing JNK1 by treatment with UV radiation, pro-inflammatory cytokine interleukin-1 (IL-1), or serum. A decreased electrophoretic mobility of JNK1-activated ATF2 was observed in cells treated with UV radiation and IL-1. Smaller effects were seen after treatment of cells with serum. These results indicate that ATF2 is an in vivo substrate for JNK1.

The effect of UV radiation on the properties of wild-type ($Thr^{69,71}$) and phosphorylation-defective ($Ala^{69,71}$) ATF2 molecules was investigated (Example 11). Exposure to UV caused a decrease in the electrophoretic mobility of both endogenous and over-expressed wild-type ATF2. This change in electrophoretic mobility was associated with increased ATF2 phosphorylation. Both the electrophoretic mobility shift and increased phosphorylation were blocked by the replacement of $Thr^{69}$ and $Thr^{71}$ with Ala in ATF2. This mutation also blocked the phosphorylation of ATF2 on Thr residues in vivo.

Transcriptional activities of fusion proteins consisting of the GAL4 DNA binding domain and wild-type or mutant ATF2 were examined (Example 12). Point mutations at $Thr^{69}$ and/or $Thr^{71}$ of ATF2 significantly decreased the transcriptional activity of ATF2 relative to the wild-type molecule, indicating the physiological relevance of phosphorylation at these sites for activity.

The binding of JNK1 to the $NH_2$-terminal activation domain of ATF2 (described in Example 8) suggested that a catalytically inactive JNK1 molecule could function as a dominant inhibitor of the wild-type JNK1 molecule. This hypothesis was investigated by examining the effect of a catalytically inactive JNK1 molecule on ATF2 function (Example 13). A catalytically-inactive JNK1 mutant was constructed by replacing the sites of activating $Thr^{183}$ and $Tyr^{185}$ phosphorylation with Ala and Phe, respectively ($Ala^{183}$,$Phe^{185}$, termed "dominant-negative"). Expression of wild-type JNK1 caused a small increase in serum-stimulated ATF2 transcriptional activity. In contrast, dominant-negative JNK1 inhibited both control and serum-stimulated ATF2 activity. This inhibitory effect results from the non-productive binding of the JNK1 mutant to the ATF2 activation domain, effectively blocking ATF2 phosphorylation.

The tumor suppressor gene product Rb binds to ATF2 and increases ATF2-stimulated gene expression (Kim et al. (1992) Nature 358:331). Similarly, the adenovirus oncoprotein E1A associates with the DNA binding domain of ATF2 and increases ATF2-stimulated gene expression by a mechanism that requires the $NH_2$-terminal activation domain of ATF2 (Liu and Green (1994) Nature 368:520). ATF2 transcriptional activity was investigated with the luciferase reporter gene system in control, Rb-treated, and E1A-treated cells expressing wild-type or mutant ATF2 molecules (Example 14). Rb and E1A were found to increase ATF2-stimulated gene expression of both wild-type and mutant ATF2. However, mutant ATF2 caused a lower level of reporter gene expression than did wild-type ATF2. Together, these results indicate a requirement for ATF2 phosphorylation (on $Thr^{69}$ and $Thr^{71}$) plus either Rb or E1A for maximal transcriptional activity. Thus, Rb and E1A act in concert with ATF2 phosphorylation to control transcriptional activity.

A series of experiments were conducted to examine the action of p38 activation and to establish the relationship of the p38 MAP kinase pathway to the ERK and JNK signal transduction pathways (Raingeaud et al. (1995) J. Biol. Chem. 270:7420, hereby specifically incorporated by reference). Initially, the substrate specificity of p38 was investigated by incubating p38 with proteins that have been demonstrated to be substrates for the ERK and/or JNK groups of MAP kinases (Example 15). We examined the phosphorylation of MBP (Erickson et al. (1990) J. Biol. Chem. 265:19728), EGF-R (Northwood et al. (1991) J. Biol. Chem. 266:15266), cytoplasmic phospholipase $A_2$ ($cPLA_2$) (Lin et al. (1993) Cell 72:269), c-Myc (Alvarez et al. (1991) J. Biol. Chem. 266:15277), IκB, c-Jun, and wild-type ($Thr^{69,71}$) or mutated ($Ala^{69,71}$) ATF2. p38 phosphorylated MBP and EGF-R, and to a lesser extent IκB, but not the other ERK substrates, demonstrating that the substrate specificity of p38 differs from both the ERK and JNK groups of MAP kinases. Wild-type ATF2, but not mutated ATF2 ($Ala^{69,71}$), was found to be an excellent p38 substrate.

The phosphorylation of ATF2 by p38 was associated with an electrophoretic mobility shift of ATF2 during polyacrylamide gel electrophoresis. We tested the hypothesis that p38 phosphorylates ATF2 at the same sites as JNK1 by replacing $Thr^{69}$ and $Thr^{71}$ with Ala ($Ala^{69,71}$). It was found that p38 did not phosphorylate mutated ATF2, which demonstrates that p38 phosphorylates ATF2 within the NH$_2$-terminal activation domain on Thr$^{69}$ and Thr$^{71}$.

A comparison of the binding of JNK and p38 to ATF2 was conducted by incubating extracts of cells expressing JNK1 or p38 with epitope alone (GST) or GST-ATF2 (residues 1–109 containing the activation domain) (Example 16). Bound protein kinases were detected by Western blot analysis. The results demonstrate that both p38 and JNK bind to the ATF2 activation domain.

EGF and phorbol ester are potent activators of the ERK signal transduction pathway (Egan and Weinberg (1993) Nature 365:781), causing maximal activation of the ERK sub-group of MAP kinases. These treatments, however, cause only a small increase in JNK protein kinase activity (Dérijard et al. (1994) supra; Hibi et al. (1993) supra). The effects of EGF or phorbol esters, as well UV radiation, osmotic shock, interleukin-1, tumor necrosis factor, and LPS, on p38 activity were all tested (Example 17). Significantly, EGF and phorbol ester caused only a modest increase in p38 protein kinase activity, whereas environmental stress (UV radiation and osmotic shock) caused a marked increase in the activity of both p38 and JNK. Both p38 and JNK were activated in cells treated with pro-inflammatory cytokines (TNF and IL-1) or endotoxic LPS. Together, these results indicate that p38, like JNK, is activated by a stress-induced signal transduction pathway.

ERKs and JNKs are activated by dual phosphorylation within the motifs Thr-Glu-Tyr and Thr-Pro-Tyr, respectively. In contrast, p38 contains the related sequence Thr-Gly-Tyr. To test whether this motif is relevant to the activation of p38, the effect of the replacement of Thr-Gly-Tyr with Ala-Gly-Phe was examined (Example 18). The effect of UV radiation on cells expressing wild-type (Thr$^{180}$,Tyr$^{182}$) or mutant p38 (Ala$^{180}$,Phe$^{182}$) was studied. Western blot analysis using an anti-phosphotyrosine antibody demonstrated that exposure to UV radiation caused an increase in the Tyr phosphorylation of p38. The increased Tyr phosphorylation was confirmed by phosphoaminoacid analysis of p38 isolated from [γ-$^{32}$P]phosphate-labeled cells. This analysis also demonstrated that UV radiation caused increased Thr phosphorylation of p38. Significantly, the increased phosphorylation on Thr$^{180}$ and Tyr$^{182}$ was blocked by the Ala$^{180}$/Phe$^{182}$ mutation. This result demonstrates that UV radiation causes increased activation of p38 by dual phosphorylation.

It has recently been demonstrated that ERK activity is regulated by the mitogen-induced dual specificity phosphatases MKP1 and PAC1 (Ward et al. (1994) Nature 367:651). The activation of p38 by dual phosphorylation (Example 18) raises the possibility that p38 may also be regulated by dual specificity phosphatases. We examined the effect of MKP1 and PAC1 on p38 MAP kinase activation (Example 19). Cells expressing human MKP1 and PAC1 were treated with and without UV radiation, and p38 activity measured. The expression of PAC1 or MKP1 was found to inhibit p38 activity. The inhibitory effect of MKP1 was greater than PAC1. In contrast, cells transfected with a catalytically inactive mutant phosphatase (mutant PAC1 Cys$^{257}$/Ser) did not inhibit p38 MAP kinase. These results demonstrate that p38 can be regulated by dual specificity phosphatases PAC1 and MKP1.

The sub-cellular distribution of p38 MAP kinase was examined by indirect immunofluorescence microscopy (Example 20). Epitope-tagged p38 MAP kinase was detected using the M2 monoclonal antibody. Specific staining of cells transfected with epitope-tagged p38 MAP kinase was observed at the cell surface, in the cytoplasm, and in the nucleus. Marked changes in cell surface and nuclear p38 MAP kinase were not observed following UV irradiation, but an increase in the localization of cytoplasmic p38 MAP kinase to the perinuclear region was detected.

A series of experiments were conducted to study the activation of JNK by hyper-osmotic media (Example 21). These experiments were reported by Galcheva-Gargova et al. (1994) Science 265:806, hereby specifically incorporated by reference. CHO cells expressing epitope-tagged JNK1 were incubated with 0–1000 mM sorbitol, and JNK1 activity measured in an immune complex kinase assay with the substrate c-Jun. Increased JNK1 activity was observed in cells incubated 1 hour with 100 mM sorbitol. Increased JNK1 activity was observed within 5 minutes of exposure to 300 mM sorbitol. Maximal activity was observed 15 to 30 minutes after osmotic shock with a progressive decline in JNK1 activity at later times. The activation of JNK by osmotic shock was studied in cells expressing wild-type (Thr$^{183}$, Tyr$^{185}$) or mutated (Ala$^{183}$, Phe$^{185}$) JNK1. JNK1 activity was measured after incubation for 15 minutes with or without 300 mM sorbitol. Cells expressing wild-type JNK1 showed increased JNK1 activity, while cells expressing mutated JNK1 did not. These results demonstrate that the JNK signal transduction pathway is activated in cultured mammalian cells exposed to hyper-osmotic media.

Figure 3:
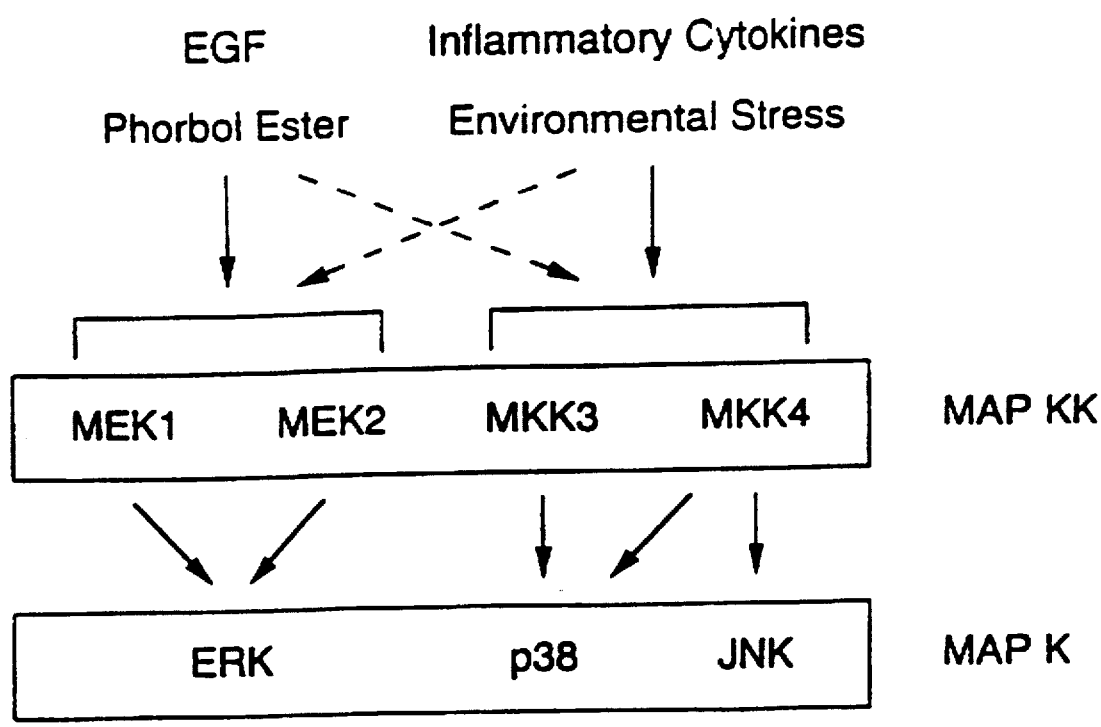

The results of the above-described experiments are illustrated in FIG. 3, which diagrams the ERK, p38, and JNK MAP kinase signal transduction pathways. ERKs are potently activated by treatment of cells with EGF or phorbol esters. In contrast, p38 is only slightly activated under these conditions (Example 15). However, UV radiation, osmotic stress, and inflammatory cytokines cause a marked increase in p38 activity. This difference in the pattern of activation of ERK and p38 suggests that these MAP kinases are regulated by different signal transduction pathways. The molecular basis for the separate identity of these signal transduction pathways is established by the demonstration that the MAP kinase kinases that activate ERK (MEK1 and MEK2) and p38 (MKK3 and MKK4) are distinct.

MKK isoforms are useful for screening reagents which modulate MKK activity. Described in the Use section following the examples are methods for identifying reagents capable of inhibiting or activating MKK activity.

The discovery of human MKK isoforms and MKK-mediated signal transduction pathways is clinically significant for the treatment of MKK-mediated disorders. One use of the MKK isoforms is in a method for screening reagents able to inhibit or prevent the activation of the MKK-MAP kinase-ATF2 pathways.

The following examples are meant to illustrate, not limit, the invention.

EXAMPLE 1
MKK Protein Kinases

The primary sequences of MKK3 and MKK4 were deduced from the sequence of cDNA clones isolated from a human fetal brain library.

The primers TTYTAYGGNGCNTTYTTYATHGA (SEQ ID NO:14) and ATBCTYTCNGGNGCCATKTA (SEQ ID NO:15) were designed based on the sequence of PBS2 (Brewster et al. (1993) Science 259:1760; Maeda et al. (1994) Nature 369:242). The primers were used in a PCR reaction with human brain mRNA as template. Two sequences that encoded fragments of PBS2-related protein kinases were identified. Full-length human cDNA clones were isolated by screening of a human fetal brain library (Dérijard et al. (1994) supra). The cDNA clones were examined by sequencing with an Applied Biosystems model 373A machine. The largest clones obtained for MKK3 (2030 base pairs (bp)) and MKK4 (3576 bp) contained the entire coding region of these protein kinases.

The primary structures of MKK3 (SEQ ID NO:2) and MKK4α (SEQ ID NO:6) are shown in FIG. 1. An in-frame termination codon is located in the 5' untranslated region of the MKK3 cDNA, but not in the 5' region of the MKK4 cDNA. The MKK4 protein sequence presented starts at the second in-frame initiation codon.

These sequences were compared to those of the human MAP kinase kinases MEK1 (SEQ ID NO:11) and MEK2 (SEQ ID NO:12) (Zheng and Guan (1993) J. Biol. Chem 268:11435) and of the yeast MAP kinase kinase PBS2 (SEQ ID NO:13) (Boguslawaski and Polazzi (1987) Proc. Natl. Acad. Sci. USA 84:5848) (FIG. 1). The identity and similarity of the kinases with human MKK3 (between subdomains I and XI) were calculated with the BESTFIT program (version 7.2; Wisconsin Genetics Computer Group) (percent of identity to percent of similarity): MEK1, 41%/63%; MEK2, 41%/62%; MKK4α, 52%/73%; and PBS2, 40%/59%). The identity and similarity of the kinases with human MKK4α were calculated to be as follows (percent of identity to percent of similarity): MEK1, 44%/63%; MEK2, 45%/61%; MKK3, 52%/73%; and PBS2, 44%/58%.

The cDNA sequences of MKK3 and MKK4γ have been deposited in GenBank with accession numbers L36719 and L36870, respectively. The MKK4γ cDNA sequence contains both the cDNA sequences of MKK4α and MKK4β, which are generated in vivo from alternate splicing sites. One of ordinary skill in the art can readily determine the amino acid sequences of MKK3 and MKK4 isoforms from the deposited cDNA sequences.

EXAMPLE 2
Expression of MKK3 and MKK4 mRNA in Adult Human Tissue

Northern blot analysis was performed with polyadenylated [poly(A)$^+$] mRNA (2 µg) isolated from human heart, brain, placenta, lung, liver, muscle, kidney, and pancreas tissues. The mRNA was fractionated by denaturing agarose gel electrophoresis and was transferred to a nylon membrane. The blot was probed with the MKK3 and MKK4 cDNA labeled by random priming with [α-$^{32}$P]ATP (deoxyadenosine triphosphate) (Amersham International PLC). MKK3 and MKK4 were expressed in all tissues examined; the highest expression of MKK3 and MKK4 was found in skeletal muscle tissue.

The relation between members of the human and yeast MAP kinase kinase group is presented as a dendrogram (FIG. 2). MKK3/4 form a unique subgroup of human MAP kinase kinases.

EXAMPLE 3
In Vitro Phosphorylation of p38 MAP kinase by MKK3

GST-JNK1, and GST-ERK2 have been described (Dérijard et al. (1994) supra; Gupta et al. (1995) Science 267:389; Wartmann and Davis (1994) J. Biol. Chem. 269:6695, each herein specifically incorporated by reference). GST-p38 MAP kinase was prepared from the expression vector pGSTag (Dressier et al. (1992) Biotechniques 13:866) and a PCR fragment containing the coding region of the p38 MAP kinase cDNA. GST-MKK3 and MKK4 were prepared with pGEX3X (Pharmacia-LKB Biotechnology) and PCR fragments containing the coding region of the MKK3 and MKK4 cDNAs. The GST fusion proteins were purified by affinity chromatography with the use of GSH-agarose (Smith and Johnson (1988) Gene 67:31). The expression vectors pCMV-Flag-JNK1 and pCMV-MEK1 have been described (Dérijard et al. (1994) supra; Wartmann and Davis (1994) supra). The plasmid pCMV-Flag-p38 MAP kinase was prepared with the expression vector pCMV5 (Andersson et al. (1989) J. Biol. Chem 264:8222) and the p38 MAP kinase cDNA. The expression vectors for MKK3 and MKK4 were prepared by subcloning of the cDNAs into the polylinker of pCDNA3 (Invitrogen). The Flag epitope (Asp-Tyr-Lys-Asp-Asp-Asp-Asp-Lys) (SEQ ID NO:16); Immunex, Seattle, Wash.) was inserted between codons 1 and 2 of the kinases by insertional overlapping PCR (Ho et al. (1989) Gene 77:51).

Protein kinase assays were performed in kinase buffer (25 mM 4-(2-hydroxyethyl)-1-piperazineethansulfonic acid, pH 7.4, 25 mM β-glycerophosphate, 25 mM MgCl$_2$, 2 mM dithiothreitol, and 0.1 mM orthovanadate). Recombinant GST-MKK3 was incubated with [γ-$^{32}$P]ATP and buffer, GST-JNK1, GST-p38 MAP kinase, or GST-ERK2. The assays were initiated by the addition of 1 µg of substrate proteins and 50 µM [γ-$^{32}$P]ATP (10 Ci/mmol) in a final volume of 25 µl. The reactions were terminated after 30 minutes at 25° C. by addition of Laemmli sample buffer. The phosphorylation of the substrate proteins was examined after SDS-polyacrylamide gel electrophoresis (SDS-PAGE) by autoradiography. Phosphoaminoacid analysis was performed by partial acid hydrolysis and thin-layer chromatography (Dérijard et al. (1994) supra; Alvarez et al. (1991) J. Biol. Chem. 266:15277). Autophosphorylation of MKK3 was observed in all groups. MKK3 phosphorylated p38 MAP kinase, but not JNK1 or ERK2.

A similar insertional overlapping PCR procedure was used to replace Thr$^{180}$ and Tyr$^{182}$ of p38, with Ala and Phe, respectively. The sequence of all plasmids was confirmed by automated sequencing on an Applied Biosystems model 373A machine. GST-MKK3 was incubated with [γ-$^{32}$P]ATP and buffer, wild-type GST-p38 MAP kinase (TGY), or mutated GST-p38 MAP kinase (AGF). The phosphorylated proteins were resolved by SDS-PAGE and detected by autoradiography. Only phosphorylation of wild-type p38 was observed.

EXAMPLE 4
In Vitro Phosphorylation and Activation of JNK and p38 MAP Kinase by MKK4

Protein kinase assays were conducted as described in Example 3. Recombinant GST-MKK4 was incubated with [γ-$^{32}$P]ATP and buffer, GST-JNK1, GST-p38 MAP kinase, or GST-ERK2. JNK1 and p38 were phosphorylated, as was MKK4 incubated with JNK1 and p38.

GST-MKK4 was incubated with [γ-$^{32}$P]ATP and buffer, wild-type JNK1 (Thr$^{183}$, Tyr$^{185}$), or mutated GST-JNK1 (Ala$^{183}$, Phe$^{185}$). The JNK1 substrate ATF2 (Gupta et al. (1995) supra) was included in each incubation. ATF2 was phosphorylated in the presence of MKK4 and wild-type JNK1. The results establish that MKK4 phosphorylates and activates both p38 and JNK1.

EXAMPLE 5
Phosphorylation and Activation of p38 MAP Kinase by UV-stimulated MKK3

Epitope-tagged MKK3 was expressed in COS-1 cells maintained in Dulbecco's modified Eagle's medium supplemented with fetal bovine serum (5%) (Gibco-BRL). The cells were transfected with the lipofectamine reagent according to the manufacturer's recommendations (Gibco-BRL) and treated with UV radiation or EGF as described (Dérijard et al. (1994) supra).

The cells were exposed in the absence and presence of UV-C (40 J/m$^2$). The cells were solubilized with lysis buffer (20 mM tris, pH 7.4, 1% Triton X-100, 10% glycerol, 137 mM NaCl, 2 mM EDTA, 25 mM β-glycerophosphate, 1 mM Na orthovanadate, 1 mM phenylmethylsulfonyl fluoride, and leupeptin (10 µg/ml)) and centrifuged at 100,000×g for 15 minutes at 4° C. MKK3 was isolated by immunoprecipitation. The epitope-tagged protein kinases were incubated for 1 hour at 4° C. with the M2 antibody to the Flag epitope (IBI-Kodak) bound to protein G-Sepharose (Pharmacia-LKB Biotechnology). The immunoprecipitates were washed twice with lysis buffer and twice with kinase buffer.

Protein kinase assays were conducted with the substrate GST-p38 MAP kinase or JNK1. ATF2 was included in some assays. Basal levels of MKK3 phosphorylation of p38 MAP kinase were observed. UV-irradiation resulted in increased phosphorylation of p38 MAP kinase, but not of JNK1. The increased p38 MAP kinase activity resulted in increased phosphorylation of ATF2.

EXAMPLE 6
Activation of p38 MAP Kinase in Cells Expressing MKK3 and MKK4

COS-1 cells were transfected with epitope-tagged p38 MAP kinase, together with an empty expression vector or an expression vector encoding MEK1, MKK3, or MKK4α. Some of the cultures were exposed to UV radiation (40 J/m$^2$) or treated with 10 nM EGF. p38 MAP kinase was isolated by immunoprecipitation with M2 monoclonal antibody, and the protein kinase activity was measured in the immunecomplex with [γ-$^{32}$P]ATP and ATF2 as substrates. The product of the phosphorylation reaction was visualized after SDS-PAGE by autoradiography. ATF2 was not phosphorylated in the control MEK1, or EGF-treated groups, but was phosphorylated in the MKK3, MKK4, and F-irradiated groups. MKK3 and MKK4 phosphorylation of ATF2 was similar to that seen with p38 MAP kinase isolated from UV-irradiated cells.

EXAMPLE 7
Phosphorylation of ATF2 by JNK1 and JNK2

COS-1 cells were maintained in Dulbecco's modified Eagle's medium supplemented with bovine serum albumin (5%) (Gibco-BRL). Metabolic labeling with [$^{32}$P]P was performed by incubation of cells for 3 hours in phosphate-free modified Eagle's medium (Flow Laboratories Inc.) supplemented with [$^{32}$P]orthophosphate (2 mCi/ml) (Dupont-NEN). COS-1 cells were transfected without (Mock) and with epitope-tagged JNK1 (JNK1). Plasmid expression vectors encoding the JNK1 cDNA have previously been described (Dérijard et al. (1994) Cell 76:1025, herein specifically incorporated by reference). Plasmid DNA was transfected into COS-1 cells by the lipofectamine method (Gibco-BRL). After 48 hours of incubation, some cultures were exposed to 40 J/m$^2$ UV radiation and incubated for 1 hour at 37° C.

Cells were lysed in 20 mM Tris, pH 7.5, 25 mM β-glycerophosphate, 10% glycerol, 1% Triton X-100, 0.5% (w/v) deoxycholate, 0.1% (w/v) SDS, 0.137M NaCl, 2 mM pyrophosphate, 1 mM orthovanadate, 2 mM EDTA, 10 µg/ml leupeptin, 1 mM PMSF. Soluble extracts were prepared by centrifugation in a microfuge for 20 minutes at 4° C. JNK1 immunoprecipitates were also prepared by reaction with a rabbit antiserum prepared with recombinant JNK1 as an antigen.

In-gel protein kinase assays were performed with cell lysates and JNK1 immunoprecipitates after SDS-PAGE by renaturation of protein kinases, polymerization of the substrate (GST-ATF2, residues 1–505) in the gel, and incubation with [γ-$^{32}$P]ATP (Dérijard et al. (1994) supra). The incorporation of [$^{32}$P]phosphate was visualized by autoradiography and quantitated with a Phosphorimager and imageQuant soft-ware (Molecular Dynamics Inc., Sunnyvale, Calif.). The cell lysates demonstrate the presence of 46 kD and 55 kD protein kinases that phosphorylate ATF2 in extracts prepared from UV-irradiated cells. The 46 kD and 55 kD protein kinases were identified as JNK1 and JNK2, respectively.

EXAMPLE 8
Binding of JNK1 to ATF2 and Phosphorylation of the NH$_2$-Terminal Activation Domain The site of JNK1 phosphorylation of ATF2 was investigated by generation of progressive NH$_2$-terminal domain deletions of ATF2. Plasmid expression vectors encoding ATF2 (pECE-ATF2) (Liu and Green (1994) and (1990)), have been described. Bacterial expression vectors for GST-ATF2 fusion proteins were constructed by sub-cloning ATF2 cDNA fragments from a polymerase chain reaction (PCR) into pGEX-3X (Pharmacia-LKB Biotechnology Inc.). The sequence of all constructed plasmids was confirmed by automated sequencing with an Applied Biosystems model 373A machine. The GST-ATF2 proteins were purified as described (Smith and Johnson (1988) Gene 67:31), resolved by SDS-PAGE and stained with Coomassie blue. GST-ATF2 fusion proteins contained residues 1–505, 1–349, 350–505, 1–109, 20–109, 40–109, and 60–109.

The phosphorylation of GST-ATF2 fusion proteins by JNK1 isolated from UV-irradiated cells was examined in an immunocomplex kinase assay. Immunocomplex kinase assays were performed with Flag epitope-tagged JNK1 and the monoclonalantibody M2 (IBI-Kodak) as described by Dérijard et al. (1994) supra). Immunecomplex protein kinase assays were also performed with a rabbit antiserum prepared with recombinant JNK1 as an antigen. The cells were solubilized with 20 mM Tris, pH 7.5, 10% glycerol, 1% Triton X-100, 0.137M NaCl, 25 mM β-glycerophosphate, 2 mM EDTA, 1 mM orthovanadate, 2 mM pyrophosphate, 10 µg/ml leupeptin, and 1 mM PMSF. JNK1 was immunoprecipitated with protein G-Sepharose bound to a rabbit polyclonal antibody to JNK or the M2 monoclonal antibody to the Flag epitope. The beads were washed three times with lysis buffer and once with kinase buffer (20 mM Hepes, pH 7.6, 20 mM MgCl$_2$, 25 mM β-glycerophosphate, 100 µM Na orthovanadate, 2 mM dithiothreitol). The kinase assays were performed at 25° C. for 10 minutes with 1 µg of substrate, 20 µM adenosine triphosphate and 10 µCi of [γ-$^{32}$P]ATP in 30 µl of kinase buffer. The reactions were terminated with Laemmli sample buffer and the products were resolved by SDS-PAGE (10% gel). JNK1 phosphorylates GST-ATF2 fusion proteins containing residues 1–505, 1–349, 1–109, 20–109, and 40–109, but not 60–109. These results indicate that the presence of ATF2 residues 1–60 are required for phosphorylation by JNK.

The binding of immobilized GST-ATF2 fusion proteins was examined in a solid-phase kinase assay as described by Hibi et al. (1993) Genes Dev. 7:2135, herein specifically incorporated by reference. JNK1 from UV-irradiated cells was incubated with GST-ATF2 fusion proteins bound to GSH-agarose. The agarose beads were washed extensively to remove the unbound JNK1. Phosphorylation of the GST-ATF2 fusion proteins by the bound JNK1 protein kinase was examined by addition of [γ-$^{32}$P]ATP. JNK1 bound GST-ATF2 fusion proteins containing residues 1–505, 1–349, 1–109, 20–109, and 40–109, indicating that the presence of residues 20–60 were required for binding of JNK1 to ATF2.

EXAMPLE 9
Phosphorylation of the NH$_2$-terminal Activation Domain of ATF2 on Thr$^{69}$ and Thr$^{71}$ by JNK1

The effect of UV radiation on the properties of wild-type (Thr$^{69,71}$) and phosphorylation-defective (Ala$^{69,71}$) ATF2 molecules was examined. Mock-transfected and JNK1-transfected COS cells were treated without and with 40 J/m$^2$ UV radiation. The epitope-tagged JNK1 was isolated by immunoprecipitation with the M2 monoclonal antibody. The phosphorylation of GST-ATF2 (residues 1 to 109) was examined in an immunocomplex kinase assay as described above. The GST-ATF2 was resolved from other proteins by SDS-PAGE and stained with Coomassie blue. The phosphorylation of GST-ATF2 was detected by autoradiography. JNK1-transfected cells, but not mock-transfected cells, phosphorylated ATF2. JNK1 phosphorylation of ATF2 was greater in cells exposed to UV radiation. Phosphorylation of ATF2 by JNK1 was associated with a decreased electrophoretic mobility.

In a separate experiment, GST fusion proteins containing full-length ATF2 (residues 1 to 505), an NH$_2$-terminal fragment (residues 1 to 109), and a COOH-terminal fragment (residues 95 to 505) were phosphorylated with JNK1 and the sites of phosphorylation analyzed by phosphoamino acid analysis. The methods used for phosphopeptide mapping and phosphoamino acid analysis have been described (Alvarez et al. (1991) J. Biol. Chem 266:15277). The horizontal dimension of the peptide maps was electrophoresis and the vertical dimension was chromatography. The NH$_2$-terminal sites of phosphorylation were identified as Thr$^{69}$ and Thr$^{71}$ by phosphopeptide mapping and mutational analysis. Site-directed mutagenesis was performed as described above, replacing Thr$^{69}$ and Thr$^{71}$ with Ala. Phosphorylation of mutated ATF2 was not observed.

EXAMPLE 10
Reduced Electrophoretic Mobility of JNK-Activated ATF2

CHO cells were maintained in Ham's F12 medium supplemented with 5% bovine serum albumin (Gibco-BRL). Cells were labeled and transfected with JNK1 as described above. CHO cells were treated with UV-C (40 J/m$^2$), IL-1α (10 ng/ml) (Genzyme), or fetal bovine serum (20%) (Gibco-BRL). The cells were incubated for 30 minutes at 37° C. prior to harvesting. The electrophoretic mobility of ATF2 after SDS-PAGE was examined by protein immuno-blot analysis. A shift in ATF2 electrophoretic mobility was observed in cells treated with UV, IL-1, and serum. These results indicate that JNK1 activation is associated with an electrophoretic mobility shift of ATF2, further suggesting that ATF2 is an in vivo substrate for JNK1.

EXAMPLE 11
Increased ATF2 Phosphorylation After Activation of JNK

COS-1 cells were transfected without (control) and with an ATF2 expression vector (ATF2), as described above (Hai et al. (1989) supra). The effect of exposure of the cells to 40 J/m$^2$ UV-C was examined. After irradiation, the cells were incubated for 0 or 30 minutes (control) or 0, 15, 30, and 45 minutes (ATF2) at 37° C. and then collected. The electrophoretic mobility of ATF2 during SDS-PAGE was examined by protein immuno-blot analysis as described above. The two electrophoretic mobility forms of ATF2 were observed in ATF2-transfected cells, but not in control cells.

The phosphorylation state of wild-type (Thr$^{69,71}$) ATF2 and mutated (Ala$^{69,71}$) ATF2 was examined in cells labeled with [$^{32}$P], treated without and with 40 J/m$^2$ UV-C, and then incubated at 37° C. for 30 minutes (Hai et al. (1989) supra). The ATF2 proteins were isolated by immunoprecipitation and analyzed by SDS-PAGE and autoradiography. The phosphorylated ATF2 proteins were examined by phosphoamino acid analysis as described above. Both forms of ATF2 contained phosphoserine, but only wild-type ATF2 contained phosphothreonine.

Tryptic phosphopeptide mapping was used to compare ATF2 phosphorylated in vitro by JNK1 with ATF2 phosphorylated in COS-1cells. A map was also prepared with a sample composed of equal amounts of in vivo and in vitro phosphorylated ATF2 (Mix). Mutation of ATF2 at Thr$^{69}$ and Thr$^{71}$ resulted in the loss of two tryptic phosphopeptides in maps of ATF2 isolated from UV-irradiated cells. These phosphopeptides correspond to mono- and bis-phosphorylated peptides containing Thr$^{69}$ and Thr$^{71}$. Both of these phosphopeptides were found in maps of ATF2 phosphorylated by JNK1 in vitro.

EXAMPLE 12
Inhibition of ATF2-Stimulated Gene Expression by Mutation of the Phosphorylation Sites Thr$^{69}$ and Thr$^{71}$ A fusion protein consisting of ATF2 and the GAL4 DNA binding domain was expressed in CHO cells as described above. The activity of the GAL4-ATF2 fusion protein was measured in co-transfection assays with the reporter plasmid pG5E1bLuc (Seth et al. (1992) J. Biol. Chem 267:24796, hereby specifically incorporated by reference). The reporter plasmid contains five GAL4 sites cloned upstream of a minimal promoter element and the firefly luciferase gene. Transfection efficiency was monitored with a control plasmid that expresses β-galactosidase (pCH110; Pharmacia-LKB Biotechnology). The luciferase and β-galactosidase activity detected in cell extracts was measured as the mean activity ratio of three experiments (Gupta et al. (1993) Proc. Natl. Acad. Sci. USA 90:3216, hereby specifically incorporated by reference). The results, shown in Table 1, demonstrate the importance of phosphorylation at Thr$^{69}$ and Thr$^{71}$ for transcriptional activity.

TABLE 1

INHIBITION OF ATF-2 STIMULATED GENE EXPRESSION BY MUTATION OF THE PHOSPHORYLATION SITES THR$^{69,71}$

| PROTEIN | LUCIFERASE ACTIVITY (Light Units/OD) |
| --- | --- |
| GAL4 | 45 |
| GAL4-ATF2 (wild type) | 320,000 |
| GAL4-ATF2 (Ala$^{69}$) | 24,000 |
| GAL4-ATF2 (Ala$^{71}$) | 22,000 |
| GAL4-ATF2 (Ala$^{69,71}$) | 29,000 |
| GAL4-ATF2 (Glu$^{69}$) | 27,000 |

EXAMPLE 13
Effect of Dominant-Negative JNK1 Mutant on ATF2 Function

The luciferase reporter plasmid system was used to determine the effect of point mutations at the ATF2 phosphorylation sites Thr$^{69}$ and Thr$^{71}$ in serum-treated CHO cells transfected with wild-type (Thr$^{183}$, Tyr$^{185}$) or mutant (Ala$^{183}$, Phe$^{185}$) JNK1. Control experiments were done with mock-transfected cells. The CHO cells were serum-starved for 18 hours and then incubated without or with serum for 4 hours. Expression of wild-type ATF2 caused a small increase in serum-stimulated ATF2 transcriptional activity. In contrast, mutant JNK1 inhibited both control and serum-stimulated ATF2 activity.

EXAMPLE 14
Effect of Tumor Suppressor Gene Product Rb and Adenovirus Oncoprotein E1A on ATF2-Stimulated Gene Expression The effect of expression of the Rb tumor suppressor gene product and adenovirus oncoprotein E1A on ATF2 transcriptional activity were investigated with a luciferase reporter plasmid and GAL4-ATF2 (residues 1-505), as described above. Cells were transfected with wild-type (Thr$^{69,71}$) or mutated (Ala$^{69,71}$) ATF2. No effect of Rb or E1A on luciferase activity was detected in the absence of GAL4-ATF2. Rb and E1A were found to increase ATF2-stimulated gene expression of both wild-type and mutated ATF2. However, mutated ATF2 caused a lower level of reporter gene expression than did wild-type ATF2. These results indicate a requirement for ATF2 phosphorylation (on Thr$^{69}$ and Thr$^{71}$) plus either Rb or E1A for maximal transcriptional activity.

EXAMPLE 15
Substrate Specificity of p38 MAP Kinase

Substrate phosphorylation by p38 MAP kinase was examined by incubation of bacterially-expressed p38 MAP kinase with IκB, cMyc, EGF-R, cytoplasmic phospholipase $A_2$ (cPLA$_2$), c-Jun, and mutated ATF2 (Thr$^{69,71}$) and ATP[γ-$^{32}$P] (Raingeaud et al. (1995) J. Biol. Chem 270:7420, herein specifically incorporated by reference). GST-IκB was provided by Dr D. Baltimore (Massachusetts Institute of Technology). GST-cMyc (Alvarez et al. (1991) J. Biol. Chem. 266:15277), GST-EGF-R (residues 647–688) (Koland et al. (1990) Biochem. Biophys. Res. Commun. 166:90), and GST-c-Jun (Dérijard et al. (1994) supra) have been described. The phosphorylation reaction was terminated after 30 minutes by addition of Laemmli sample buffer. The phosphorylated proteins were resolved by SDS-PAGE and detected by autoradiography. The rate phosphorylation of the substrate proteins was quantitated by Phosphorimager (Molecular Dynamics Inc.) analysis. The relative phosphorylation of ATF2, MBP, EGF-R, and IκB was 1.0, 0.23, 0.04, and 0.001,respectively.

EXAMPLE 16
Binding of p38 MAP Kinase to ATF2

Cell extracts expressing epitope-tagged JNK1 and p38 MAP kinase were incubated with a GST fusion protein containing the activation domain of ATF2 (residues 1–109) immobilized on GSH agarose. The supernatant was removed and the agarose was washed extensively. Western blot analysis of the supernatant and agarose-bound fractions was conducted as follows: proteins were fractionated by SDS-PAGE, electrophoretically transferred to an Immobilon-P membrane, and probed with monoclonal antibodies to phosphotyrosine (PY20) and the Flag epitope (M2). immunocomplexes were detected using enhanced chemiluminescence (Amersham International PLC). Control experiments were performed using immobilized GST.

EXAMPLE 17
p38 MAP Kinase and JNK1 Activation by Pro-Inflammatory Cytokines and Environmental Stress The effect of phorbol ester, EGF, UV radiation, osmotic stress, IL-1, tumor necrosis factor (TNF), and LPS on p38 MAP kinase and JNK1 activity were measured in immunecomplex protein kinase assays using ATP[γ-$^{32}$2P] and ATF2 as substrates. TNFα and IL-1α were from Genzyme Corp. Lipolysaccharide (LPS) was isolated from lyophilized Salmonella minesota Re595 bacteria as described (Mathison et al. (1988) J. Clin. Invest. 81:1925). Phorbol myristate acetate was from Sigma. EGF was purified from mouse salivary glands (Davis (1988) J. Biol. Chem 263:9462). Kinase assays were performed using immunoprecipitates of p38 and JNK. The immunocomplexes were washed twice with kinase buffer (described above), and the assays initiated by the addition of 1 µg of ATF2 and 50 µM [γ-$^{32}$P]ATP (10 Ci/mmol) in a final volume of 25 µl. The reactions were terminated after 30 minutes at 30° C. by addition of Laemmli sample buffer. The phosphorylation of ATF2 was examined after SDS-PAGE by autoradiography, and the rate of ATF2 phosphorylation quantitated by PhosphorImager analysis.

The results are shown in Table 2. Exposure of HeLa cells to 10 nM phorbol myristate acetate very weakly activated p38 and JNK1. Similarly, treatment with 10 nM EGF only weakly activated p38 and JNK1. By contrast, treatment with 40 J/m$^2$ UV-C, 300 mM sorbitol, 10 ng/ml interleukin-1, and 10 ng/ml TNFα strongly activated p38 and JNK1 activity. The effect of LPS on the activity of p38 was examined using CHO cells that express human CD14. Exposure of CHO cells to 10 ng/ml LPS only slightly activated p38 and JNK1 activity.

TABLE 2 p38 AND JNK1 ACTIVATION BY PRO-INFLAMMATORY CYTOKINES AND ENVIRONMENTAL STRESS.

|  | Relative Protein Kinase Activity | |
| --- | --- | --- |
|  | JNK | p38 |
| Control | 1.0 | 1.0 |
| Epidermal Growth Factor (10 nM) | 1.9 | 2.1 |
| Phorbol Ester (10 nM) | 2.3 | 2.9 |
| Lipopolysaccharide (10 ng/ml) | 3.6 | 3.7 |
| Osmotic Shock (300 mM sorbitol) | 18.1 | 4.2 |
| Tumor Necrosis Factor (10 ng/ml) | 19.3 | 10.3 |
| Interleukin-1 (10 ng/ml) | 8.9 | 6.2 |
| UV (40 J/m$^2$) | 7.4 | 17.1 |

EXAMPLE 18
p38 MAP Kinase Activation by Dual Phosphorylation on Tyr and Thr

COS-1 cells expressing wild-type (Thr$^{180}$, Tyr$^{182}$) or mutated (Ala$^{180}$, Phe$^{182}$) p38 MAP kinase were treated without and with UV-C (40 J/m$^2$). The cells were harvested 30 minutes following exposure with or without UV radiation. Control experiments were performed using mock-transfected cells. The level of expression of epitope-tagged p38 MAP kinase and the state of Tyr phosphorylation of p38 MAP kinase was examined by Western blot analysis using the M2 monoclonal antibody and the phosphotyrosine monoclonal antibody PY20. Immune complexes were detected by enhanced chemiluminescence.

Wild-type and mutant p38 were expressed at similar levels. Western blot analysis showed that UV radiation caused an increase in the Tyr phosphorylation of p38. The increased Tyr phosphorylation was confirmed by phospho-amino acid analysis of p38 isolated from [$^{32}$P]phosphate-labeled cells. The results also showed that UV radiation increased Thr phosphorylation of p38. The increased phosphorylation on Tyr and Thr was blocked by mutated p38. Wild-type and mutated p38 were isolated from the COS-1 cells by immunoprecipitation. Protein kinase activity was measured in the immune complex using [γ-$^{32}$P]ATP and GST-ATF2 as substrates. The phosphorylated GST-ATF2 was detected after SDS-PAGE by autoradiography. UV radiation resulted in a marked increase in the activity of wild-type p38, while the mutant p38 was found to be catalytically inactive. These results show that p38 is activated by dual phosphorylation within the Thr-Gly-Tyr motif.

EXAMPLE 19
MAP Kinase Phosphatase Inhibits p38 MAP kinase Activation

The cells were treated without and with 40J/m² UV-C. Control experiments were performed using mock-transfected cells (control) and cells transfected with the catalytically inactive mutated phosphatase mPAC1 (Cys$^{257}$/Ser) and human MKP1. The activity of p38 MAP kinase was measured with an immunecomplex protein kinase assay employing [γ-$^{32}$P]ATP and GST-ATF2 as substrates. The expression of PAC1 or MKP1 was found to inhibit p38 phosphorylation, demonstrating that p38 can be regulated by the dual specificity phosphatases PAC1 and MKP1.

EXAMPLE 20
Subcellular Distribution of p38 MAP Kinase

Epitope-tagged p38 MAP kinase was expressed in COS cells. The cells were treated without or with 40 J/m² UV radiation and then incubated for 60 minutes at 37° C. The p38 MAP kinase was detected by indirect immunofluorescence using the M2 monoclonal antibody. The images were acquired by digital imaging microscopy and processed for image restoration.

Immunocytochemistry. Coverslips (22 mm×22 mm No. 1; Gold Seal Cover Glass; Becton-Dickinson) were pre-treated by boiling in 0.1N HCl for 10 minutes, rinsed in distilled water, autoclaved and coated with 0.01% poly-L-lysine (Sigma; St. Louis Mo.). The coverslips were placed at the bottom of 35 mm multiwell tissue culture plates (Becton Dickinson, UK). Transfected COS-1 cells were plated directly on the coverslips and allowed to adhere overnight in Dulbecco's modified Eagle's medium supplemented with 5% fetal calf serum (Gibco-BRL). 24 hours post-transfection, the cells were rinsed once and incubated at 37° C. for 30 minutes in 25 mM Hepes, pH 7.4, 137 mM NaCl, 6 mM KCl, 1 mM MgCl$_2$, 1 mM CaCl$_2$, 10 mM glucose. The cells were rinsed once with phosphate-buffered saline and the coverslips removed from the tissue culture wells. Cells were fixed in fresh 4% paraformaldehyde in phosphate-buffered saline for 15 minutes at 22° C. The cells were permeabilized with 0.25% Triton X-100 in phosphate-buffered saline for 5 minutes and washed three times in DWB solution (150 mM NaCl, 15 mM Na citrate, pH 7.0, 2% horse serum, 1% (w/v) bovine serum albumin, 0.05% Triton X-100) for 5 minutes. The primary antibody (M2 anti-FLAG monoclonal antibody, Eastman-Kodak Co., New Haven, Conn.) was diluted 1:250 in DWB and applied to the cells in a humidified environment at 22° C. for 1 hour. The cells were again washed three times as above and fluorescein isothiocyanate-conjugated goat anti-mouse Ig secondary antibody (Kirkegaard & Perry Laboratories Inc. Gaithersburg, Md.) was applied at a 1:250 dilution for 1 hour at 22° C. in a humidified environment. The cells were then washed three times in DWB and then mounted onto slides with Gel-Mount (Biomeda Corp. Foster City, Calif.) for immunofluorescence analysis. Control experiments were performed to assess the specificity of the observed immunofluorescence. No fluorescence was detected when the transfected cells were stained in the absence of the primary M2 monoclonal antibody, or mock-transfected cells.

Digital Imaging Microscopy and Image Restoration

Digital images of the fluorescence distribution in single cells were obtained using a Nikon 60× Planapo objective (numerical aperture=1.4) on a Zeiss IM-35 microscope equipped for epifluorescence as previously described (Carrington et al. (1990) in: Non-invasive Techniques in Cell Biology (Fosbett & Grinstein, eds.), Wiley-Liss, N.Y.; pp. 53-72; Fay et al. (1989) J. Microsci. 153:133-149). Images of various focal planes were obtained with a computer controlled focus mechanism and a thermoelectrically cooled charged-coupled device camera (model 220; Photometrics Ltd., Tucson, Ariz.). The exposure of the sample to the excitation source was determined by a computer-controlled shutter and wavelength selector system (MVI, Avon, Mass.). The charge-coupled device camera and microscope functions were controlled by a microcomputer, and the data acquired from the camera were transferred to a Silicon Graphics model 4D/GTX workstation (Mountainview, Calif.) for image processing. Images were corrected for non-uniformities in sensitivity and for the dark current of the charge coupled device detector. The calibration of the microscopy blurring was determined by measuring the instrument's point spread function as a series of optical sections at 0.125 μm intervals of a 0.3 μm diameter fluorescently labeled latex bead (Molecular Probes Inc.). The image restoration algorithm used is based upon the theory of ill-posed problems and obtains quantitative dye density values within the cell that are substantially more accurate than those in an un-processed image (Carrington et al. (1990) supra; Fay et al. (1989) supra). After image processing, individual optical sections of cells were inspected and analyzed using computer graphics software on a Silicon Graphics workstation. p38 MAP kinase was observed at the cell surface, in the cytoplasm, and in the nucleus. After irradiation, an increased localization of cytoplasmic p38 to the perinuclear region was detected.

EXAMPLE 21
Activation of the MKK Signal Transduction Pathway by Osmotic Shock CHO cells were co-transfected with the plasmid pCMV-Flag-Jnk1 and pRSV-Neo (Dérijard et al. (1994) supra). A stable cell line expressing epitope-tagged Jnk1 (Flag; Immunex Corp.) was isolated by selection with Geneticin (Gibco-BRL). The cells were incubated with 0, 100, 150, 300, 600, or 1000 mM sorbitol for 1 hour at 37° C. The cells were collected in lysis buffer (20 mM Tris, pH 7.4, 1% Triton X-100, 2 mM EDTA, 137 mM NaCl, 25 mM β-glycerophosphate, 1 mM orthovanadate, 2 mM pyrophosphate, 10% glycerol, 1 mM phenylmethylsulfonylfluoride, 10 μg/ml leupeptin) and a soluble extract was obtained by centrifugation at 100,000 g for 30 minutes at 4° C. The epitope-tagged JNK1 was isolated by immunoprecipitation with the monoclonal antibody M2 (Immunex Corp.). The immunoprecipitates were washed extensively with lysis buffer. Immunocomplex kinase assays were done in 25 μl of 25 mM Hepes, pH 7.4, 25 mM MgCl$_2$, 25 mM β-glycerophosphate, 2 mM dithiothreitol, 100 μM orthovanadate, and 50 μM ATF [γ-$^{32}$p] (10 Ci/mmole) with 2.5 μg of bacterially expressed c-Jun (residues 1-79) fused to glutathione-S-transferase (GST) as a substrate. The phosphorylation of c-Jun was examined after SDS-PAGE by autoradiography and PhosphorImager (Molecular Dynamics Inc.) analysis. JNK1 activation was observed at all concentrations of sorbitol exposure.

The time course of JNK1 protein kinase activation was measured in cells incubated in medium supplemented with 300 mM sorbitol as described above. Increased JNK1 activity was observed within 5 minutes of exposure to sorbitol, with maximum activity occurring after 15-30 minutes.

Mutation of JNK1 at the phosphorylation sites Thr$^{183}$ and Tyr$^{185}$ blocked the activation of JNK1 protein kinase activity by osmotic shock. CHO cells were transfected with vector, wild-type JNK1 (Thr$^{183}$, Tyr$^{185}$), and mutated JNK1 (Ala$^{183}$, Phe$^{185}$). The cells were incubated in medium supplemented without or with 300 mM sorbitol for 15 minutes before measurement of JNK1 protein kinase activity as described above. JNK1 activation was seen in the wild-type but not mutated JNK1.

Use

The MKK polypeptides and polynucleotides of the invention are useful for identifying reagents which modulate the MKK signal transduction pathways. Reagents that modulate an MKK signal transduction pathway can be identified by their effect on MKK synthesis, MKK phosphorylation, or MKK activity. For example, the effect of a reagent on MKK activity can be measured by the in vitro kinase assays described above. MKK is incubated without (control) and with a test reagent under conditions sufficient to allow the components to react, then the effect of the test reagent on kinase activity is subsequently measured. Reagents that inhibit an MKK signal transduction pathway can be used in the treatment of MKK-mediated disorders. Reagents that stimulate an MKK signal transduction pathway can be used in a number of ways, including induction of programmed cell death (apoptosis) in tissues. For example, the elimination of UV damaged cells can be used to prevent cancer.

Generally, for identification of a reagent that inhibits the MKK signal transduction pathway, the kinase assay is tested with a range of reagent concentrations, e.g., 1.0 nM to 100 mM, a MKK substrate, and a radioactive marker such as [$\gamma$-$^{32}$P]ATP. Appropriate substrate molecules include p38, JNK1, JNK2, or ATF2. The incorporation of [$^{32}$P] into the substrate is determined, and the results obtained with the test reagent compared to control values. Of particular interest are reagents that result in inhibition of [$^{32}$P] of about 80% or more.

Assays that test the effect of a reagent on MKK synthesis can also be used to identify compounds that inhibit MKK signal transduction pathways. The effect of the test reagent on MKK expression is measured by, for example, Western blot analysis with an antibody specific for MKK. Antibody binding is visualized by autoradiography or chemiluminescence, and is quantitated. The effect of the test reagent on MKK mRNA expression can be examined, for example, by Northern blot analysis using a polynucleotide probe or by polymerase chain reaction.

Reagents found to inhibit MKK signal transduction pathways can be used as therapeutic agents for the treatment of MKK-mediated disorders. Such reagents are also useful in drug design for elucidation of the specific molecular features needed to inhibit MKK signal transduction pathways.

In addition, the invention provides a method for the treatment of MKK-mediated stress-related and inflammatory disorders. The method includes administration of an effective amount of a therapeutic reagent that inhibits MKK function. Suitable reagents inhibit either MKK activity or expression. The concentration of the reagent to be administered is determined based on a number of factors, including the appropriate dosage, the route of administration, and the specific condition being treated. The appropriate dose of a reagent is determined by methods known to those skilled in the art including routine experimentation to optimize the dosage as necessary for the individual patient and specific MKK-mediated disorder being treated. Specific therapeutically effective amounts appropriate for administration are readily determined by one of ordinary skill in the art (see, for example, *Remington's Pharmaceutical Sciences*. 18th ed., Gennaro, ed., Mack Publishing Company, Easton, Pa., 1990).

The invention provides methods for both acute and prophylactic treatment of stress-related and inflammatory disorders. For example, it is envisioned that ischemic heart disease will be treated during episodes of ischemia and oxidative stress following reperfusion. In addition, a patient at risk for ischemia can be treated prior to ischemic episodes.

In another example, a therapeutic agent which inhibits MKK function or activity is administered to control inflammatory responses by inhibiting the secretion of inflammatory cytokines, including TNF and IL-1.

Stress-related proliferative disorders can also be treated by the method of the invention by administering a therapeutic reagent that inhibits MKK function or activity. Such therapeutic reagents can be used alone or in combination with other therapeutic reagents, for example, with chemotherapeutic agents in the treatment of malignancies. Indeed, the control of stress-activated MKK by the therapeutic reagents provided by this invention can modulate symptoms caused by other therapeutic strategies that induce stress.

The therapeutic reagents employed are compounds which inhibit MKK function or activity, including polynucleotides, polypeptides, and other molecules such as antisense oligonucleotides and ribozymes, which can be made according to the invention and techniques known to the art. Polyclonal or monoclonal antibodies (including fragments or derivatives thereof) that bind epitopes of MKK also can be employed as therapeutic reagents. Dominant-negative forms of MKK which effectively displace or compete with MKK for substrate binding and/or phosphorylation can be used to decrease protein kinase activity. Dominant-negative forms can be created by mutations within the catalytic domain of the protein kinases, as described above.

In some cases, augmentation of MKK activity is desirable, e.g., induction of apoptosis. The methods of the invention can be used to identify reagents capable of increasing MKK function or activity. Alternatively, increased activity is achieved by over-expression of MKK. When a MKK-mediated disorder is associated with underexpression of MKK, or expression of a mutant MKK polypeptide, a sense polynucleotide sequence (the DNA coding strand) or MKK polypeptide can be introduced into the cell.

The antibodies of the invention can be administered parenterally by injection or by gradual infusion over time. The monoclonal antibodies of the invention can be administered intravenously, intraperitoneally, intramuscularly, subcutaneously, intracavity, or transdermally.

Preparations for parenteral administration of a polypeptide or an antibody of the invention include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose) and the like. Preservatives and other additives can also be present, such as, for example, antimicrobials, antioxidants, chelating agents, and inert gases, and the like.

Polynucleotide sequences, including antisense sequences, can be therapeutically administered by various techniques known to those skilled in the art. Such therapy would achieve its therapeutic effect by introduction of the MKK polynucleotide into cells of mammals having a MKK-mediated disorder. Delivery of MKK polynucleotides can be achieved using free polynucleotide or a recombinant expression vector such as a chimeric virus or a colloidal dispersion system. Especially preferred for therapeutic delivery of nucleotide sequences is the use of targeted liposomes.

Targeting of the therapeutic reagent to specific tissues is desirable to increase the efficiency of delivery. The targeting can be achieved by passive mechanisms via the route of administration. Active targeting to specific tissues can also be employed. The use of liposomes, colloidal suspensions, and viral vectors allows targeting to specific tissues by changing the composition of the formulation containing the therapeutic reagent, for example, by including molecules that act as receptors for components of the target tissues. Examples include sugars, glycoplipids, polynucleotides, or proteins. These molecules can be included with the therapeutic reagent. Alternatively, these molecules can be included by indirect methods, for example, by inclusion of a polynucleotide that encodes the molecule, or by use of packaging systems that provide targeting molecules. Those skilled in the art will know, or will ascertain with the use of the teaching provided herein, which molecules and procedures will be useful for delivery of the therapeutic reagent to specific tissues.

Other Embodiments

It is to be understood that while the invention has been described in conjunction with the detailed description thereof, that the foregoing description is intended to illustrate and not limit the scope of the invention, which is defined by the scope of the appended claims. Other aspects, advantages, and modifications are within the scope of the following claims.

SEQUENCE LISTING ( 1 ) GENERAL INFORMATION:

( i i i ) NUMBER OF SEQUENCES: 16

( 2 ) INFORMATION FOR SEQ ID NO:1:

( i ) SEQUENCE CHARACTERISTICS:
        ( A ) LENGTH: 2030 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1:

```
TGGCTGGCAA  TGGCCTTGCT  GACCTCGAGC  CGGGCCCACG  TGGGGACCTT  TGGAGCACAG      60
CCTACGATCC  TGGTGCAAGG  CCGGTGGATG  CAGAGGCCAG  TCCATATACC  ACCCAGGCCT     120
GCGAGGAGCG  TGGTCCCCAC  CCATCCAGCC  CATATGTGCA  AGTGCCCTTG  ACAGAGAGGC     180
TGGTCATATC  CATGGTGACC  ATTTATGGGC  CACAACAGGT  CCCCATCTGC  GCAGTGAACC     240
CTGTGCTGAG  CACCTTGCAG  ACGTGATCTT  GCTTCGTCCT  GCAGCACTGT  GCGGGGCAGG     300
AAAATCCAAG  AGGAAGAAGG  ATCTACGGAT  ATCCTGCATG  TCCAAGCCAC  CCGCACCCAA     360
CCCCACACCC  CCCCGGAACC  TGGACTCCCG  GACCTTCATC  ACCATTGGAG  ACAGAAACTT     420
TGAGGTGGAG  GCTGATGACT  TGGTGACCAT  CTCAGAACTG  GGCCGTGGAG  CCTATGGGGT     480
GGTAGAGAAG  GTGCGGCACG  CCCAGAGCGG  CACCATCATG  GCCGTGAAGC  GGATCCGGGC     540
CACCGTGAAC  TCACAGGAGC  AGAAGCGGCT  GCTCATGGAC  CTGGACATCA  ACATGCGCAC     600
GGTCGACTGT  TTCTACACTG  TCACCTTCTA  CGGGGCACTA  TTCAGAGAGG  GAGACGTGTG     660
GATCTGCATG  GAGCTCATGG  ACACATCCTT  GGACAAGTTC  TACCGGAAGG  TGCTGGATAA     720
AAACATGACA  ATTCCAGAGG  ACATCCTTGG  GGAGATTGCT  GTGTCTATCG  TGCGGGCCCT     780
GGAGCATCTG  CACAGCAAGC  TGTCGGTGAT  CCACAGAGAT  GTGAAGCCCT  CCAATGTCCT     840
TATCAACAAG  GAGGGCCATG  TGAAGATGTG  TGACTTTGGC  ATCAGTGGCT  ACTTGGTGGA     900
CTCTGTGGCC  AAGACGATGG  ATGCCGGCTG  CAAGCCCTAC  ATGGCCCCTG  AGAGGATCAA     960
CCCAGAGCTG  AACCAGAAGG  GCTACAATGT  CAAGTCCGAC  GTCTGGAGCC  TGGGCATCAC    1020
CATGATTGAG  ATGGCCATCC  TGCGGTTCCC  TTACGAGTCC  TGGGGACCC   CGTTCCAGCA    1080
GCTGAAGCAG  GTGGTGGAGG  AGCCGTCCCC  CCAGCTCCCA  GCCGACCGTT  TCTCCCCCGA    1140
GTTTGTGGAC  TTCACTGCTC  AGTGCCTGAG  GAAGAACCCC  GCAGAGCGTA  TGAGCTACCT    1200
```

-continued

| | | | | | |
|---|---|---|---|---|---|
| GGAGCTGATG | GAGCACCCCT | TCTTCACCTT | GCACAAAACC | AAGAAGACGG | ACATTGCTGC | 1260
| CTTCGTGAAG | AAGATCCTGG | GAGAAGACTC | ATAGGGGCTG | GGCCTCGGAC | CCCACTCCGG | 1320
| CCCTCCAGAG | CCCCACAGCC | CCATCTGCGG | GGGCAGTGCT | CACCCACACC | ATAAGCTACT | 1380
| GCCATCCTGG | CCCAGGGCAT | CTGGGAGGAA | CCGAGGGGGC | TGCTCCCACC | TGGCTCTGTG | 1440
| GCGAGCCATT | TGTCCCAAGT | GCCAAGAAG | CAGACCATTG | GGCTCCCAG | CCAGGCCCTT | 1500
| GTCGGCCCCA | CCAGTGCCTC | TCCCTGCTGC | TCCTAGGACC | CGTCTCCAGC | TGCTGAGATC | 1560
| CTGGACTGAG | GGGGCCTGGA | TGCCCCCTGT | GGATGCTGCT | GCCCTGCAC | AGCAGGCTGC | 1620
| CAGTGCCTGG | GTGGATGGGC | CACCGCCTTG | CCCAGCCTGG | ATGCCATCCA | AGTTGTATAT | 1680
| TTTTTAATC | TCTCGACTGA | ATGGACTTTG | CACACTTTGG | CCCAGGGTGG | CCACACCTCT | 1740
| ATCCCGGCTT | TGGTGCGGGG | TACACAAGAG | GGGATGAGTT | GTGTGAATAC | CCCAAGACTC | 1800
| CCATGAGGGA | GATGCCATGA | GCCGCCCAAG | GCCTTCCCCT | GGCACTGGCA | AACAGGGCCT | 1860
| CTGCGGAGCA | CACTGGCTCA | CCCAGTCCTG | CCCGCCACCG | TTATCGGTGT | CATTCACCTT | 1920
| TCGTGTTTTT | TTTAATTTAT | CCTCTGTTGA | TTTTTTCTTT | TGCTTTATGG | GTTTGGCTTG | 1980
| TTTTTCTTGC | ATGGTTTGGA | GCTGATCGCT | TCTCCCCCAC | CCCCTAGGGG | | 2030

( 2 ) INFORMATION FOR SEQ ID NO:2:

( i ) SEQUENCE CHARACTERISTICS:
        ( A ) LENGTH: 318 amino acids
        ( B ) TYPE: amino acid
        ( C ) STRANDEDNESS: Not Relevant
        ( D ) TOPOLOGY: linear ( x i ) SEQUENCE DESCRIPTION: SEQ ID NO:2:

```
Met Ser Lys Pro Pro Ala Pro Asn Pro Thr Pro Pro Arg Asn Leu Asp
 1               5                  10                  15

Ser Arg Thr Phe Ile Thr Ile Gly Asp Arg Met Phe Glu Val Glu Ala
             20                  25                  30

Asp Asp Leu Val Thr Ile Ser Glu Leu Gly Arg Gly Ala Tyr Gly Val
         35                  40                  45

Val Glu Lys Val Arg His Ala Gln Ser Gly Thr Ile Met Ala Val Lys
     50                  55                  60

Arg Ile Arg Ala Thr Val Asn Ser Gln Glu Gln Lys Arg Leu Leu Met
 65                  70                  75                  80

Asp Leu Asp Ile Asn Met Arg Thr Val Asp Cys Phe Tyr Thr Val Thr
                 85                  90                  95

Phe Tyr Gly Ala Leu Phe Arg Glu Gly Asp Val Trp Ile Cys Met Glu
            100                 105                 110

Leu Met Asp Thr Ser Leu Asp Lys Phe Tyr Arg Lys Val Leu Asp Lys
        115                 120                 125

Asn Met Thr Ile Pro Glu Asp Ile Leu Gly Glu Ile Ala Val Ser Ile
    130                 135                 140

Val Arg Ala Leu Glu His Leu His Ser Lys Leu Ser Val Ile His Arg
145                 150                 155                 160

Asp Val Lys Pro Ser Asn Val Leu Ile Asn Lys Glu Gly His Val Lys
                165                 170                 175

Met Cys Asp Phe Gly Ile Ser Gly Tyr Leu Val Asp Ser Val Ala Lys
            180                 185                 190

Thr Met Asp Ala Gly Cys Lys Pro Tyr Met Ala Pro Glu Arg Ile Asn
        195                 200                 205

Pro Glu Leu Asn Gln Lys Gly Tyr Asn Val Lys Ser Asp Val Trp Ser
    210                 215                 220
```

| Leu | Gly | Ile | Thr | Met | Ile | Glu | Met | Ala | Ile | Leu | Arg | Phe | Pro | Tyr | Glu |
| 225 | | | | 230 | | | | | 235 | | | | | | 240 |

| Ser | Trp | Gly | Thr | Pro | Phe | Gln | Gln | Leu | Lys | Gln | Val | Val | Glu | Glu | Pro |
| | | | | 245 | | | | | 250 | | | | | 255 | |

| Ser | Pro | Gln | Leu | Pro | Ala | Asp | Arg | Phe | Ser | Pro | Glu | Phe | Val | Asp | Phe |
| | | | 260 | | | | | 265 | | | | | 270 | | |

| Thr | Ala | Gln | Cys | Leu | Arg | Lys | Asn | Pro | Ala | Glu | Arg | Met | Ser | Tyr | Leu |
| | | 275 | | | | | 280 | | | | | 285 | | | |

| Glu | Leu | Met | Glu | His | Pro | Phe | Thr | Leu | His | Lys | Thr | Lys | Lys | Thr |
| | 290 | | | | | 295 | | | | 300 | | | | |

| Asp | Ile | Ala | Ala | Phe | Val | Lys | Lys | Ile | Leu | Gly | Glu | Asp | Ser |
| 305 | | | | | 310 | | | | | 315 | | | |

( 2 ) INFORMATION FOR SEQ ID NO:3:

( i ) SEQUENCE CHARACTERISTICS:
  ( A ) LENGTH: 1602 base pairs
  ( B ) TYPE: nucleic acid
  ( C ) STRANDEDNESS: single
  ( D ) TOPOLOGY: linear ( x i ) SEQUENCE DESCRIPTION: SEQ ID NO:3:

```
TAGCTGCAGC ACAGCCTTCC CTAACGTTGC AACTGGGGGA AAAATCACTT TCCAGTCTGT     60
TTTGCAAGGT GTGCATTTCC ATCTTGATTC CCTGAAAGTC CATCTGCTGC ATCGGTCAAG    120
AGAAACTCCA CTTGCATGAA GATTGCACGC TGCAGCTTG CATCTTTGTT GCAAAACTAG     180
CTACAGAAGA GAAGCAAGGC AAAGTCTTTT GTGCTCCCCT CCCCCATCAA AGGAAAGGGG    240
AAAATGTCTC AGTCGAAAGG CAAGAAGCGA AACCCTGGCC TTAAAATTCC AAAAGAAGCA    300
TTTGAACAAC CTCAGACCAG TTCCACACCA CCTAGAGATT TAGACTCCAA GGCTTGCATT    360
TCTATTGGAA ATCAGAACTT TGAGGTGAAG GCAGATGACC TGGAGCCTAT AATGGAACTG    420
GGACGAGGTG CGTACGGGGT GGTGGAGAAG ATGCGGCACG TGCCCAGCGG GCAGATCATG    480
GCAGTGAAGC GGATCCGAGC CACAGTAAAT AGCCAGGAAC AGAAACGGCT ACTGATGGAT    540
TTGGATATTT CCATGAGGAC GGTGGACTGT CCATTCACTG TCACCTTTTA TGGCGCACTG    600
TTTCGGGAGG GTGATGTGTG GATCTGCATG GAGCTCATGG ATACATCACT AGATAAATTC    660
TACAAACAAG TTATTGATAA AGGCCAGACA ATTCCAGAGG ACATCTTAGG GAAAATAGCA    720
GTTTCTATTG TAAAAGCATT AGAACATTTA CATAGTAAGC TGTCTGTCAT TCACAGAGAC    780
GTCAAGCCTT CTAATGTACT CATCAATGCT CTCGGTCAAG TGAAGATGTG CGATTTTGGA    840
ATCAGTGGCT ACTTGGTGGA CTCTGTTGCT AAAACAATTG ATGCAGGTTG CAAACCATAC    900
ATGGCCCCTG AAAGAATAAA CCCAGAGCTC AACCAGAAGG GATACAGTGT GAAGTCTGAC    960
ATTTGGAGTC TGGGCATCAC GATGATTGAG TTGGCCATCC TTCGATTTCC CTATGATTCA   1020
TGGGGAACTC CATTTCAGCA GCTCAAACAG GTGGTAGAGG AGCCATCGCC ACAACTCCCA   1080
GCAGACAAGT TCTCTGCAGA GTTTGTTGAC TTTACCTCAC AGTGCTTAAA GAAGAATTCC   1140
AAAGAACGGC CTACATACCC AGAGCTAATG CAACATCCAT TTTTCACCCT ACATGAATCC   1200
AAAGGAACAG ATGTGGCATC TTTTGTAAAA CTGATTCTTG GAGACTAAAA AGCAGTGGAC   1260
TTAATCGGTT GACCCTACTG TGGATTGGTG GGTTTCGGGG TGAAGCAAGT TCACTACAGC   1320
ATCAATAGAA AGTCATCTTT GAGATAATTT AACCCTGCCT CTCAGAGGGT TTTCTCTCCC   1380
AATTTTCTTT TTACTCCCCC TCTTAAGGGG GCCTTGGAAT CTATAGTATA GAATGAACTG   1440
TCTAGATGGA TGAATTATGA TAAAGGCTTA GGACTTCAAA AGGTGATTAA ATATTTAATG   1500
```

```
ATGTGTCATA TGAGTCCTCA AAAAAAAAAA AAAAAAAAAA AAAAAAAAAA AAAAAAAAAA        1560

AAAAAAAAAA AAAAAAAAAA AAAAAAAAAA AAAAAAAAAA AA                          1602
```

( 2 ) INFORMATION FOR SEQ ID NO:4:

( i ) SEQUENCE CHARACTERISTICS:
        ( A ) LENGTH: 334 amino acids
        ( B ) TYPE: amino acid
        ( C ) STRANDEDNESS: Not Relevant
        ( D ) TOPOLOGY: linear ( x i ) SEQUENCE DESCRIPTION: SEQ ID NO:4:

```
Met Ser Gln Ser Lys Gly Lys Lys Arg Asn Pro Gly Leu Lys Ile Pro
 1               5                  10                  15

Lys Glu Ala Phe Glu Gln Pro Gln Thr Ser Ser Thr Pro Pro Arg Asp
                20                  25                  30

Leu Asp Ser Lys Ala Cys Ile Ser Ile Gly Asn Gln Asn Phe Glu Val
            35                  40                  45

Lys Ala Asp Asp Leu Glu Pro Ile Met Glu Leu Gly Arg Gly Ala Tyr
 50                  55                  60

Gly Val Val Glu Lys Met Arg His Val Pro Ser Gly Gln Ile Met Ala
 65                  70                  75                  80

Val Lys Arg Ile Arg Ala Thr Val Asn Ser Gln Glu Gln Lys Arg Leu
                 85                  90                  95

Leu Met Asp Leu Asp Ile Ser Met Arg Thr Val Asp Cys Pro Phe Thr
                100                 105                 110

Val Thr Phe Tyr Gly Ala Leu Phe Arg Glu Gly Asp Val Trp Ile Cys
            115                 120                 125

Met Glu Leu Met Asp Thr Ser Leu Asp Lys Phe Tyr Lys Gln Val Ile
130                 135                 140

Asp Lys Gly Gln Thr Ile Pro Glu Asp Ile Leu Gly Lys Ile Ala Val
145                 150                 155                 160

Ser Ile Val Lys Ala Leu Glu His Leu His Ser Lys Leu Ser Val Ile
                165                 170                 175

His Arg Asp Val Lys Pro Ser Asn Val Leu Ile Asn Ala Leu Gly Gln
            180                 185                 190

Val Lys Met Cys Asp Phe Gly Ile Ser Gly Tyr Leu Val Asp Ser Val
        195                 200                 205

Ala Lys Thr Ile Asp Ala Gly Cys Lys Pro Tyr Met Ala Pro Glu Arg
210                 215                 220

Ile Asn Pro Glu Leu Asn Gln Lys Gly Tyr Ser Val Lys Ser Asp Ile
225                 230                 235                 240

Trp Ser Leu Gly Ile Thr Met Ile Glu Leu Ala Ile Leu Arg Phe Pro
                245                 250                 255

Tyr Asp Ser Trp Gly Thr Pro Phe Gln Gln Leu Lys Gln Val Val Glu
            260                 265                 270

Glu Pro Ser Pro Gln Leu Pro Ala Asp Lys Phe Ser Ala Glu Phe Val
        275                 280                 285

Asp Phe Thr Ser Gln Cys Leu Lys Lys Asn Ser Lys Glu Arg Pro Thr
290                 295                 300

Tyr Pro Glu Leu Met Gln His Pro Phe Phe Thr Leu His Glu Ser Lys
305                 310                 315                 320

Gly Thr Asp Val Ala Ser Phe Val Lys Leu Ile Leu Gly Asp
                325                 330
```

( 2 ) INFORMATION FOR SEQ ID NO:5:

( i ) SEQUENCE CHARACTERISTICS:
    ( A ) LENGTH: 3497 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:5:

```
CTAGGGTCCC CGGCGCCAGG CCACCCGGCC GTCAGCAGCA TGCAGGGTAA ACGCAAAGCA      60
CTGAAGTTGA ATTTTGCAAA TCCACCTTTC AAATCTACAG CAAGGTTTAC TCTGAATCCC     120
AATCCTACAG GAGTTCAAAA CCCACACATA GAGAGACTGA GAACACACAG CATTGAGTCA     180
TCAGGAAAAC TGAAGATCTC CCCTGAACAA CACTGGGATT TCACTGCAGA GGACTTGAAA     240
GACCTTGGAG AAATTGGACG AGGAGCTTAT GGTTCTGTCA ACAAAATGGT CCACAAACCA     300
AGTGGGCAAA TAATGGCAGT TAAAAGAATT CGGTCAACAG TGGATGAAAA AGAACAAAAA     360
CAACTTCTTA TGGATTTGGA TGTAGTAATG CGGAGTAGTG ATTGCCCATA CATTGTTCAG     420
TTTTATGGTG CACTCTTCAG AGAGGGTGAC TGTTGGATCT GTATGGAACT CATGTCTACC     480
TCGTTTGATA AGTTTTACAA ATATGTATAT AGTGTATTAG ATGATGTTAT TCCAGAAGAA     540
ATTTTAGGCA AAATCACTTT AGCAACTGTG AAAGCACTAA ACCACTTAAA AGAAAACTTG     600
AAAATTATTC ACAGAGATAT CAAACCTTCC AATATTCTTC TGGACAGAAG TGGAAATATT     660
AAGCTCTGTG ACTTCGGCAT CAGTGGACAG CTTGTGGACT CTATTGCCAA GACAAGAGAT     720
GCTGGCTGTA GGCCATACAT GGCACCTGAA AGAATAGACC CAAGCGCATC ACGACAAGGA     780
TATGATGTCC GCTCTGATGT CTGGAGTTTG GGGATCACAT TGTATGAGTT GGCCACAGGC     840
CGATTTCCTT ATCCAAAGTG GAATAGTGTA TTTGATCAAC TAACACAAGT CGTGAAAGGA     900
GATCCTCCGC AGCTGAGTAA TTCTGAGGAA AGGGAATTCT CCCCGAGTTT CATCAACTTT     960
GTCAACTTGT GCCTTACGAA GGATGAATCC AAAAGGCCAA AGTATAAAGA GCTTCTGAAA    1020
CATCCCTTTA TTTTGATGTA TGAAGAACGT GCCGTTGAGG TCGCATGCTA TGTTTGTAAA    1080
ATCCTGGATC AAATGCCAGC TACTCCCAGC TCTCCCATGT ATGTCGATTG ATATCGTGCT    1140
ACATCAGACT CTAGAAAAAA GGGCTGAGAG GAAGCAAGAC GTAAAGAATT TCATCCCGT    1200
ATCACAGTGT TTTTATTGCT CGCCCAGACA CCATGTGCAA TAAGATTGGT GTTCGTTTCC    1260
ATCATGTCTG TATACTCCTG TCACCTAGAA CGTGCATCCT TGTAATACCT GATTGATCAC    1320
ACAGTGTTAG TGCTGGTCAG AGAGACCTCA TCCTGCTCTT TTGTGATGAA CATATTCATG    1380
AAATGTGGAA GTCAGTACGA TCAAGTTGTT GACTGTGATT AGATCACATC TTAAATTCAT    1440
TTCTAGACTC AAAACCTGGA GATGCAGCTA CTGGAATGGT GTTTGTCAG ACTTCCAAAT    1500
CCTGGAAGGA CACAGTGATG AATGTACTAT ATCTGAACAT AGAAACTCGG GCTTGAGTGA    1560
GAAGAGCTTG CACAGCCAAC GAGACACATT GCCTTCTGGA GCTGGAGAC AAAGGAGGAA    1620
TTTACTTTCT TCACCAAGTG CAATAGATTA CTGATGTGAT ATTCTGTTGC TTTACAGTTA    1680
CAGTTGATGT TTGGGGATCG ATGTGCTCAG CCAAATTTCC TGTTTGAAAT ATCATGTTAA    1740
ATTAGAATGA ATTTATCTTT ACCAAAAACC ATGTTGCGTT CAAAGAGGTG AACATTAAAA    1800
TATAGAGACA GGACAGAATG TGTTCTTTTC TCCTCTACCA GTCCTATTTT TCAATGGGAA    1860
GACTCAGGAG TCTGCCACTT GTCAAGAAG GTGCTGATCC TAAGAATTTT TCATTCTCAG    1920
AATTCGGTGT GCTGCCAACT TGATGTTCCA CCTGCCACAA ACCACCAGGA CTGAAAGAAG    1980
AAAACAGTAC AGAAGGCAAA GTTACAGAT GTTTTAATT CTAGTATTTT ATCTGGAACA    2040
ACTTGTAGCA GCTATATATT TCCCCTTGGT CCCAAGCCTG ATACTTTAGC CATCATAACT    2100
CACTAACAGG GAGAAGTAGC TAGTAGCAAT GTGCCTTGAT TGATTAGATA AAGATTTCTA    2160
```

```
GTAGGCAGCA  AAAGACCAAA  TCTCAGTTGT  TTGCTTCTTG  CCATCACTGG  TCCAGGTCTT   2220
CAGTTTCCGA  ATCTCTTTCC  CTTCCCCTGT  GGTCTATTGT  CGCTATGTGA  CTTGCGCTTA   2280
ATCCAATATT  TTGCCTTTTT  TCTATATCAA  AAAACCTTTA  CAGTTAGCAG  GGATGTTCCT   2340
TACCGAGGAT  TTTTAACCCC  CAATCTCTCA  TAATCGCTAG  TGTTTAAAAG  GCTAAGAATA   2400
GTGGGGCCCA  ACCGATGTGG  TAGGTGATAA  AGAGGCATCT  TTTCTAGAGA  CACATTGGAC   2460
CAGATGAGGA  TCCGAAACGG  CAGCCTTTAC  GTTCATCACC  TGCTAGAACC  TCTCGTAGTC   2520
CATCACCATT  TCTTGGCATT  GGAATTCTAC  TGGAAAAAAA  TACAAAAAGC  AAAACAAAAC   2580
CCTCAGCACT  GTTACAAGAG  GCCATTTAAG  TATCTTGTGC  TTCTTCACTT  ACCCATTAGC   2640
CAGGTTCTCA  TTAGGTTTTG  CTTGGGCCTC  CCTGGCACTG  AACCTTAGGC  TTTGTATGAC   2700
AGTGAAGCAG  CACTGTGAGT  GGTTCAAGCA  CACTGGAATA  TAAAACAGTC  ATGGCCTGAG   2760
ATGCAGGTGA  TGCCATTACA  GAACCAAATC  GTGGCACGTA  TTGCTGTGTC  TCCTCTCAGA   2820
GTGACAGTCA  TAAATACTGT  CAAACAATAA  AGGGAGAATG  GTGCTGTTTA  AAGTCACATC   2880
CCTGTAAATT  GCAGAATTCA  AAAGTGATTA  TCTCTTTGAT  CTACTTGCCT  CATTTCCCTA   2940
TCTTCTCCCC  CACGGTATCC  TAAACTTTAG  ACTTCCCACT  GTTCTGAAAG  GAGACATTGC   3000
TCTATGTCTG  CCTTCGACCA  CAGCAAGCCA  TCATCCTCCA  TTGCTCCCGG  GGACTCAAGA   3060
GGAATCTGTT  TCTCTGCTGT  CAACTTCCCA  TCTGGCTCAG  CATAGGGTCA  CTTTGCCATT   3120
ATGCAAATGG  AGATAAAAGC  AATTCTGGCT  GTCCAGGAGC  TAATCTGACC  GTTCTATTGT   3180
GTGGATGACC  ACATAAGAAG  GCAATTTTAG  TGTATTAATC  ATAGATTATT  ATAAACTATA   3240
AACTTAAGGG  CAAGGAGTTT  ATTACAATGT  ATCTTTATTA  AACAAAAGG   GTGTATAGTG   3300
TTCACAAACT  GTGAAAATAG  TGTAAGAACT  GTACATTGTG  AGCTCTGGTT  ATTTTTCTCT   3360
TGTACCATAG  AAAAATGTAT  AAAAATTATC  AAAAAGCTAA  TGTGCAGGGA  TATTGCCTTA   3420
TTTGTCTGTA  AAAAATGGAG  CTCAGTAACA  TAACTGCTTC  TTGGAGCTTT  GGAATATTTT   3480
ATCCTGTATT  CTTGTTT                                                      3497
```

( 2 ) INFORMATION FOR SEQ ID NO:6:

( i ) SEQUENCE CHARACTERISTICS:
    ( A ) LENGTH: 363 amino acids
    ( B ) TYPE: amino acid
    ( C ) STRANDEDNESS: Not Relevant
    ( D ) TOPOLOGY: linear ( x i ) SEQUENCE DESCRIPTION: SEQ ID NO:6:

```
Met Gln Gly Lys Arg Lys Ala Leu Lys Leu Asn Phe Ala Asn Pro Pro
  1           5                  10                  15
Phe Lys Ser Thr Ala Arg Phe Thr Leu Asn Pro Asn Pro Thr Gly Val
             20                  25                  30
Gln Asn Pro His Ile Glu Arg Leu Arg Thr His Ser Ile Glu Ser Ser
         35                  40                  45
Gly Lys Leu Lys Ile Ser Pro Glu Gln His Trp Asp Phe Thr Ala Glu
     50                  55                  60
Asp Leu Lys Asp Leu Gly Glu Ile Gly Arg Gly Ala Tyr Gly Ser Val
 65                  70                  75                  80
Asn Lys Met Val His Lys Pro Ser Gly Gln Ile Met Ala Val Lys Arg
                 85                  90                  95
Ile Arg Ser Thr Val Asp Glu Lys Glu Gln Lys Gln Leu Leu Met Asp
             100                 105                 110
Leu Asp Val Val Met Arg Ser Ser Asp Cys Pro Tyr Ile Val Gln Phe
```

|   |   |   |   |   | 115 |   |   |   |   | 120 |   |   |   |   | 125 |   |   |
|---|---|---|---|---|---|---|---|---|---|---|---|---|---|---|---|---|---|
| Tyr | Gly | Ala | Leu | Phe | Arg | Glu | Gly | Asp | Cys | Trp | Ile | Cys | Met | Glu | Leu |
|   |   | 130 |   |   |   | 135 |   |   |   | 140 |   |   |   |   |   |
| Met | Ser | Thr | Ser | Phe | Asp | Lys | Phe | Tyr | Lys | Tyr | Val | Tyr | Ser | Val | Leu |
| 145 |   |   |   |   | 150 |   |   |   | 155 |   |   |   |   |   | 160 |
| Asp | Asp | Val | Ile | Pro | Glu | Glu | Ile | Leu | Gly | Lys | Ile | Thr | Leu | Ala | Thr |
|   |   |   |   | 165 |   |   |   |   | 170 |   |   |   |   | 175 |   |
| Val | Lys | Ala | Leu | Asn | His | Leu | Lys | Glu | Asn | Leu | Lys | Ile | Ile | His | Arg |
|   |   |   | 180 |   |   |   |   | 185 |   |   |   |   | 190 |   |   |
| Asp | Ile | Lys | Pro | Ser | Asn | Ile | Leu | Leu | Asp | Arg | Ser | Gly | Asn | Ile | Lys |
|   |   | 195 |   |   |   |   | 200 |   |   |   |   | 205 |   |   |   |
| Leu | Cys | Asp | Phe | Gly | Ile | Ser | Gly | Gln | Leu | Val | Asp | Ser | Ile | Ala | Lys |
|   | 210 |   |   |   |   | 215 |   |   |   |   | 220 |   |   |   |   |
| Thr | Arg | Asp | Ala | Gly | Cys | Arg | Pro | Tyr | Met | Ala | Pro | Glu | Arg | Ile | Asp |
| 225 |   |   |   |   | 230 |   |   |   |   | 235 |   |   |   |   | 240 |
| Pro | Ser | Ala | Ser | Arg | Gln | Gly | Tyr | Asp | Val | Arg | Ser | Asp | Val | Trp | Ser |
|   |   |   |   | 245 |   |   |   |   | 250 |   |   |   |   | 255 |   |
| Leu | Gly | Ile | Thr | Leu | Tyr | Glu | Leu | Ala | Thr | Gly | Arg | Phe | Pro | Tyr | Pro |
|   |   |   | 260 |   |   |   |   | 265 |   |   |   |   | 270 |   |   |
| Lys | Trp | Asn | Ser | Val | Phe | Asp | Gln | Leu | Thr | Gln | Val | Val | Lys | Gly | Asp |
|   |   | 275 |   |   |   |   | 280 |   |   |   |   | 285 |   |   |   |
| Pro | Pro | Gln | Leu | Ser | Asn | Ser | Glu | Glu | Arg | Glu | Phe | Ser | Pro | Ser | Phe |
|   | 290 |   |   |   |   | 295 |   |   |   |   | 300 |   |   |   |   |
| Ile | Asn | Phe | Val | Asn | Leu | Cys | Leu | Thr | Lys | Asp | Glu | Ser | Lys | Arg | Pro |
| 305 |   |   |   |   | 310 |   |   |   |   | 315 |   |   |   |   | 320 |
| Lys | Tyr | Lys | Glu | Leu | Leu | Lys | His | Pro | Phe | Ile | Leu | Met | Tyr | Glu | Glu |
|   |   |   |   | 325 |   |   |   |   | 330 |   |   |   |   | 335 |   |
| Arg | Ala | Val | Glu | Val | Ala | Cys | Tyr | Val | Cys | Lys | Ile | Leu | Asp | Gln | Met |
|   |   |   | 340 |   |   |   |   | 345 |   |   |   |   | 350 |   |   |
| Pro | Ala | Thr | Pro | Ser | Ser | Pro | Met | Tyr | Val | Asp |   |   |   |   |   |
|   |   | 355 |   |   |   |   | 360 |   |   |   |   |   |   |   |   |

( 2 ) INFORMATION FOR SEQ ID NO:7:

( i ) SEQUENCE CHARACTERISTICS:
        ( A ) LENGTH: 3553 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:7:

```
CAACAATGGC GGCTCCGAGC CCGAGCGGTG GCGGCGGCAG CGGCACCCCC GGCCCCGTAG        60
GGTCCCCGGC GCCAGGCCAC CCGGCCGTCA GCAGCATGCA GGGTAAACGC AAAGCACTGA       120
AGTTGAATTT TGCAAATCCA CCTTTCAAAT CTACAGCAAG GTTACTCTG AATCCCAATC        180
CTACAGGAGT TCAAAACCCA CACATAGAGA GACTGAGAAC ACACAGCATT GAGTCATCAG       240
GAAAACTGAA GATCTCCCCT GAACAACACT GGGATTTCAC TGCAGAGGAC TTGAAAGACC       300
TTGGAGAAAT TGGACGAGGA GCTTATGGTT CTGTCAACAA AATGGTCCAC AAACCAAGTG       360
GGCAAATAAT GGCAGTTAAA AGAATTCGGT CAACAGTGGA TGAAAAAGAA CAAAAACAAC       420
TTCTTATGGA TTTGGATGTA GTAATGCGGA GTAGTGATTG CCCATACATT GTTCAGTTTT       480
ATGGTGCACT CTTCAGAGAG GGTGACTGTT GGATCTGTAT GGAACTCATG TCTACCTCGT       540
TTGATAAGTT TTACAAATAT GTATATAGTG TATTAGATGA TGTTATTCCA GAAGAAATTT       600
TAGGCAAAAT CACTTTAGCA ACTGTGAAAG CACTAAACCA CTTAAAAGAA AACTTGAAAA       660
```

-continued

```
TTATTCACAG AGATATCAAA CCTTCCAATA TTCTTCTGGA CAGAAGTGGA AATATTAAGC    720
TCTGTGACTT CGGCATCAGT GGACAGCTTG TGGACTCTAT TGCCAAGACA AGAGATGCTG    780
GCTGTAGGCC ATACATGGCA CCTGAAAGAA TAGACCCAAG CGCATCACGA CAAGGATATG    840
ATGTCCGCTC TGATGTCTGG AGTTTGGGGA TCACATTGTA TGAGTTGGCC ACAGGCCGAT    900
TTCCTTATCC AAAGTGGAAT AGTGTATTTG ATCAACTAAC ACAAGTCGTG AAAGGAGATC    960
CTCCGCAGCT GAGTAATTCT GAGGAAAGGG AATTCTCCCC GAGTTTCATC AACTTTGTCA   1020
ACTTGTGCCT TACGAAGGAT GAATCCAAAA GGCCAAAGTA TAAAGAGCTT CTGAAACATC   1080
CCTTTATTTT GATGTATGAA GAACGTGCCG TTGAGGTCGC ATGCTATGTT TGTAAAATCC   1140
TGGATCAAAT GCCAGCTACT CCCAGCTCTC CATGTATGT CGATTGATAT CGTGCTACAT    1200
CAGACTCTAG AAAAAAGGGC TGAGAGGAAG CAAGACGTAA AGAATTTTCA TCCCGTATCA   1260
CAGTGTTTTT ATTGCTCGCC CAGACACCAT GTGCAATAAG ATTGGTGTTC GTTTCCATCA   1320
TGTCTGTATA CTCCTGTCAC CTAGAACGTG CATCCTTGTA ATACCTGATT GATCACACAG   1380
TGTTAGTGCT GGTCAGAGAG ACCTCATCCT GCTCTTTTGT GATGAACATA TTCATGAAAT   1440
GTGGAAGTCA GTACGATCAA GTTGTTGACT GTGATTAGAT CACATCTTAA ATTCATTTCT   1500
AGACTCAAAA CCTGGAGATG CAGCTACTGG AATGGTGTTT TGTCAGACTT CCAAATCCTG   1560
GAAGGACACA GTGATGAATG TACTATATCT GAACATAGAA ACTCGGCTT GAGTGAGAAG    1620
AGCTTGCACA GCCAACGAGA CACATTGCCT TCTGGAGCTG GGAGACAAAG GAGGAATTTA   1680
CTTTCTTCAC CAAGTGCAAT AGATTACTGA TGTGATATTC TGTTGCTTTA CAGTTACAGT   1740
TGATGTTTGG GGATCGATGT GCTCAGCCAA ATTTCCTGTT TGAAATATCA TGTTAAATTA   1800
GAATGAATTT ATCTTTACCA AAAACCATGT TGCGTTCAAA GAGGTGAACA TTAAAATATA   1860
GAGACAGGAC AGAATGTGTT CTTTTCTCCT CTACCAGTCC TATTTTTCAA TGGGAAGACT   1920
CAGGAGTCTG CCACTTGTCA AAGAAGGTGC TGATCCTAAG AATTTTTCAT TCTCAGAATT   1980
CGGTGTGCTG CCAACTTGAT GTTCCACCTG CCACAAACCA CCAGGACTGA AAGAAGAAAA   2040
CAGTACAGAA GGCAAAGTTT ACAGATGTTT TAATTCTAG TATTTATCT GGAACAACTT     2100
GTAGCAGCTA TATATTTCCC CTTGGTCCCA AGCCTGATAC TTTAGCCATC ATAACTCACT   2160
AACAGGGAGA AGTAGCTAGT AGCAATGTGC CTTGATTGAT TAGATAAAGA TTTCTAGTAG   2220
GCAGCAAAAG ACCAAATCTC AGTTGTTTGC TTCTTGCCAT CACTGGTCCA GGTCTTCAGT   2280
TTCCGAATCT CTTTCCCTTC CCCTGTGGTC TATTGTCGCT ATGTGACTTG CGCTTAATCC   2340
AATATTTTGC CTTTTTTCTA TATCAAAAAA CCTTTACAGT TAGCAGGGAT GTTCCTTACC   2400
GAGGATTTTT AACCCCCAAT CTCTCATAAT CGCTAGTGTT TAAAAGGCTA AGAATAGTGG   2460
GGCCCAACCG ATGTGGTAGG TGATAAAGAG GCATCTTTTC TAGAGACACA TTGGACCAGA   2520
TGAGGATCCG AAACGGCAGC CTTTACGTTC ATCACCTGCT AGAACCTCTC GTAGTCCATC   2580
ACCATTTCTT GGCATTGGAA TTCTACTGGA AAAAAATACA AAAGCAAAA CAAAACCCTC    2640
AGCACTGTTA CAAGAGGCCA TTTAAGTATC TTGTGCTTCT TCACTTACCC ATTAGCCAGG   2700
TTCTCATTAG GTTTTGCTTG GGCCTCCCTG GCACTGAACC TTAGGCTTTG TATGACAGTG   2760
AAGCAGCACT GTGAGTGGTT CAAGCACACT GGAATATAAA ACAGTCATGG CCTGAGATGC   2820
AGGTGATGCC ATTACAGAAC CAAATCGTGG CACGTATTGC TGTGTCTCCT CTCAGAGTGA   2880
CAGTCATAAA TACTGTCAAA CAATAAAGGG AGAATGGTGC TGTTTAAAGT CACATCCCTG   2940
TAAATTGCAG AATTCAAAAG TGATTATCTC TTTGATCTAC TTGCCTCATT TCCCTATCTT   3000
CTCCCCCACG GTATCCTAAA CTTTAGACTT CCCACTGTTC TGAAAGGAGA CATTGCTCTA   3060
```

| | | | | | |
|---|---|---|---|---|---|
|TGTCTGCCTT|CGACCACAGC|AAGCCATCAT|CCTCCATTGC|TCCCGGGGAC|TCAAGAGGAA|3120
|TCTGTTTCTC|TGCTGTCAAC|TTCCCATCTG|GCTCAGCATA|GGGTCACTTT|GCCATTATGC|3180
|AAATGGAGAT|AAAAGCAATT|CTGGCTGTCC|AGGAGCTAAT|CTGACCGTTC|TATTGTGTGG|3240
|ATGACCACAT|AAGAAGGCAA|TTTTAGTGTA|TTAATCATAG|ATTATTATAA|ACTATAAACT|3300
|TAAGGGCAAG|GAGTTTATTA|CAATGTATCT|TTATTAAAAC|AAAAGGGTGT|ATAGTGTTCA|3360
|CAAACTGTGA|AAATAGTGTA|AGAACTGTAC|ATTGTGAGCT|CTGGTTATTT|TTCTCTTGTA|3420
|CCATAGAAAA|ATGTATAAAA|ATTATCAAAA|AGCTAATGTG|CAGGGATATT|GCCTTATTTG|3480
|TCTGTAAAAA|ATGGAGCTCA|GTAACATAAC|TGCTTCTTGG|AGCTTTGGAA|TATTTTATCC|3540
|TGTATTCTTG|TTT| | | | |3553

( 2 ) INFORMATION FOR SEQ ID NO:8:

( i ) SEQUENCE CHARACTERISTICS:
        ( A ) LENGTH: 393 amino acids
        ( B ) TYPE: amino acid
        ( C ) STRANDEDNESS: Not Relevant
        ( D ) TOPOLOGY: linear ( x i ) SEQUENCE DESCRIPTION: SEQ ID NO:8:

```
Met Ala Ala Pro Ser Pro Ser Gly Gly Gly Gly Ser Gly Thr Pro Gly
  1               5                  10                  15

Pro Val Gly Ser Pro Ala Pro Gly His Pro Ala Val Ser Ser Met Gln
             20                  25                  30

Gly Lys Arg Lys Ala Leu Lys Leu Asn Phe Ala Asn Pro Pro Phe Lys
         35                  40                  45

Ser Thr Ala Arg Phe Thr Leu Asn Pro Asn Pro Thr Gly Val Gln Asn
     50                  55                  60

Pro His Ile Glu Arg Leu Arg Thr His Ser Ile Glu Ser Ser Gly Lys
 65                  70                  75                  80

Leu Lys Ile Ser Pro Glu Gln His Trp Asp Phe Thr Ala Glu Asp Leu
                 85                  90                  95

Lys Asp Leu Gly Glu Ile Gly Arg Gly Ala Tyr Gly Ser Val Asn Lys
             100                 105                 110

Met Val His Lys Pro Ser Gly Gln Ile Met Ala Val Lys Arg Ile Arg
         115                 120                 125

Ser Thr Val Asp Glu Lys Glu Gln Lys Gln Leu Leu Met Asp Leu Asp
     130                 135                 140

Val Val Met Arg Ser Ser Asp Cys Pro Tyr Ile Val Gln Phe Tyr Gly
145                 150                 155                 160

Ala Leu Phe Arg Glu Gly Asp Cys Trp Ile Cys Met Glu Leu Met Ser
                 165                 170                 175

Thr Ser Phe Asp Lys Phe Tyr Lys Tyr Val Tyr Ser Val Leu Asp Asp
             180                 185                 190

Val Ile Pro Glu Glu Ile Leu Gly Lys Ile Thr Leu Ala Thr Val Lys
         195                 200                 205

Ala Leu Met His Leu Lys Glu Asn Leu Lys Ile Ile His Arg Asp Ile
     210                 215                 220

Lys Pro Ser Asn Ile Leu Leu Asp Arg Ser Gly Met Ile Lys Leu Cys
225                 230                 235                 240

Asp Phe Gly Ile Ser Gly Gln Leu Val Asp Ser Ile Ala Lys Thr Arg
                 245                 250                 255

Asp Ala Gly Cys Arg Pro Tyr Met Ala Pro Glu Arg Ile Asp Phe Ser
             260                 265                 270
```

|     |     |     |     |     |     |     |     |     |     |     |     |     |     |     |
| --- | --- | --- | --- | --- | --- | --- | --- | --- | --- | --- | --- | --- | --- | --- |
| Ala | Ser | Arg<br>275 | Gln | Gly | Tyr | Asp<br>280 | Val | Arg | Ser | Asp<br>285 | Val | Trp | Ser | Leu | Gly |
| Ile | Thr<br>290 | Leu | Tyr | Glu | Leu<br>295 | Ala | Thr | Gly | Arg | Phe<br>300 | Pro | Tyr | Pro | Lys | Trp |
| Asn<br>305 | Ser | Val | Phe | Asp<br>310 | Gln | Leu | Thr | Gln | Val<br>315 | Val | Lys | Gly | Asp | Pro<br>320 | Pro |
| Gln | Leu | Ser | Asn | Ser<br>325 | Glu | Glu | Arg | Glu | Phe<br>330 | Ser | Pro | Ser | Phe | Ile<br>335 | Asn |
| Phe | Val | Asn | Leu<br>340 | Cys | Leu | Thr | Lys | Asp<br>345 | Glu | Ser | Lys | Arg | Pro<br>350 | Lys | Tyr |
| Lys | Glu | Leu<br>355 | Leu | Lys | His | Pro | Phe<br>360 | Ile | Leu | Met | Tyr | Glu<br>365 | Glu | Arg | Ala |
| Val | Glu<br>370 | Val | Ala | Cys | Tyr | Val<br>375 | Cys | Lys | Ile | Leu | Asp<br>380 | Gln | Met | Pro | Ala |
| Thr<br>385 | Pro | Ser | Ser | Pro | Met<br>390 | Tyr | Val | Asp |     |     |     |     |     |     |     |

( 2 ) INFORMATION FOR SEQ ID NO:9:

( i ) SEQUENCE CHARACTERISTICS:
( A ) LENGTH: 3576 base pairs
( B ) TYPE: nucleic acid
( C ) STRANDEDNESS: single
( D ) TOPOLOGY: linear ( x i ) SEQUENCE DESCRIPTION: SEQ ID NO:9:

| | | | | | |
| --- | --- | --- | --- | --- | --- |
| CTCCCAACAA | TGGCGGCTCC | GAGCCCGAGC | GGCGGCGGCG | GCTCCGGGGG | CGGCAGCGGC | 60 |
| AGCGGCACCC | CCGGCCCCGT | AGGGTCCCCG | GCGCCAGGCC | ACCCGGCCGT | CAGCAGCATG | 120 |
| CAGGGTAAAC | GCAAAGCACT | GAAGTTGAAT | TTTGCAAATC | CACCTTTCAA | ATCTACAGCA | 180 |
| AGGTTTACTC | TGAATCCCAA | TCCTACAGGA | GTTCAAAACC | CACACATAGA | GAGACTGAGA | 240 |
| ACACACAGCA | TTGAGTCATC | AGGAAAACTG | AAGATCTCCC | CTGAACAACA | CTGGGATTTC | 300 |
| ACTGCAGAGG | ACTTGAAAGA | CCTTGGAGAA | ATTGGACGAG | GAGCTTATGG | TTCTGTCAAC | 360 |
| AAAATGGTCC | ACAAACCAAG | TGGGCAAATA | ATGGCAGTTA | AAGAATTCG | GTCAACAGTG | 420 |
| GATGAAAAAG | AACAAAAACA | ACTTCTTATG | GATTTGGATG | TAGTAATGCG | GAGTAGTGAT | 480 |
| TGCCCATACA | TTGTTCAGTT | TTATGGTGCA | CTCTTCAGAG | AGGGTGACTG | TTGGATCTGT | 540 |
| ATGGAACTCA | TGTCTACCTC | GTTTGATAAG | TTTTACAAAT | ATGTATATAG | TGTATTAGAT | 600 |
| GATGTTATTC | CAGAAGAAAT | TTTAGGCAAA | ATCACTTTAG | CAACTGTGAA | AGCACTAAAC | 660 |
| CACTTAAAAG | AAAACTTGAA | AATTATTCAC | AGAGATATCA | AACCTTCCAA | TATTCTTCTG | 720 |
| GACAGAAGTG | GAAATATTAA | GCTCTGTGAC | TTCGGCATCA | GTGGACAGCT | TGTGGACTCT | 780 |
| ATTGCCAAGA | CAAGAGATGC | TGGCTGTAGG | CCATACATGG | CACCTGAAAG | AATAGACCCA | 840 |
| AGCGCATCAC | GACAAGGATA | TGATGTCCGC | TCTGATGTCT | GGAGTTTGGG | GATCACATTG | 900 |
| TATGAGTTGG | CCACAGGCCG | ATTTCCTTAT | CCAAAGTGGA | ATAGTGTATT | TGATCAACTA | 960 |
| ACACAAGTCG | TGAAAGGAGA | TCCTCCGCAG | CTGAGTAATT | CTGAGGAAAG | GGAATTCTCC | 1020 |
| CCGAGTTTCA | TCAACTTTGT | CAACTTGTGC | CTTACGAAGG | ATGAATCCAA | AAGGCCAAAG | 1080 |
| TATAAAGAGC | TTCTGAAACA | TCCCTTTATT | TTGATGTATG | AAGAACGTGC | CGTTGAGGTC | 1140 |
| GCATGCTATG | TTTGTAAAAT | CCTGGATCAA | ATGCCAGCTA | CTCCCAGCTC | TCCCATGTAT | 1200 |
| GTCGATTGAT | ATCGCTGCTA | CATCAGACTC | TAGAAAAAAG | GGCTGAGAGG | AAGCAAGACG | 1260 |
| TAAAGAATTT | TCATCCCGTA | TCACAGTGTT | TTTATTGCTC | GCCCAGACAC | CATGTGCAAT | 1320 |
| AAGATTGGTG | TTCGTTTCCA | TCATGTCTGT | ATACTCCTGT | CACCTAGAAC | GTGCATCCTT | 1380 |

-continued

```
GTAATACCTG ATTGATCACA CAGTGTTAGT GCTGGTCAGA GAGACCTCAT CCTGCTCTTT      1440
TGTGATGAAC ATATTCATGA AATGTGGAAG TCAGTACGAT CAAGTTGTTG ACTGTGATTA      1500
GATCACATCT TAAATTCATT TCTAGACTCA AAACCTGGAG ATGCAGCTAC TGGAATGGTG      1560
TTTTGTCAGA CTTCCAAATC CTGGAAGGAC ACAGTGATGA ATGTACTATA TCTGAACATA      1620
GAAACTCGGG CTTGAGTGAG AAGAGCTTGC ACAGCCAACG AGACACATTG CCTTCTGGAG      1680
CTGGGAGACA AAGGAGGAAT TTACTTTCTT CACCAAGTGC AATAGATTAC TGATGTGATA      1740
TTCTGTTGCT TTACAGTTAC AGTTGATGTT TGGGGATCGA TGTGCTCAGC CAAATTTCCT      1800
GTTTGAAATA TCATGTTAAA TTAGAATGAA TTTATCTTTA CCAAAAACCA TGTTGCGTTC      1860
AAAGAGGTGA ACATTAAAAT ATAGAGACAG GACAGAATGT GTTCTTTTCT CCTCTACCAG      1920
TCCTATTTTT CAATGGGAAG ACTCAGGAGT CTGCCACTTG TCAAAGAAGG TGCTGATCCT      1980
AAGAATTTTT CATTCTCAGA ATTCGGTGTG CTGCCAACTT GATGTTCCAC CTGCCACAAA      2040
CCACCAGGAC TGAAAGAAGA AAACAGTACA GAAGGCAAAG TTTACAGATG TTTTAATTC       2100
TAGTATTTTA TCTGGAACAA CTTGTAGCAG CTATATATTT CCCCTTGGTC CCAAGCCTGA      2160
TACTTTAGCC ATCATAACTC ACTAACAGGG AGAAGTAGCT AGTAGCAATG TGCCTTGATT      2220
GATTAGATAA AGATTTCTAG TAGGCAGCAA AAGACCAAAT CTCAGTTGTT TGCTTCTTGC      2280
CATCACTGGT CCAGGTCTTC AGTTTCCGAA TCTCTTTCCC TTCCCTGTG GTCTATTGTC       2340
GCTATGTGAC TTGCGCTTAA TCCAATATTT TGCCTTTTTT CTATATCAAA AAACCTTTAC      2400
AGTTAGCAGG GATGTTCCTT ACGAGGATT TTTAACCCCC AATCTCTCAT AATCGCTAGT       2460
GTTTAAAAGG CTAAGAATAG TGGGGCCCAA CCGATGTGGT AGGTGATAAA GAGGCATCTT      2520
TTCTAGAGAC ACATTGGACC AGATGAGGAT CCGAAACGGC AGCCTTTACG TTCATCACCT      2580
GCTAGAACCT CTCGTAGTCC ATCACCATTT CTTGGCATTG GAATTCTACT GGAAAAAAAT      2640
ACAAAAAGCA AAACAAAACC CTCAGCACTG TTACAAGAGG CCATTTAAGT ATCTTGTGCT      2700
TCTTCACTTA CCCATTAGCC AGGTTCTCAT TAGGTTTTGC TTGGGCCTCC CTGGCACTGA      2760
ACCTTAGGCT TTGTATGACA GTGAAGCAGC ACTGTGAGTG GTTCAAGCAC ACTGGAATAT      2820
AAAACAGTCA TGGCCTGAGA TGCAGGTGAT GCCATTACAG AACCAAATCG TGGCACGTAT      2880
TGCTGTGTCT CCTCTCAGAG TGACAGTCAT AAATACTGTC AAACAATAAA GGGAGAATGG      2940
TGCTGTTTAA AGTCACATCC CTGTAAATTG CAGAATTCAA AAGTGATTAT CTCTTTGATC      3000
TACTTGCCTC ATTTCCCTAT CTTCTCCCCC ACGGTATCCT AAACTTTAGA CTTCCCACTG      3060
TTCTGAAAGG AGACATTGCT CTATGTCTGC CTTCGACCAC AGCAAGCCAT CATCCTCCAT      3120
TGCTCCCGGG GACTCAAGAG GAATCTGTTT CTCTGCTGTC AACTTCCCAT CTGGCTCAGC      3180
ATAGGGTCAC TTTGCCATTA TGCAAATGGA GATAAAAGCA ATTCTGGCTG TCCAGGAGCT      3240
AATCTGACCG TTCTATTGTG TGGATGACCA CATAAGAAGG CAATTTTAGT GTATTAATCA      3300
TAGATTATTA TAAACTATAA ACTTAAGGGC AAGGAGTTTA TTACAATGTA TCTTTATTAA      3360
AACAAAAGGG TGTATAGTGT TCACAAACTG TGAAAATAGT GTAAGAACTG TACATTGTGA      3420
GCTCTGGTTA TTTTTCTCTT GTACCATAGA AAAATGTATA AAAATTATCA AAAAGCTAAT      3480
GTGCAGGGAT ATTGCCTTAT TTGTCTGTAA AAAATGGAGC TCAGTAACAT AACTGCTTCT      3540
TGGAGCTTTG GAATATTTTA TCCTGTATTC TTGTTT                                3576
```

( 2 ) INFORMATION FOR SEQ ID NO:10:

( i ) SEQUENCE CHARACTERISTICS:
( A ) LENGTH: 399 amino acids (B) TYPE: amino acid
(C) STRANDEDNESS: Not Relevant
(D) TOPOLOGY: linear (xi) SEQUENCE DESCRIPTION: SEQ ID NO:10:

| | | | | | | | | | | | | | | |
|---|---|---|---|---|---|---|---|---|---|---|---|---|---|---|
| Met 1 | Ala | Ala | Pro | Ser 5 | Pro | Ser | Gly | Gly | Gly 10 | Ser | Gly | Gly | Gly 15 | Ser |
| Gly | Ser | Gly | Thr 20 | Pro | Gly | Pro | Val 25 | Gly | Ser | Pro | Ala | Pro 30 | Gly | His | Pro |
| Ala | Val | Ser 35 | Ser | Met | Gln | Gly | Lys 40 | Arg | Lys | Ala | Leu | Lys 45 | Leu | Asn | Phe |
| Ala | Asn 50 | Pro | Pro | Phe | Lys | Ser 55 | Thr | Ala | Arg | Phe | Thr 60 | Leu | Asn | Pro | Asn |
| Pro 65 | Thr | Gly | Val | Gln | Asn 70 | Pro | His | Ile | Glu | Arg 75 | Leu | Arg | Thr | His | Ser 80 |
| Ile | Glu | Ser | Ser | Gly 85 | Lys | Leu | Lys | Ile | Ser 90 | Pro | Glu | Gln | His | Trp | Asp 95 |
| Phe | Thr | Ala | Glu 100 | Asp | Leu | Lys | Asp | Leu 105 | Gly | Glu | Ile | Gly | Arg 110 | Gly | Ala |
| Tyr | Gly | Ser 115 | Val | Asn | Lys | Met | Val 120 | His | Lys | Pro | Ser | Gly 125 | Gln | Ile | Met |
| Ala | Val 130 | Lys | Arg | Ile | Arg | Ser 135 | Thr | Val | Asp | Glu | Lys 140 | Glu | Gln | Lys | Gln |
| Leu 145 | Leu | Met | Asp | Leu | Asp 150 | Val | Val | Met | Arg | Ser 155 | Ser | Asp | Cys | Pro | Tyr 160 |
| Ile | Val | Gln | Phe | Tyr 165 | Gly | Ala | Leu | Phe | Arg 170 | Glu | Gly | Asp | Cys | Trp 175 | Ile |
| Cys | Met | Glu | Leu 180 | Met | Ser | Thr | Ser | Phe 185 | Asp | Lys | Phe | Tyr | Lys 190 | Tyr | Val |
| Tyr | Ser | Val 195 | Leu | Asp | Asp | Val | Ile 200 | Pro | Glu | Glu | Ile | Leu 205 | Gly | Lys | Ile |
| Thr | Leu 210 | Ala | Thr | Val | Lys | Ala 215 | Leu | Asn | His | Leu | Lys 220 | Glu | Asn | Leu | Lys |
| Ile 225 | Ile | His | Arg | Asp | Ile 230 | Lys | Pro | Ser | Asn | Ile 235 | Leu | Leu | Asp | Arg | Ser 240 |
| Gly | Asn | Ile | Lys | Leu 245 | Cys | Asp | Phe | Gly | Ile 250 | Ser | Gly | Gln | Leu | Val 255 | Asp |
| Ser | Ile | Ala | Lys | Thr 260 | Arg | Asp | Ala | Gly | Cys 265 | Arg | Pro | Tyr | Met 270 | Ala | Pro |
| Glu | Arg | Ile 275 | Asp | Pro | Ser | Ala | Ser 280 | Arg | Gln | Gly | Tyr | Asp 285 | Val | Arg | Ser |
| Asp | Val 290 | Trp | Ser | Leu | Gly | Ile 295 | Thr | Leu | Tyr | Glu | Leu 300 | Ala | Thr | Gly | Arg |
| Phe | Pro 305 | Tyr | Pro | Lys | Trp 310 | Asn | Ser | Val | Phe | Asp 315 | Gln | Leu | Thr | Gln | Val 320 |
| Val | Lys | Gly | Asp | Pro 325 | Pro | Gln | Leu | Ser | Asn 330 | Ser | Glu | Glu | Arg | Glu 335 | Phe |
| Ser | Pro | Ser | Phe 340 | Ile | Asn | Phe | Val | Asn 345 | Leu | Cys | Leu | Thr | Lys 350 | Asp | Glu |
| Ser | Lys | Arg 355 | Pro | Lys | Tyr | Lys | Glu 360 | Leu | Leu | Lys | His | Pro 365 | Phe | Ile | Leu |
| Met | Tyr | Glu 370 | Glu | Arg | Ala | Val | Glu 375 | Val | Ala | Cys | Tyr 380 | Val | Cys | Lys | Ile |
| Leu 385 | Asp | Gln | Met | Pro | Ala 390 | Thr | Pro | Ser | Ser | Pro 395 | Met | Tyr | Val | Asp |

( 2 ) INFORMATION FOR SEQ ID NO:11:

( i ) SEQUENCE CHARACTERISTICS:
        ( A ) LENGTH: 393 amino acids
        ( B ) TYPE: amino acid
        ( C ) STRANDEDNESS: Not Relevant
        ( D ) TOPOLOGY: linear ( x i ) SEQUENCE DESCRIPTION: SEQ ID NO:11:

```
Met Pro Lys Lys Lys Pro Thr Pro Ile Gln Leu Asn Pro Ala Pro Asp
 1               5                  10                  15
Gly Ser Ala Val Asn Gly Thr Ser Ser Ala Glu Thr Asn Leu Glu Ala
             20                  25                  30
Leu Gln Lys Lys Leu Glu Glu Leu Glu Leu Asp Glu Gln Gln Arg Lys
         35                  40                  45
Arg Leu Glu Ala Phe Leu Thr Gln Lys Gln Lys Val Gly Glu Leu Lys
     50                  55                  60
Asp Asp Asp Phe Glu Lys Ile Ser Glu Leu Gly Ala Gly Asn Gly Gly
 65                  70                  75                  80
Val Val Phe Lys Val Ser His Lys Pro Ser Gly Leu Val Met Ala Arg
                 85                  90                  95
Lys Leu Ile His Leu Glu Ile Lys Pro Ala Ile Arg Asn Gln Ile Ile
             100                 105                 110
Arg Glu Leu Gln Val Leu His Glu Cys Asn Ser Pro Tyr Ile Val Gly
         115                 120                 125
Phe Tyr Gly Ala Phe Tyr Ser Asp Gly Glu Ile Ser Ile Cys Met Glu
     130                 135                 140
His Met Asp Gly Gly Ser Leu Asp Gln Val Leu Lys Lys Ala Gly Arg
145                 150                 155                 160
Ile Pro Glu Gln Ile Leu Gly Lys Val Ser Ile Ala Val Ile Lys Gly
                 165                 170                 175
Leu Thr Tyr Leu Arg Glu Lys His Lys Ile Met His Arg Asp Val Lys
             180                 185                 190
Pro Ser Asn Ile Leu Val Asn Ser Arg Gly Glu Ile Lys Leu Cys Asp
         195                 200                 205
Phe Gly Val Ser Gly Gln Leu Ile Asp Ser Met Ala Asn Ser Phe Val
     210                 215                 220
Gly Thr Arg Ser Tyr Met Ser Pro Glu Arg Leu Gln Gly Thr His Tyr
225                 230                 235                 240
Ser Val Gln Ser Asp Ile Trp Ser Met Gly Leu Ser Leu Val Glu Met
                 245                 250                 255
Ala Val Gly Arg Tyr Pro Ile Pro Pro Asp Ala Lys Glu Leu Glu
             260                 265                 270
Leu Met Phe Gly Cys Gln Val Glu Gly Asp Ala Ala Glu Thr Pro Pro
         275                 280                 285
Arg Pro Arg Thr Pro Gly Arg Pro Leu Ser Ser Tyr Gly Met Asp Ser
     290                 295                 300
Arg Pro Pro Met Ala Ile Phe Glu Leu Leu Asp Tyr Ile Val Asn Glu
305                 310                 315                 320
Pro Pro Pro Lys Leu Pro Ser Gly Val Phe Ser Leu Glu Phe Gln Asp
                 325                 330                 335
Phe Val Asn Lys Cys Leu Ile Lys Asn Pro Ala Glu Arg Ala Asp Leu
             340                 345                 350
Lys Gln Leu Met Val His Ala Phe Ile Lys Arg Ser Asp Ala Glu Glu
         355                 360                 365
```

```
Val  Asp  Phe  Ala  Gly  Trp  Leu  Cys  Ser  Thr  Ile  Gly  Leu  Asn  Gln  Pro
     370                 375                 380

Ser  Thr  Pro  Thr  His  Ala  Ala  Gly  Val
385                      390
```

( 2 ) INFORMATION FOR SEQ ID NO:12:

( i ) SEQUENCE CHARACTERISTICS:
         ( A ) LENGTH: 400 amino acids
         ( B ) TYPE: amino acid
         ( C ) STRANDEDNESS: Not Relevant
         ( D ) TOPOLOGY: linear ( x i ) SEQUENCE DESCRIPTION: SEQ ID NO:12:

```
Met  Leu  Ala  Arg  Arg  Lys  Pro  Val  Leu  Pro  Ala  Leu  Thr  Ile  Asn  Pro
1                    5                    10                       15

Thr  Ile  Ala  Glu  Gly  Pro  Ser  Pro  Thr  Ser  Glu  Gly  Ala  Ser  Glu  Ala
               20                   25                   30

Asn  Leu  Val  Asp  Leu  Gln  Lys  Lys  Leu  Glu  Glu  Leu  Glu  Leu  Asp  Glu
          35                   40                   45

Gln  Gln  Lys  Lys  Arg  Leu  Glu  Ala  Phe  Leu  Thr  Gln  Lys  Ala  Lys  Val
50                        55                        60

Ser  Glu  Leu  Lys  Asp  Asp  Phe  Glu  Arg  Ile  Ser  Glu  Leu  Gly  Ala
65                   70                        75                        80

Gly  Asn  Gly  Gly  Val  Val  Thr  Lys  Val  Gln  His  Arg  Pro  Ser  Gly  Leu
                    85                        90                        95

Ile  Met  Ala  Arg  Lys  Leu  Ile  His  Leu  Glu  Ile  Lys  Pro  Ala  Ile  Arg
               100                      105                      110

Asn  Gln  Ile  Ile  Arg  Glu  Leu  Gln  Val  Leu  His  Glu  Cys  Asn  Ser  Pro
          115                      120                      125

Tyr  Ile  Val  Gly  Phe  Tyr  Gly  Ala  Phe  Tyr  Ser  Asp  Gly  Glu  Ile  Ser
     130                      135                      140

Ile  Cys  Met  Glu  His  Met  Asp  Gly  Gly  Ser  Leu  Asp  Gln  Val  Leu  Lys
145                      150                      155                      160

Glu  Ala  Lys  Arg  Ile  Pro  Glu  Glu  Ile  Leu  Gly  Lys  Val  Ser  Ile  Ala
                    165                      170                      175

Val  Leu  Arg  Gly  Leu  Ala  Tyr  Leu  Arg  Glu  Lys  His  Gln  Ile  Met  His
               180                      185                      190

Arg  Asp  Val  Lys  Pro  Ser  Asn  Ile  Leu  Val  Asn  Ser  Arg  Gly  Glu  Ile
          195                      200                      205

Lys  Leu  Cys  Asp  Phe  Gly  Val  Ser  Gly  Gln  Leu  Ile  Asp  Ser  Met  Ala
     210                      215                      220

Asn  Ser  Phe  Val  Gly  Thr  Arg  Ser  Tyr  Met  Ala  Pro  Glu  Arg  Leu  Gln
225                      230                      235                      240

Gly  Thr  His  Tyr  Ser  Val  Gln  Ser  Asp  Ile  Trp  Ser  Met  Gly  Leu  Ser
               245                      250                      255

Leu  Val  Glu  Leu  Ala  Val  Gly  Arg  Tyr  Pro  Ile  Pro  Pro  Asp  Ala
          260                      265                      270

Lys  Glu  Leu  Glu  Ala  Ile  Phe  Gly  Arg  Pro  Val  Val  Asp  Gly  Glu  Glu
          275                      280                      285

Gly  Glu  Pro  His  Ser  Ile  Ser  Pro  Arg  Pro  Arg  Pro  Pro  Gly  Arg  Pro
     290                      295                      300

Val  Ser  Gly  His  Gly  Met  Asp  Ser  Arg  Pro  Ala  Met  Ala  Ile  Phe  Glu
305                      310                      315                      320

Leu  Leu  Asp  Tyr  Ile  Val  Asn  Glu  Pro  Pro  Pro  Lys  Leu  Pro  Asn  Gly
               325                      330                      335
```

```
Val  Phe  Thr  Pro  Asp  Phe  Gln  Glu  Phe  Val  Asn  Lys  Cys  Leu  Ile  Lys
               340                 345                      350

Asn  Pro  Ala  Glu  Arg  Ala  Asp  Leu  Lys  Met  Leu  Thr  Asn  His  Thr  Phe
               355                 360                      365

Ile  Lys  Arg  Ser  Glu  Val  Glu  Glu  Val  Asp  Phe  Ala  Gly  Trp  Leu  Cys
     370                 375                      380

Lys  Thr  Leu  Arg  Leu  Asn  Gln  Pro  Gly  Thr  Pro  Thr  Arg  Thr  Ala  Val
385                      390                      395                      400
```

(2) INFORMATION FOR SEQ ID NO:13:

(i) SEQUENCE CHARACTERISTICS:
        (A) LENGTH: 668 amino acids
        (B) TYPE: amino acid
        (C) STRANDEDNESS: Not Relevant
        (D) TOPOLOGY: linear (xi) SEQUENCE DESCRIPTION: SEQ ID NO:13:

```
Met  Glu  Asp  Lys  Phe  Ala  Asn  Leu  Ser  Leu  His  Glu  Lys  Thr  Gly  Lys
1                   5                   10                       15

Ser  Ser  Ile  Gln  Leu  Asn  Glu  Gln  Thr  Gly  Ser  Asp  Asn  Gly  Ser  Ala
          20                       25                       30

Val  Lys  Arg  Thr  Ser  Ser  Thr  Ser  Ser  His  Tyr  Asn  Asn  Ile  Asn  Ala
               35                  40                       45

Asp  Leu  His  Ala  Arg  Val  Lys  Ala  Phe  Gln  Glu  Gln  Arg  Ala  Leu  Lys
     50                       55                  60

Arg  Ser  Ala  Ser  Val  Gly  Ser  Asn  Gln  Ser  Glu  Gln  Asp  Lys  Gly  Ser
65                       70                  75                            80

Ser  Gln  Ser  Pro  Lys  His  Ile  Gln  Gln  Ile  Val  Asn  Lys  Pro  Leu  Pro
               85                       90                       95

Pro  Leu  Pro  Val  Ala  Gly  Ser  Ser  Lys  Val  Ser  Gln  Arg  Met  Ser  Ser
               100                      105                      110

Gln  Val  Val  Gln  Ala  Ser  Ser  Lys  Ser  Thr  Leu  Lys  Asn  Val  Leu  Asp
               115                      120                      125

Asn  Gln  Glu  Thr  Gln  Asn  Ile  Thr  Asp  Val  Asn  Ile  Asn  Ile  Asp  Thr
     130                      135                      140

Thr  Lys  Ile  Thr  Ala  Thr  Thr  Ile  Gly  Val  Asn  Ile  Gly  Leu  Pro  Ala
145                      150                      155                      160

Thr  Asp  Ile  Thr  Pro  Ser  Val  Ser  Asn  Thr  Ala  Ser  Ala  Thr  His  Lys
                    165                      170                      175

Ala  Gln  Leu  Leu  Asn  Pro  Asn  Arg  Arg  Ala  Pro  Arg  Arg  Pro  Leu  Ser
               180                      185                      190

Thr  Gln  His  Pro  Thr  Arg  Pro  Asn  Val  Ala  Pro  His  Lys  Ala  Pro  Ala
          195                      200                      205

Ile  Ile  Asn  Thr  Pro  Lys  Gln  Ser  Leu  Ser  Ala  Arg  Arg  Gly  Leu  Lys
     210                      215                      220

Leu  Pro  Pro  Gly  Gly  Met  Ser  Leu  Lys  Met  Pro  Thr  Lys  Thr  Ala  Gln
225                      230                      235                      240

Gln  Pro  Gln  Gln  Phe  Ala  Pro  Ser  Pro  Ser  Asn  Lys  Lys  His  Ile  Glu
                    245                      250                      255

Thr  Leu  Ser  Asn  Ser  Lys  Val  Val  Glu  Gly  Lys  Arg  Ser  Asn  Pro  Gly
               260                      265                      270

Ser  Leu  Ile  Asn  Gly  Val  Gln  Ser  Thr  Ser  Thr  Ser  Ser  Ser  Thr  Glu
          275                      280                      285

Gly  Pro  His  Asp  Thr  Val  Gly  Thr  Thr  Pro  Arg  Thr  Gly  Asn  Ser  Asn
     290                      295                      300
```

| | | | | | | | | | | | | | | |
|---|---|---|---|---|---|---|---|---|---|---|---|---|---|---|
| Asn 305 | Ser | Ser | Asn | Ser 310 | Gly | Ser | Gly | Gly 315 | Gly | Leu | Phe | Ala | Asn 320 | |
| Phe | Ser | Lys | Tyr | Val 325 | Asp | Ile | Lys | Ser 330 | Gly | Ser | Leu | Asn | Phe | Ala 335 | Gly |
| Lys | Leu | Ser | Leu 340 | Ser | Ser | Lys | Gly | Ile 345 | Asp | Phe | Ser | Asn | Gly 350 | Ser | Ser |
| Ser | Arg | Ile 355 | Thr | Leu | Asp | Glu | Leu 360 | Glu | Phe | Leu | Asp | Glu 365 | Leu | Gly | His |
| Gly | Asn 370 | Tyr | Gly | Asn | Val | Ser 375 | Lys | Val | Leu | His | Lys 380 | Pro | Thr | Asn | Val |
| Ile 385 | Met | Ala | Thr | Lys | Glu 390 | Val | Arg | Leu | Glu | Leu 395 | Asp | Glu | Ala | Lys | Phe 400 |
| Arg | Gln | Ile | Leu | Met 405 | Glu | Leu | Glu | Val | Leu 410 | His | Lys | Cys | Asn | Ser 415 | Pro |
| Tyr | Ile | Val | Asp 420 | Phe | Tyr | Gly | Ala | Phe 425 | Phe | Ile | Glu | Gly | Ala 430 | Val | Tyr |
| Met | Cys | Met 435 | Glu | Tyr | Met | Asp | Gly 440 | Gly | Ser | Leu | Asp | Lys 445 | Ile | Tyr | Asp |
| Glu | Ser 450 | Ser | Glu | Ile | Gly | Gly 455 | Ile | Asp | Glu | Pro | Gln 460 | Leu | Ala | Phe | Ile |
| Ala 465 | Asn | Ala | Val | Ile | His 470 | Gly | Leu | Lys | Glu | Leu 475 | Lys | Glu | Gln | His | Asn 480 |
| Ile | Ile | His | Arg | Asp 485 | Val | Lys | Pro | Thr | Asn 490 | Ile | Leu | Cys | Ser | Ala 495 | Asn |
| Gln | Gly | Thr | Val 500 | Lys | Leu | Cys | Asp | Phe 505 | Gly | Val | Ser | Gly | Asn 510 | Leu | Val |
| Ala | Ser | Leu 515 | Ala | Lys | Thr | Asn | Ile 520 | Gly | Cys | Gln | Ser | Tyr 525 | Met | Ala | Pro |
| Glu | Arg 530 | Ile | Lys | Ser | Leu | Asn 535 | Pro | Asp | Arg | Ala | Thr 540 | Tyr | Thr | Val | Gln |
| Ser 545 | Asp | Ile | Trp | Ser | Leu 550 | Gly | Leu | Ser | Ile | Leu 555 | Glu | Met | Ala | Leu | Gly 560 |
| Arg | Tyr | Pro | Tyr | Pro 565 | Pro | Glu | Thr | Tyr | Asp 570 | Asn | Ile | Phe | Ser | Gln 575 | Leu |
| Ser | Ala | Ile | Val 580 | Asp | Gly | Pro | Pro | Arg 585 | Leu | Pro | Ser | Asp 590 | Lys | Phe | |
| Ser | Ser | Asp 595 | Ala | Gln | Asp | Phe | Val 600 | Ser | Leu | Cys | Leu | Gln 605 | Lys | Ile | Pro |
| Glu | Arg 610 | Arg | Pro | Thr | Tyr | Ala 615 | Ala | Leu | Thr | Glu | His 620 | Pro | Trp | Leu | Val |
| Lys 625 | Tyr | Arg | Asn | Gln | Asp 630 | Val | His | Met | Ser | Glu 635 | Tyr | Ile | Thr | Glu | Arg 640 |
| Leu | Glu | Arg | Arg | Asn 645 | Lys | Ile | Leu | Arg | Glu 650 | Arg | Gly | Glu | Asn 655 | Gly | Leu |
| Ser | Lys | Asn | Val 660 | Pro | Ala | Leu | His | Met 665 | Gly | Gly | Leu | | | | |

( 2 ) INFORMATION FOR SEQ ID NO:14:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:14:

-continued

```
TT Y TA Y GGNG  CNTT Y T-
T Y AT  HGA                                                              23
```

( 2 ) INFORMATION FOR SEQ ID NO:15:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:15:

```
ATBCT Y TCNG  GNGCCATKTA                                                 20
```

( 2 ) INFORMATION FOR SEQ ID NO:16:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:16:

```
A S T Y R Y SASA  SASA-
S Y S                                                                    17
```

What is claimed is:

1. An isolated and purified polynucleotide sequence encoding a polypeptide comprising the amino acid sequence set forth in SEQ ID NO:2.

2. The isolated and purified polynucleotide sequence of claim 1, wherein said polynucleotide sequence is selected from the group consisting of (a) SEQ ID NO:1, (b) degenerate variants of SEQ ID NO:1, and (c) polynucleotide sequence fully complementary to either (a) or (b).

3. A recombinant expression vector comprising the polynucleotide sequence of claim 1.

4. A recombinant host cell transformed with the recombinant expression vector of claim 3.

5. An isolated and purified polynucleotide sequence encoding a polypeptide comprising the amino acid sequence set forth in SEQ ID NO:4.

6. The isolated and purified polynucleotide sequence of claim 5, wherein said polynucleotide sequence is selected from the group consisting of (a) SEQ ID NO:3, (b) degenerate variants of SEQ ID NO:3, and (c) polynucleotide sequence fully complementary to either (a) or (b).

7. A recombinant expression vector comprising the polynucleotide sequence of claim 5.

8. A recombinant host cell transformed with the recombinant expression vector of claim 7.

9. An isolated and purified polynucleotide sequence encoding a polypeptide comprising the amino acid sequence set forth in SEQ ID NO:6.

10. The isolated and purified polynucleotide sequence of claim 9, wherein said polynucleotide sequence is selected from the group consisting of (a) SEQ ID NO:5, (b) degenerate variants of SEQ ID NO:5, and (c) polynucleotide sequence fully complementary to either (a) or (b).

11. A recombinant expression vector comprising the polynucleotide sequence of claim 9.

12. A recombinant host cell transformed with the recombinant expression vector of claim 11.

13. An isolated and purified polynucleotide sequence encoding a polypeptide comprising the amino acid sequence set forth in SEQ ID NO:8.

14. The isolated and purified polynucleotide sequence of claim 13, wherein said polynucleotide sequence is selected from the group consisting of (a) SEQ ID NO:7, (b) degenerate variants of SEQ ID NO:7, and (c) polynucleotide sequence fully complementary to either (a) or (b).

15. A recombinant expression vector comprising the polynucleotide sequence of claim 13.

16. A recombinant host cell transformed with the recombinant expression vector of claim 15.

17. An isolated and purified polynucleotide sequence encoding a polypeptide comprising the amino acid sequence set forth in SEQ ID NO:10.

18. The isolated and purified polynucleotide sequence of claim 17, wherein said polynucleotide sequence is selected from the group consisting of (a) SEQ ID NO:9, (b) degenerate variants of SEQ ID NO:9, and (c) polynucleotide sequence fully complementary to either (a) or (b).

19. A recombinant expression vector comprising the polynucleotide sequence of claim 17.

20. A recombinant host cell transformed with the recombinant expression vector of claim 19.

* * * * *